United States Patent
Yoon et al.

(10) Patent No.: US 11,844,275 B2
(45) Date of Patent: Dec. 12, 2023

(54) ORGANIC COMPOUND, ORGANIC LIGHT EMITTING DIODE AND ORGANIC LIGHT EMITTING DEICE INCLUDING THE ORGANIC COMPOUND

(71) Applicants: LG Display Co., Ltd., Seoul (KR); Korea University Research and Business Foundation, Seoul (KR)

(72) Inventors: Dae-Wi Yoon, Paju-si (KR); Suk-Young Bae, Paju-si (KR); In-Ae Shin, Paju-si (KR); Su-Na Choi, Paju-si (KR); Dong-Hoon Choi, Paju-si (KR); Min-Ju Cho, Paju-si (KR); Jiwon Yoon, Paju-si (KR)

(73) Assignees: LG DISPLAY CO., LTD., Seoul (KR); KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 406 days.

(21) Appl. No.: 17/068,313

(22) Filed: Oct. 12, 2020

(65) Prior Publication Data
US 2021/0119147 A1   Apr. 22, 2021

(51) Int. Cl.
C07D 487/04   (2006.01)
C07D 513/04   (2006.01)
(Continued)

(52) U.S. Cl.
CPC ....... H10K 85/6572 (2023.02); C07D 513/04 (2013.01); H10K 50/11 (2023.02);
(Continued)

(58) Field of Classification Search
CPC ............ H01L 51/0071; H01L 51/0072; H10K 85/657; H10K 85/6572; C07D 271/12; C07D 407/14
See application file for complete search history.

(56) References Cited

U.S. PATENT DOCUMENTS

2012/0113380 A1   5/2012   Geivandov et al.
2013/0092922 A1*  4/2013   Stoessel ............... C07D 487/04
                                                      544/212
(Continued)

FOREIGN PATENT DOCUMENTS

CN    106749320 A  *  5/2017  ........... C07D 498/04
WO    2015175558 A2    11/2015

OTHER PUBLICATIONS

CN-106749320-A—translation (Year: 2017).*
(Continued)

Primary Examiner — Sean M DeGuire
Assistant Examiner — Rachel Simbana
(74) Attorney, Agent, or Firm — POLSINELLI PC

(57) ABSTRACT

The present disclosure relates to an organic compound having the following structure, and an organic light emitting diode (OLED) and an organic light emitting device including the organic compound. The organic compound is a bipolar compound having a p-type moiety and an n-type moiety and has high energy level and proper energy bandgap for an emissive layer of the OLED. As the organic compound is applied into the emissive layer, the OLED can maximize its luminous properties as holes and electrons are recombined uniformly over the whole area in an EML.

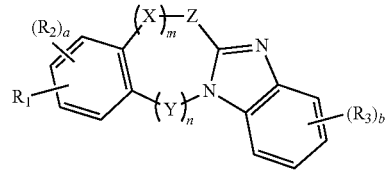

25 Claims, 16 Drawing Sheets

(51) Int. Cl.
 *C07D 519/00* (2006.01)
 *H10K 101/00* (2023.01)
 *H10K 101/20* (2023.01)
 *H10K 101/40* (2023.01)
 *H10K 50/11* (2023.01)
 *H10K 50/12* (2023.01)
 *H10K 50/16* (2023.01)
 *H10K 50/18* (2023.01)
 *H10K 85/60* (2023.01)

(52) U.S. Cl.
 CPC ............. *H10K 50/16* (2023.02); *H10K 50/18* (2023.02); *H10K 2101/40* (2023.02)

(56) References Cited

U.S. PATENT DOCUMENTS

2014/0042370 A1* 2/2014 Martynova .......... H10K 85/633
 546/37
2018/0370978 A1 12/2018 Wolohan et al.
2019/0288221 A1* 9/2019 Yoshizaki .......... H10K 85/6572

OTHER PUBLICATIONS

Wang, R.; Qian, W.; Bao, W.; 2012, Imidazobenzothiazine and primidobenzothiazine derivatives synthesis via an aliphantic SN2 substitution/Cu(I) catalyzed Ullmann coupling cascade process, Tetrahedron Letters, 53, 442-445 (Year: 2012).*
Chinese Office Action dated Jan. 20, 2023 issued in Patent Application No. 202011108387.4 w/English Translation (14 pages).

* cited by examiner

ORGANIC COMPOUND, ORGANIC LIGHT EMITTING DIODE AND ORGANIC LIGHT EMITTING DEICE INCLUDING THE ORGANIC COMPOUND

CROSS-REFERENCE TO RELATED APPLICATIONS

This application claims the priority benefit under 35 U.S.C. § 119(a) to Korean Patent Application Nos. 10-2019-0130224, filed on Oct. 18, 2019 and No. 10-2020-0112041, filed on Sep. 3, 2020, all of which are hereby incorporated by reference in its entirety.

BACKGROUND

Field of the Disclosure

The present disclosure relates to an organic compound, and more specifically, to an organic compound having enhanced luminous properties, an organic light emitting diode and an organic light emitting device including the organic compound.

Description of the Background

As display devices have become larger, there exists a need for a flat display device with a lower space requirement. Among the flat display devices used widely at present, displays having organic light emitting diodes (OLEDs) are rapidly replacing liquid crystal display devices (LCDs).

The OLED can be formed as a thin film having a thickness less than 2000 Å and can be implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high. Particularly, the OLED can implement red, green and blue colors, thus it has attracted a lot of attention as a light emitting device.

In the OLED, holes injected from an anode and electrons injected from a cathode are recombined in an EML to form excitons as an unstable excites state, and then the light emits as the exciton is shifted to a stable ground state. The conventional fluorescent materials in which only singlet excitons involved in the luminescence process have low luminous efficiency. The phosphorescent materials in which triplet excitons as well as singlet excitons involved in the luminescence process have relatively high luminous efficiency. However, the metal complex, representative phosphorescent materials, has too short luminous lifetime to be applicable to commercial devices. Particularly, the luminous materials for implementing blue emission have deteriorated luminous properties and luminous lifetime.

SUMMARY

Accordingly, the present disclosure is directed to an organic compound and an OLED and an organic light emitting device including the organic compound that substantially obviates one or more of the problems due to the limitations and disadvantages of the related art.

In addition, the present disclosure is to provide an organic compound having high excited triplet energy level as well as bipolar properties, an OLED and an organic light emitting device into which the organic compound is applied.

Further, the present disclosure is to provide an organic compound that has excellent thermal stability as well as high affinity to charges, an OLED and an organic light emitting device having the compound.

Additional features and aspects will be set forth in the description that follows, and in part will be apparent from the description, or may be learned by practice of the inventive concepts provided herein. Other features and aspects of the inventive concept may be realized and attained by the structure particularly pointed out in the written description, or derivable therefrom, and the claims hereof as well as the appended drawings.

To achieve these and other aspects of the present disclosure, as embodied and broadly described, the present disclosure provides an organic compound having the following structure of Chemical Formula 1:

[Chemical Formula 1]

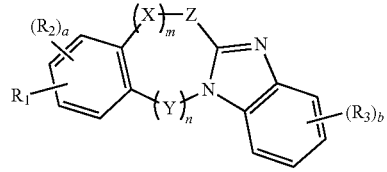

wherein $R_1$ is an unsubstituted or substituted fused hetero aromatic group having three to six aromatic or hetero aromatic rings and having one to three nitrogen atoms, an unsubstituted or substituted $C_6$-$C_{30}$ aromatic amino group or an unsubstituted or substituted $C_4$-$C_{30}$ hetero aromatic amino group; each of $R_2$ and $R_3$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, wherein each of $R_2$ and $R_3$ is identical to or different from each other when each of a and b is independently an integer two or more; each of a and b is independently the number of a substituent, a is an integer of 0 (zero) to three and b is an integer of 0 (zero) to four; each of X and Y is independently $CR_4R_5$, wherein each of $R_4$ and $R_5$ is independently selected from the group consisting of hydrogen, an unsubstituted or substituted $C_1$-$C_{30}$ alkyl group, an unsubstituted or substituted C6-C30 aromatic group and an unsubstituted or substituted $C_3$-$C_{30}$ hetero aromatic group, or $R_4$ and $R_5$ form a $C_6$-$C_{20}$ aromatic ring or a $C_3$-$C_{20}$ hetero aromatic ring; each of m and n is 0 (zero) or 1, wherein m+n=1; Z is S, O or $NR_6$, wherein $R_6$ is hydrogen, an unsubstituted or substituted $C_1$-$C_{30}$ alkyl group, an unsubstituted or substituted $C_6$-$C_{30}$ aromatic group, or an unsubstituted or substituted $C_3$-$C_{30}$ hetero aromatic group.

In another aspect, the present disclosure provides an OLED that comprises a first electrode; a second electrode facing the first electrode; and an emissive layer disposed between the first and second electrodes, wherein the emissive layer comprises the organic compound.

For example, at least one of an ETL, a HBL, an EML and a CGL may comprise the organic compound.

As an example, the EML may comprise the organic compound as a host, and in this case the EML may further comprise at least one dopant such as delayed fluorescent material, fluorescent material and phosphorescent material.

In still another aspect, the present disclosure provides an organic light emitting device, such as an organic light emitting display device and an organic light emitting illumination device that comprises a substrate and an OLED disposed over the substrate, as described above.

It is to be understood that both the foregoing general description and the following detailed description are exemplary and explanatory and are intended to provide further explanation of the inventive concepts as claimed.

BRIEF DESCRIPTION OF THE DRAWINGS

The accompanying drawings, which are included to provide a further understanding of the disclosure, are incorporated in and constitute a part of the present disclosure, illustrate aspects of the disclosure and together with the description serve to explain principles of the disclosure.

In the drawings.

DETAILED DESCRIPTION

Figure 1:
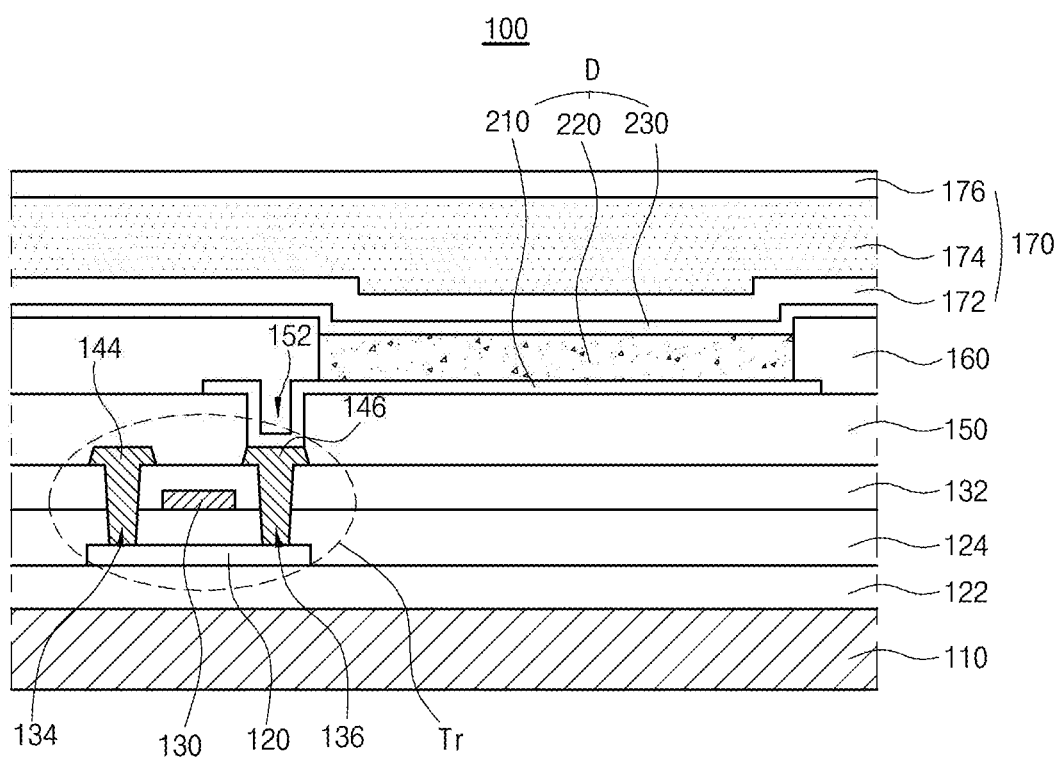
FIG. 1 is a schematic cross-sectional view illustrating an organic light emitting display device in accordance with an exemplary aspect of the present disclosure.

Reference and discussions will now be made below in detail to aspects, and examples of the disclosure, some examples of which are illustrated in the accompanying drawings.

[Organic Compound]

An organic compound applied in to an organic light emitting diode (OLED) should have excellent luminous properties, high affinity to charges and maintain stable properties in driving the OLED. Particularly, luminous material applied into the diode is the most important factor determining the luminous efficiency of the OLED. The luminous material should have high quantum efficiency, large mobility for charges and adequate energy levels with regard to other materials applied into the same or adjacent layers. An organic compound includes a fused aromatic ring including a benzimidazole moiety having high affinity to electrons, and a fused hetero aromatic ring or a (hetero) aromatic amino group having high affinity to holes. An organic compound in accordance with the present disclosure may have the following structure of Chemical Formula 1:

[Chemical Formula 1]

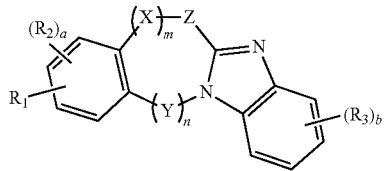

In Chemical Formula 1, $R_1$ is an unsubstituted or substituted fused hetero aromatic group having three to six aromatic or hetero aromatic rings and having one to three nitrogen atoms, an unsubstituted or substituted $C_6$-$C_{30}$ aromatic amino group or an unsubstituted or substituted $C_4$-$C_{30}$ hetero aromatic amino group; each of $R_2$ and $R_3$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, wherein each of $R_2$ and $R_3$ is identical to or different from each other when each of a and b is independently an integer two or more; each of a and b is independently the number of a substituent, a is an integer of 0 (zero) to three and b is an integer of 0 (zero) to four; each of X and Y is independently $CR_4R_5$, wherein each of $R_4$ and $R_5$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, or $R_4$ and $R_5$ form a $C_6$-$C_{20}$ aromatic ring or a $C_3$-$C_{20}$ hetero aromatic ring; each of m and n is 0 (zero) or 1, wherein m+n=1; Z is S, O or $NR_6$, wherein R6 is hydrogen, an unsubstituted or substituted $C_1$-$C_{30}$ alkyl group, an unsubstituted or substituted $C_6$-$C_{30}$ aromatic group, or an unsubstituted or substituted $C_3$-$C_{30}$ hetero aromatic group.

As used herein, the term 'unsubstituted" means that hydrogen is linked, and in this case, hydrogen comprises protium, deuterium and tritium.

As used herein, substituent in the term "substituted" comprises, but is not limited to, unsubstituted or halogen-substituted $C_1$-$C_{20}$ alkyl, unsubstituted or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term 'hetero" in such as "a hetero aromatic ring", "a hetero cycloalkylene group", "a hetero arylene group", "a hetero aryl alkylene group", "a hetero aryl oxylene group", "a hetero cycloalkyl group", "a hetero aryl group", "a hetero aryl alkyl group", "a hetero aryloxyl group", "a hetero aryl amino group" means that at least one carbon atom, for example 1-5 carbons atoms, constituting an aromatic ring or an alicyclic ring is substituted with at least one hetero atom selected from the group consisting of N, O, S, P and combination thereof.

The central fused aromatic ring in the organic compound having the structure of Chemical Formula 1 includes the benzimidazole moiety that has excellent affinity to electrons and therefore, has the n-type property inducing the electron injections and transportations. Also, the fused hetero aromatic ring or the (hetero) aromatic amino group linked to the central fused aromatic ring has excellent affinity to holes and therefore, has the p-type property inducing the hole injections and transportations. Accordingly, the organic compound having the structure of Chemical Formula 1 has the bipolar property.

In one aspect, the fused hetero aromatic group in $R_1$ is unsubstituted, substituted with a group selected from a $C_1$-$C_{20}$ alkyl group, a $C_6$-$C_{20}$ aryl group, a $C_3$-$C_{20}$ hetero aryl group and combination thereof, or forms a spiro structure with a fluorene ring or a xanthene ring. In another aspect, the fused hetero aromatic group in $R_1$ is unsubstituted, substituted with a group selected from a $C_1$-$C_{10}$ alkyl group, phenyl, carbazolyl and combination thereof, or forms a spiro structure with a xanthene ring.

In one exemplary aspect, the fused hetero aromatic group in $R_1$ is selected from the group consisting of a carbazolyl moiety, an acridinyl moiety, a dihydro acridinyl moiety, a phenazinyl moiety and a phenoxazinyl moiety. For example, each of the carbazolyl moiety, the acridinyl moiety, the dihydro acridinyl moiety, the phenazinyl moiety and the phenoxazinyl moiety may comprise a carbazolyl group, an acridinyl group, a dihydro acridinyl group, a phenazinyl group and a phenoxazinyl group each of which is unfused or fused with, but is not limited to, a benzene ring, a furan ring, a thiophene ring, an indene ring and/or an indole ring.

As an example, the $C_6$-$C_{30}$ aryl group substituted to $R_1$ may comprise, but is not limited to, an unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spiro-fluorenyl.

In another exemplary aspect, the $C_3$-$C_{30}$ hetero aryl group substituted to $R_1$ may comprise independently, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzo-furo-carbazolyl, benzo-thieno-carbazolyl, carbolinyl, quinolinyl, iso-quinolinyl, phthlazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzo-furanyl, dibenzo-furanyl, thiopyranyl, xanthenyl, chromenyl, iso-chromenyl, thioazinyl, thiophenyl, benzo-thiophenyl, dibenzo-thiophenyl, difuro-pyrazinyl, benzo-furo-dibenzo-furanyl, benzothieno-benzo-thiophenyl, benzothieno-dibenzo-thiophenyl, benzothieno-benzo-furanyl, benzothieno-dibenzo-furanyl, xanthne-linked spiro acridinyl, dihydroacridinyl substituted with at least one $C_1$-$C_{10}$ alkyl and N-substituted spiro fluorenyl.

As an example, when $R_1$ is the fused hetero aromatic group such as the unfused or fused carbazolyl group, the acridinyl group, the dihydro acridinyl group, the phenazinyl group and the phenoxazinyl group, the fused hetero aromatic group may further substituted with one to three other fused hetero aromatic groups. In this case, the other fused hetero aromatic group substituted to $R_1$ may comprises, but is not limited to, a carbazolyl group, an acridinyl group, a dihydro acridinyl group, a phenazinyl group and/or a phenoxazinyl group.

As an example, the aryl group or the hetero aryl group that may be substituted to $R_1$ may have one to three aromatic or hetero aromatic rings. When the number of the aromatic or the hetero aromatic ring that may be substituted to $R_1$ becomes large, the conjugated structure within the whole molecule is too long, and therefore the organic compound may have excessively reduced energy bandgap. As an example, the aryl group and the hetero aryl group that may be substituted to $R_1$ may comprise, but is not limited to, phenyl, biphenyl, naphthyl, anthracenyl, benzo-furanyl, dibenzo-furanyl, benzo-thiophenyl, dibenzo-thiophenyl, carbazolyl, acridinyl, phenazinyl, phenoxazinyl and/or phenothiazinyl.

In one exemplary aspect, the $C_6$-$C_{30}$ aromatic group in each of $R_2$ to $R_6$ may comprise independently a $C_6$-$C_{30}$ aryl group, a $C_7$-$C_{30}$ aryl alkyl group, a $C_6$-$C_{30}$ aryloxyl group and a $C_6$-$C_{30}$ aryl amino group. The $C_3$-$C_{30}$ hetero aromatic group in each of $R_2$ to $R_6$ may comprise independently a $C_3$-$C_{30}$ hetero aryl group, a $C_4$-$C_{30}$ hetero aryl alkyl group, a $C_3$-$C_{30}$ hetero aryloxyl group and a $C_3$-$C_{30}$ hetero aryl amino group. When the $C_6$-$C_{30}$ aromatic group or the $C_3$-$C_{30}$ hetero aromatic group in each of $R_2$ to $R_6$ is the aryl group or the hetero aryl group, the aryl group or the hetero aryl group in $R_2$ to $R_6$ may be identical to, but is not limited to, the aryl group or the hetero aryl group that may be substituted to $R_1$, as described above.

In one exemplary aspect, each of $R_4$ and $R_5$ is unsubstituted or substituted with a group selected from a $C_1$-$C_{10}$ alkyl group, phenyl and combination thereof, or $R_4$ and $R_5$ are combined to form a fluorene ring. Also, Z may be S (sulfur).

As described above, the organic compound having the structure of Chemical Formula 1 includes the benzimidazole moiety having the n-type property as well as the fused hetero aromatic moiety or the (hetero) aromatic amino group having the p-type property. The organic compound has high excited singlet and triplet energy levels and excellent thermal stability. When the organic compound is introduced into the emissive layer, for example the EML, holes and electrons can be injected into the EML in balance, and the recombination zone among the holes and electrons can be disposed uniformly over the whole area of the EML, and therefore, the OLED can maximize its luminous efficiency and luminous lifetime.

In addition, since the organic compound includes the fused aromatic ring having the benzimidazole moiety, it has wide energy bandgap between the HOMO (highest occupied molecular orbital) and the LUMO (lowest unoccupied molecular orbital) energy levels and high excited singlet and triplet energy level, and therefore it can be used as the host in the EML. When the organic compound is used as the host in the EML, exciton energy of the host can be transferred efficiently to the dopant and the exciton quenching owing to the interaction between the singlet/triplet excitons of the host or dopant and peripheral hole (or electron)-polaron can be minimized. Accordingly, it is possible to realize an OLED having excellent luminous efficiency and improved color purity by introducing the organic compound into the emissive layer.

In one exemplary aspect, the organic compound having the structure of Chemical Formula 1 may have, but is not limited to, an excited triplet energy level T1 equal to or more than about 2.80 eV, or about 2.90 eV. Also, the organic compound may have, but is not limited to, the HOMO energy level between about −5.0 eV and about −6.3 eV, the LUMO energy level between about −0.5 eV and about −2.0 eV, and the energy level bandgap between the HOMO energy level and the LUMO energy level between about 3.0 eV and about 4.7 eV. In addition, the organic compound having the structure of Chemical Formula 1 has excellent affinity to charges and low HOMO energy level, thus it can be applied into an ETL, a HBL or a N-type CGL disposed between the emitting parts.

In one exemplary aspect, m is 1 and n is 0 (zero) in Chemical Formula 1. Such an organic compound may comprise anyone having the following structure of Chemical Formula 2:

[Chemical Formula 2]

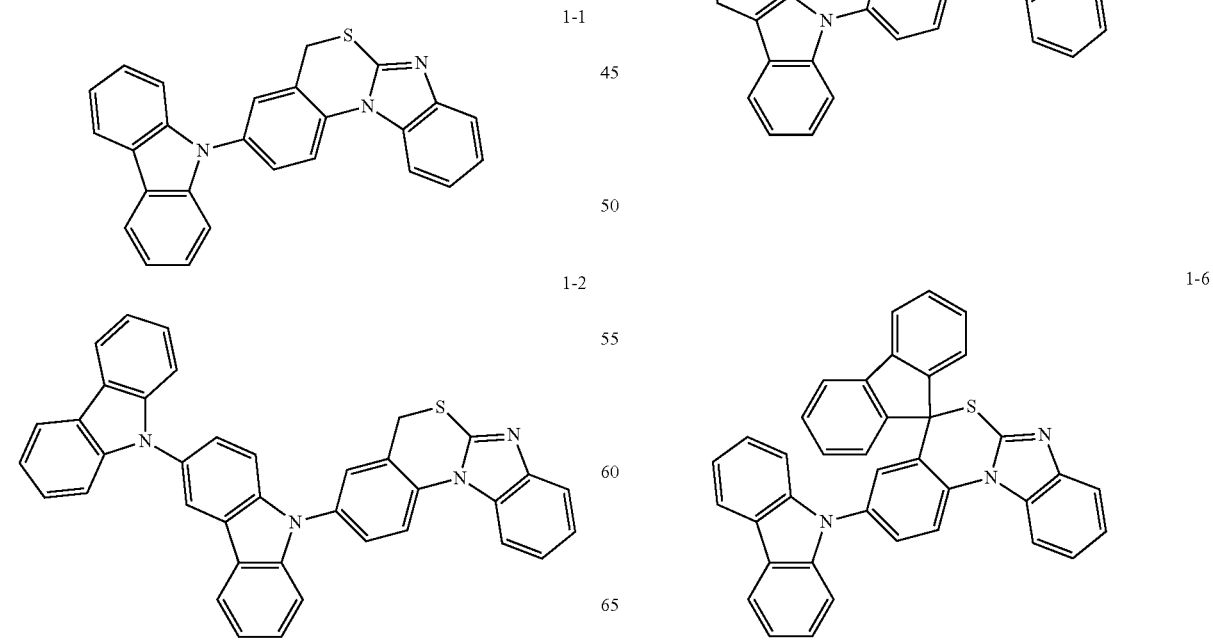

-continued
1-7
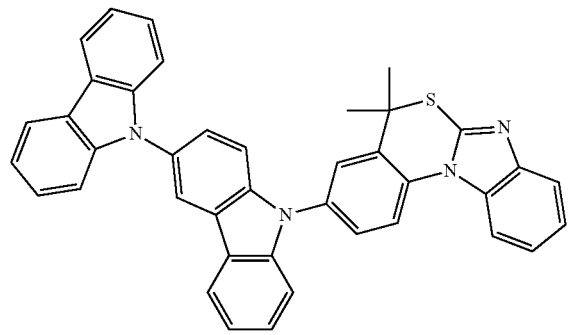
1-8
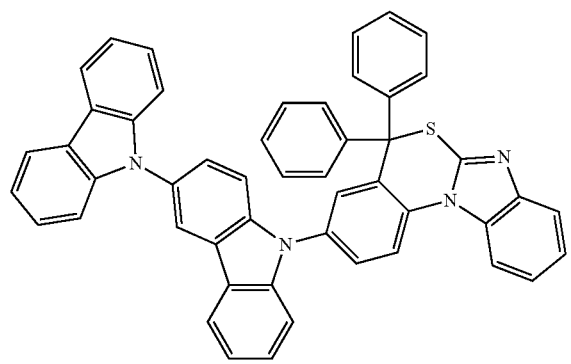
1-9
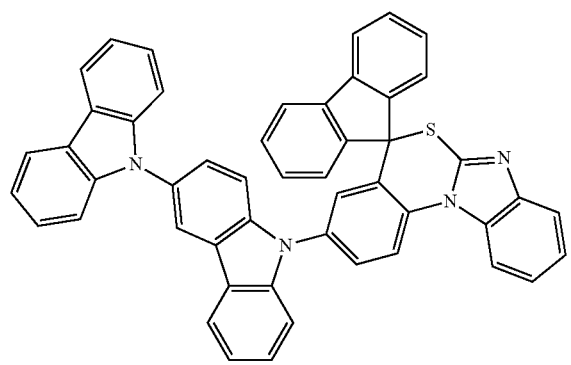
1-10
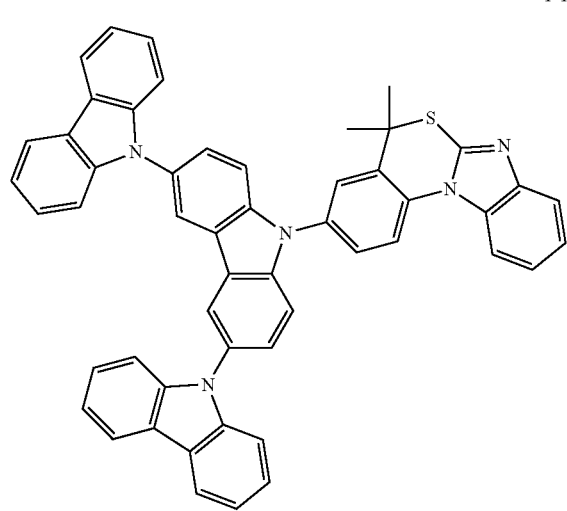
-continued
1-11
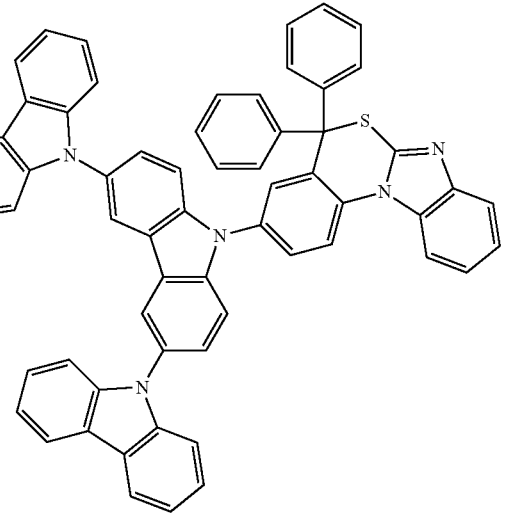
1-12
1-13

1-14
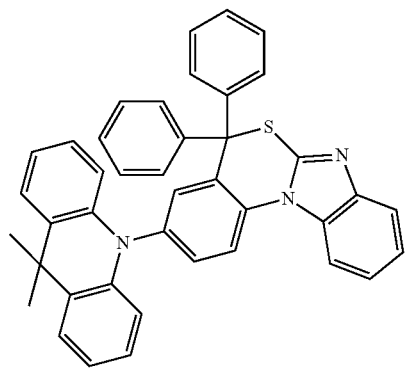
1-15
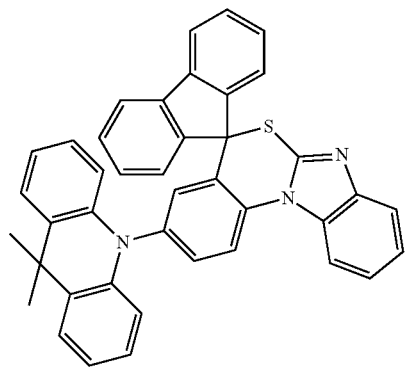
1-16
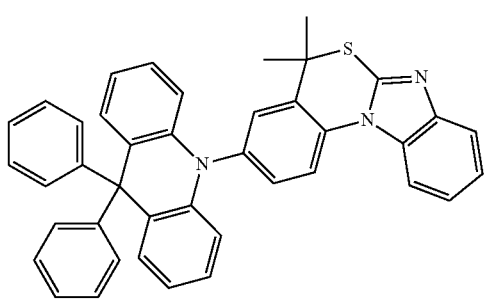
1-17
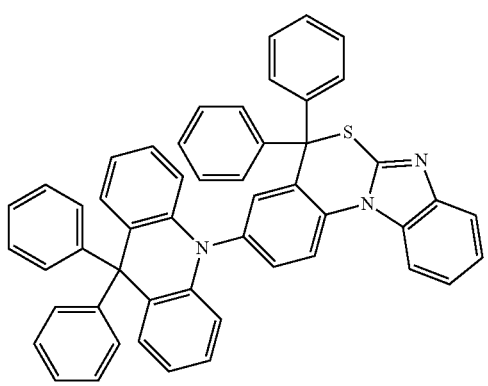
1-18
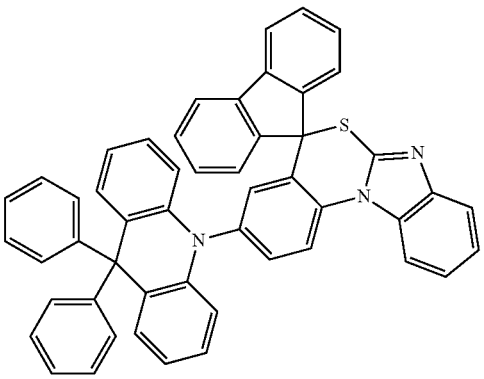
1-19
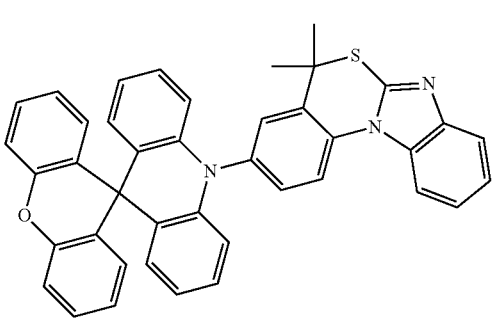
1-20
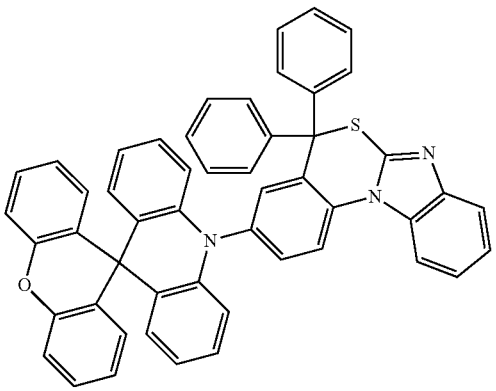
1-21
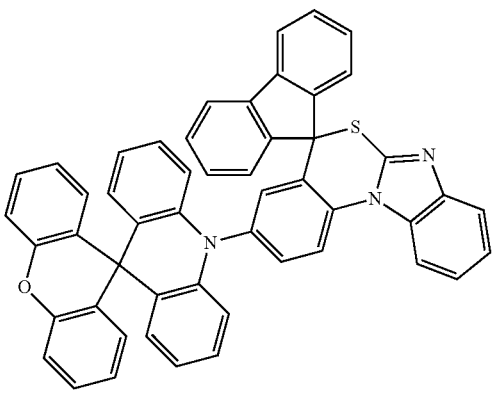

1-22
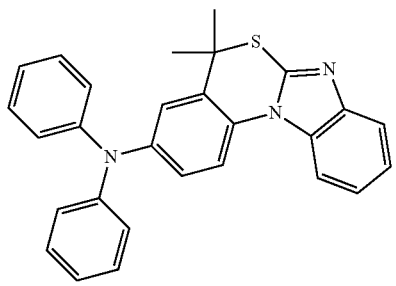
1-23
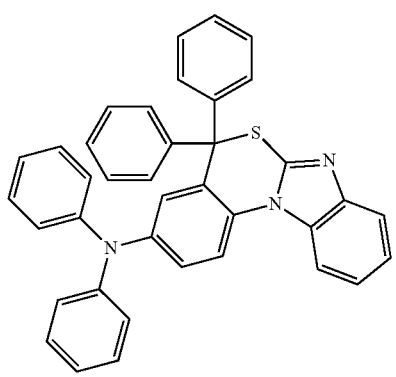
1-24
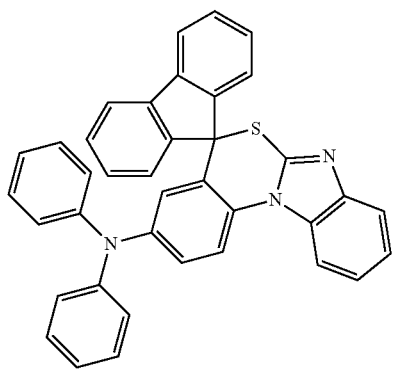
1-25
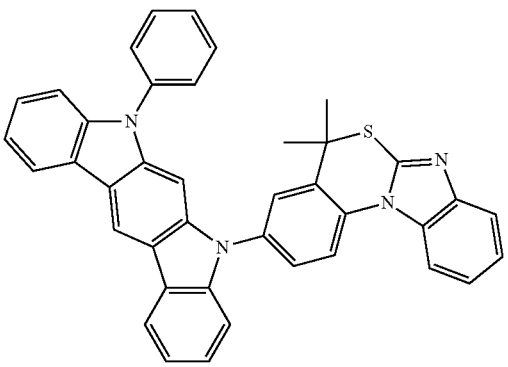
1-26
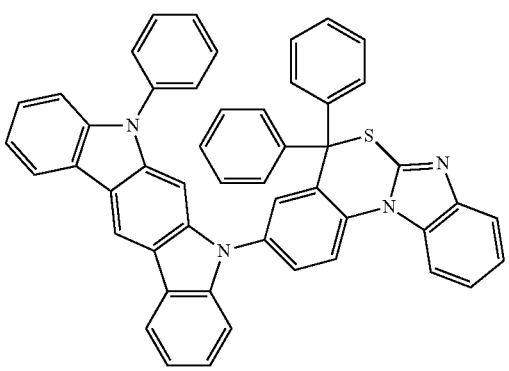
1-27
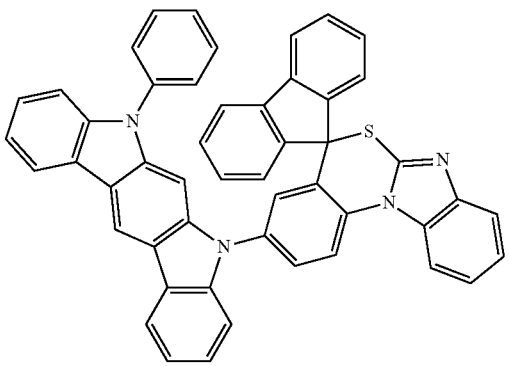
1-28
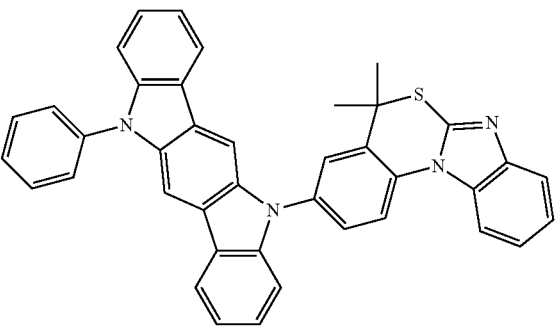
1-29
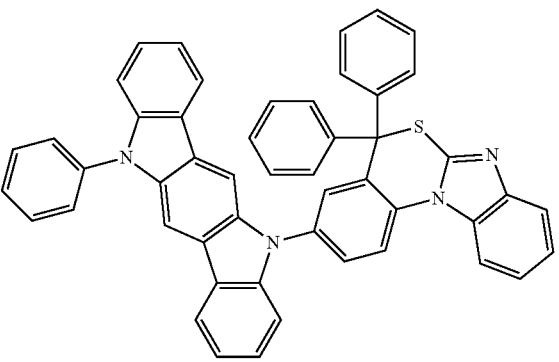

1-30
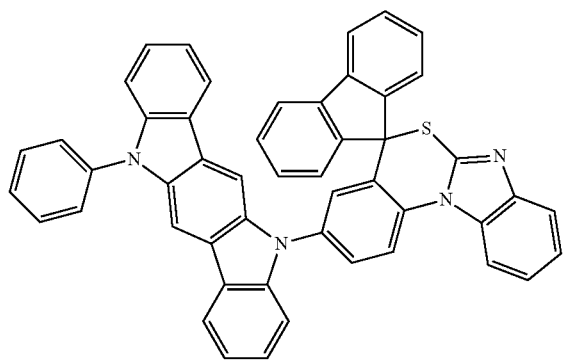
1-31
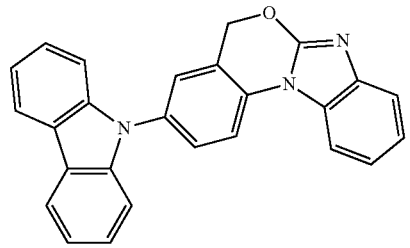
1-32
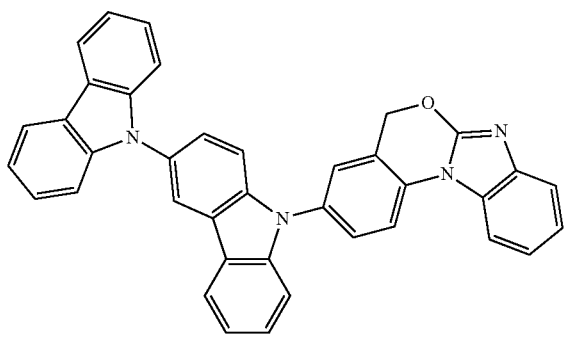
1-33
1-34
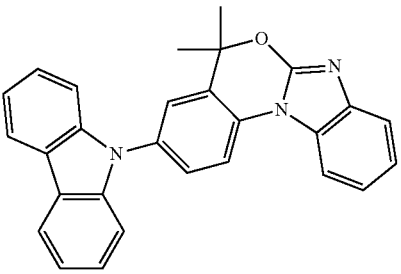
1-35
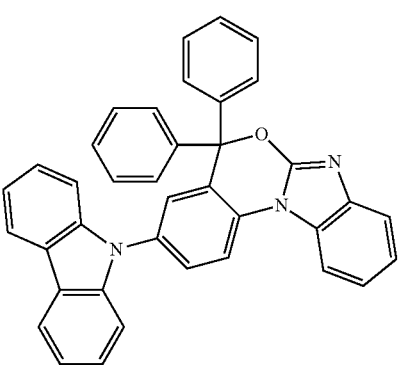
1-36
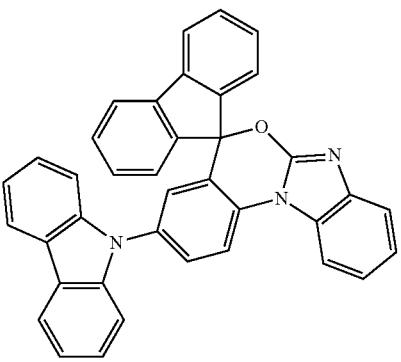
1-37
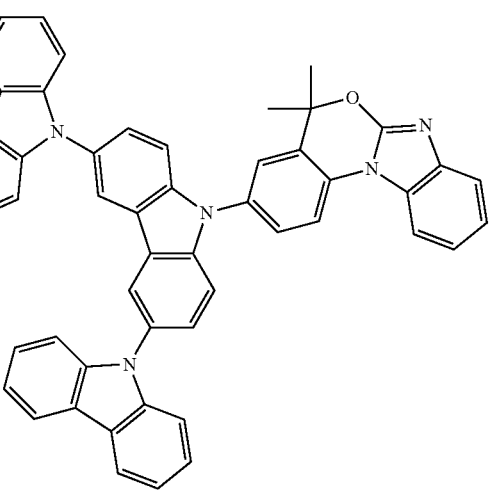

1-38
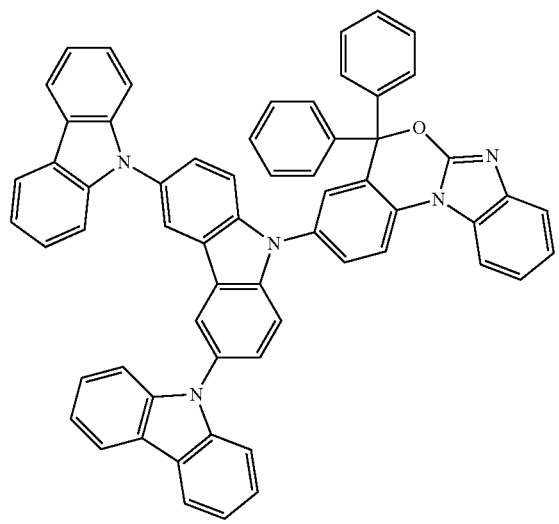
1-39
1-40
1-41
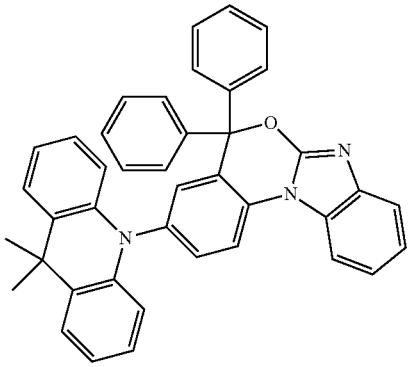
1-42
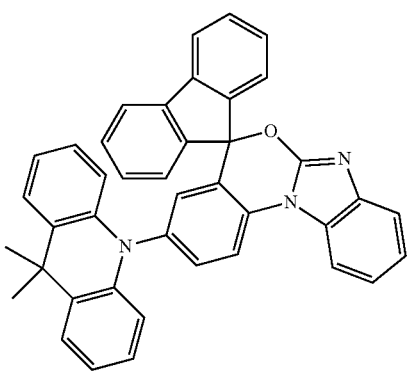
1-43
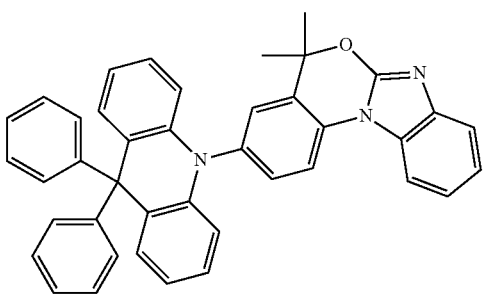
1-44
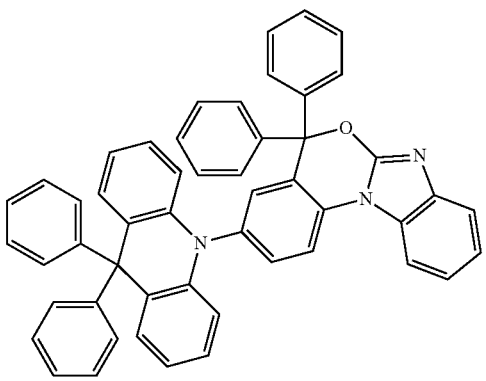

-continued
1-45
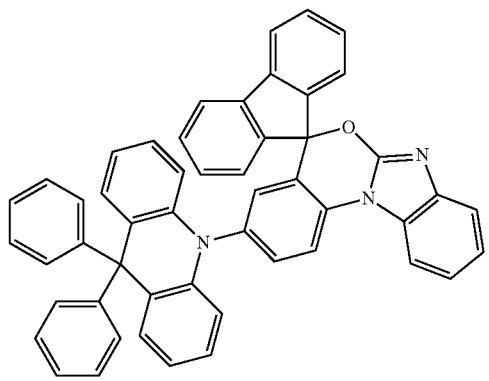
1-46
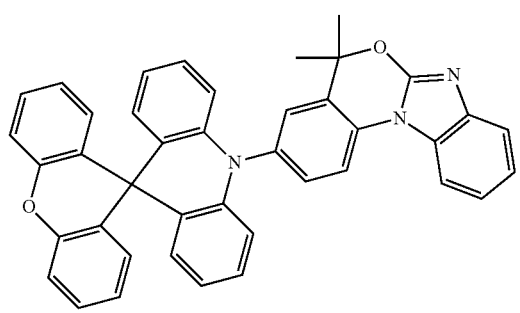
1-47
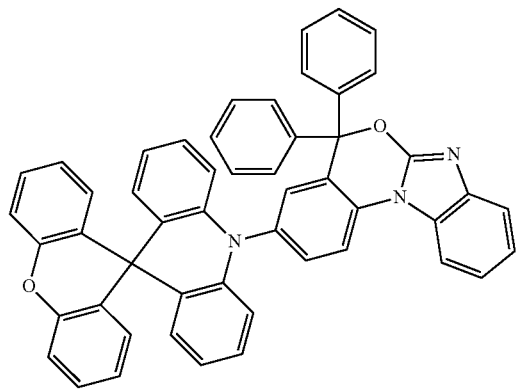
1-48
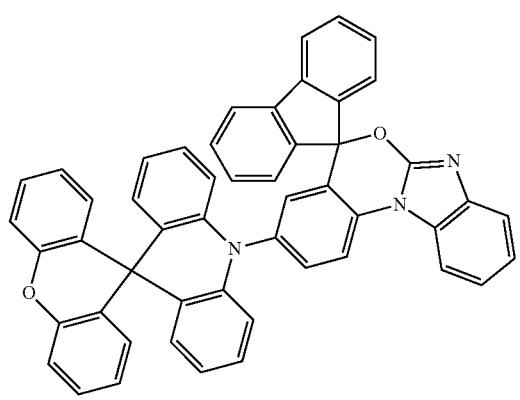
-continued
1-49
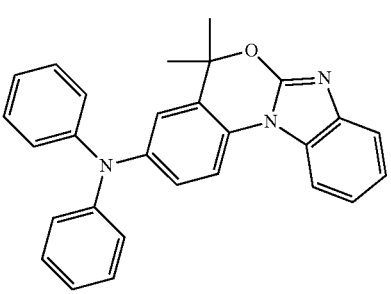
1-50
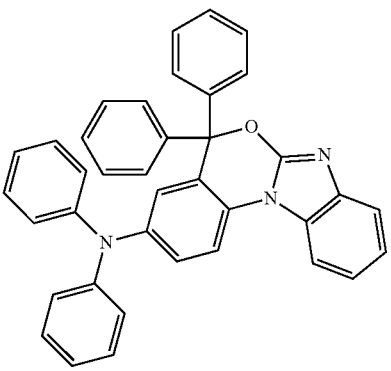
1-51
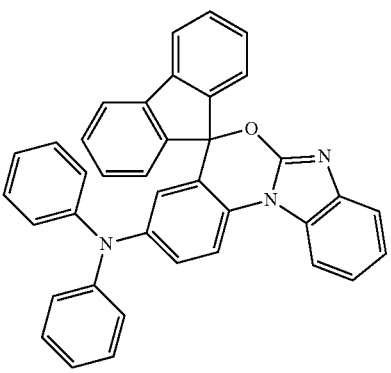
1-52
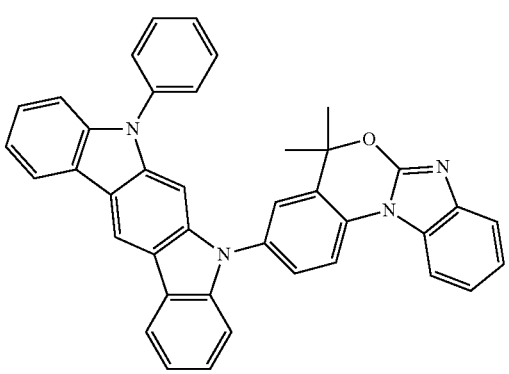

-continued
1-53
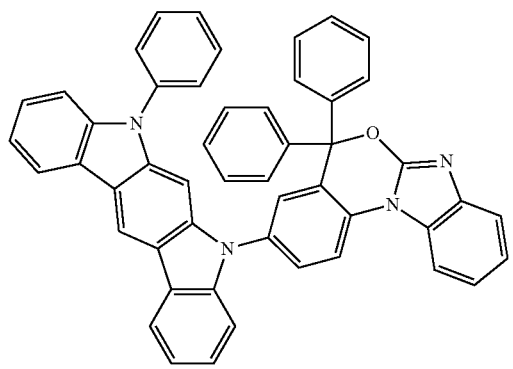
1-54
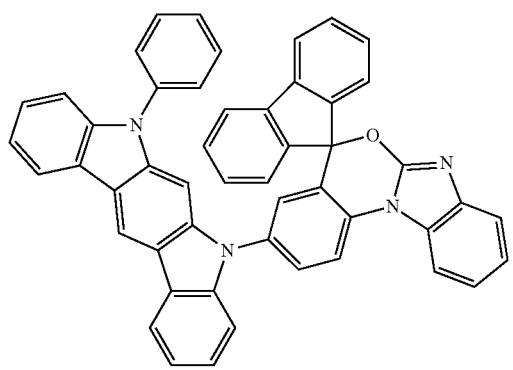
1-55
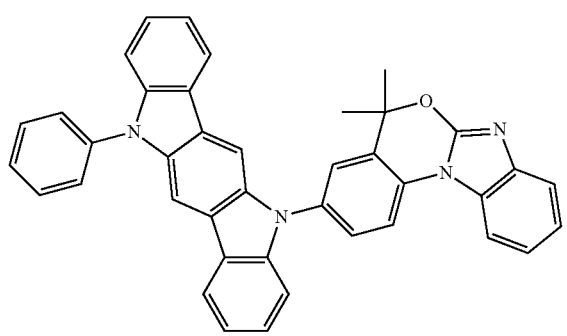
1-56
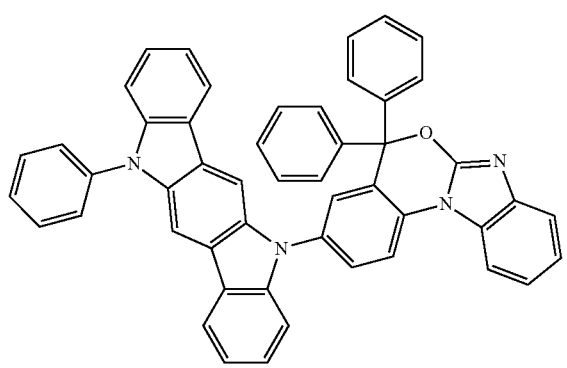
-continued
1-57
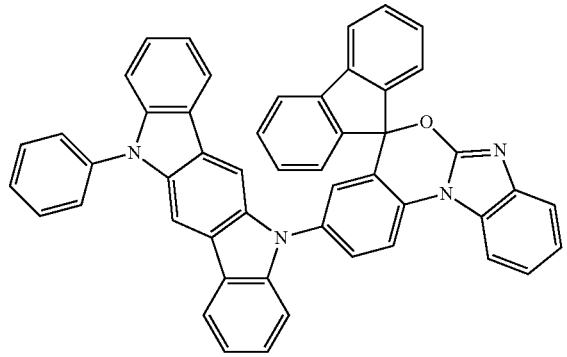
1-58
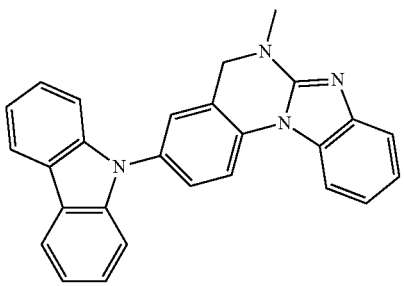
1-59
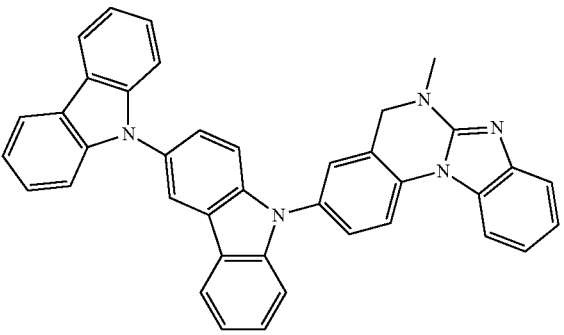
1-60
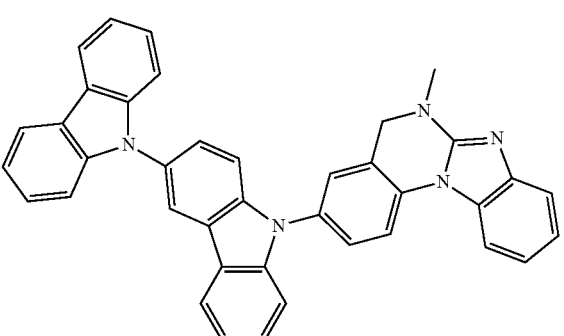

1-61
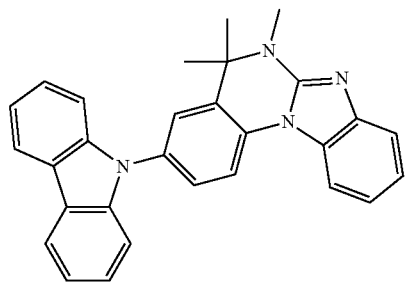
1-62
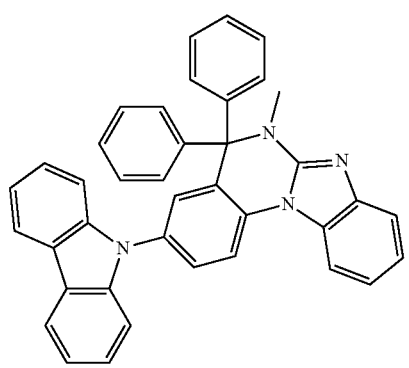
1-63
1-64
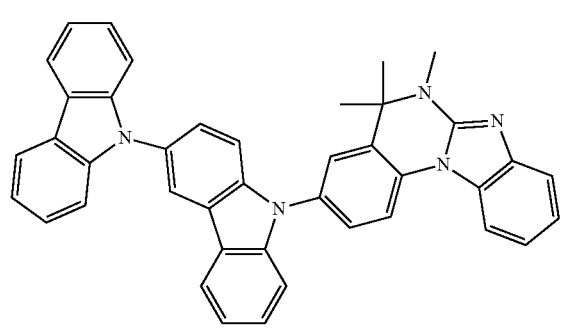
1-65
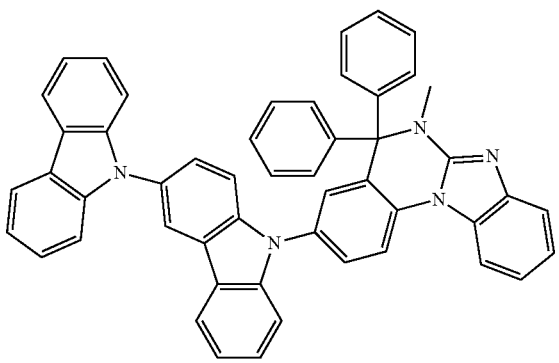
1-66
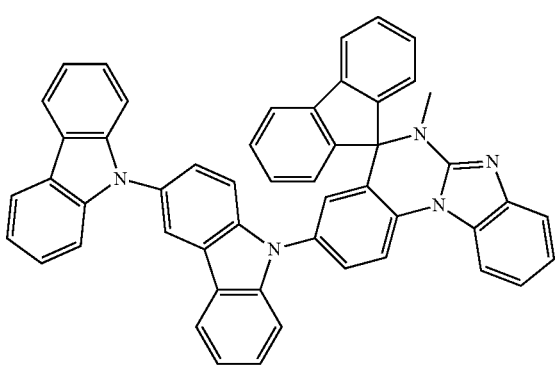
1-67

1-68
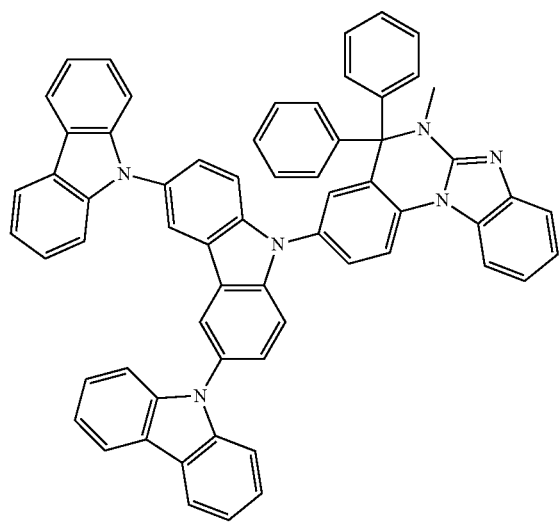
1-69
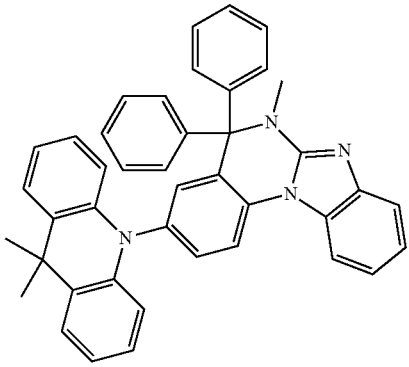
1-70
1-71
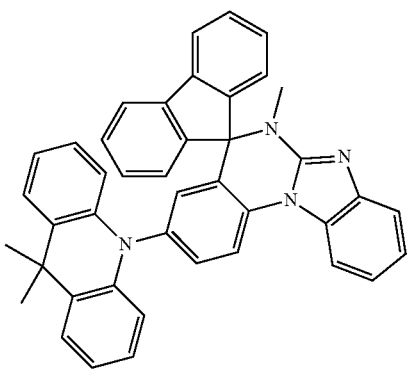
1-72
1-73
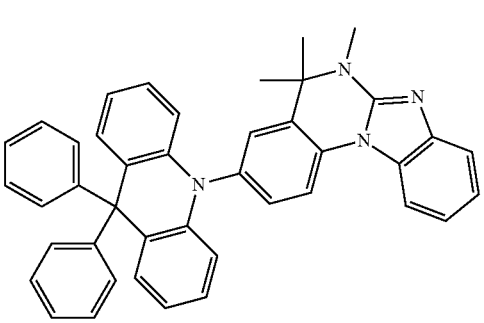
1-74
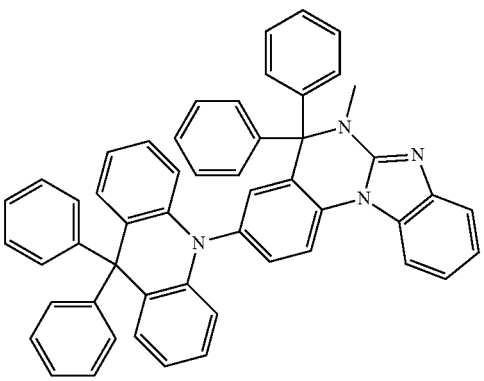

1-75
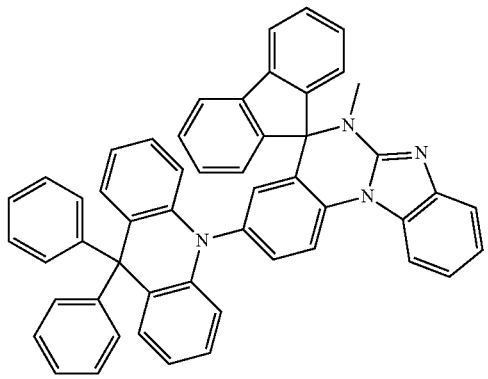
1-76
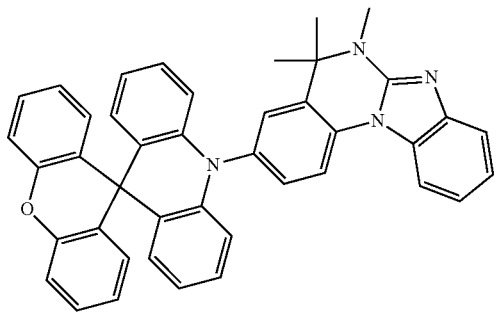
1-77
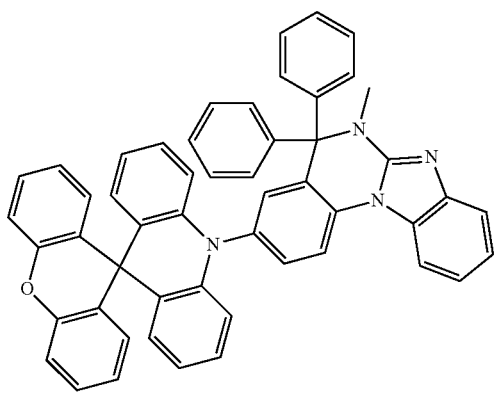
1-78
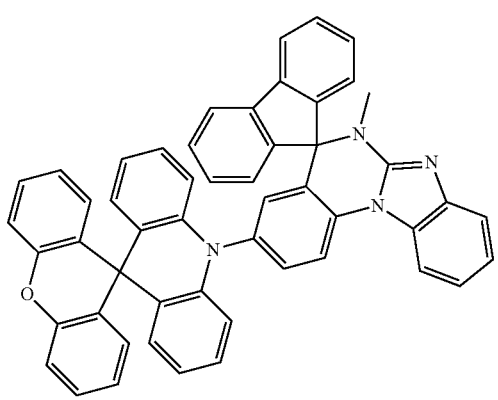
1-79
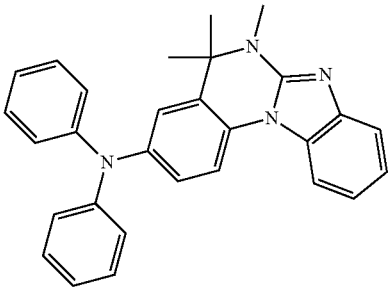
1-80
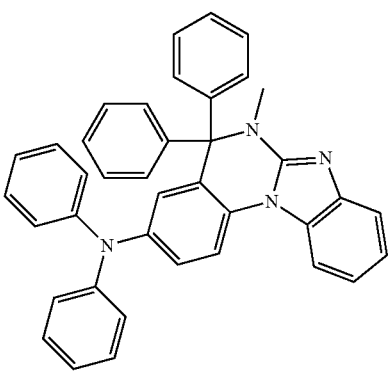
1-81
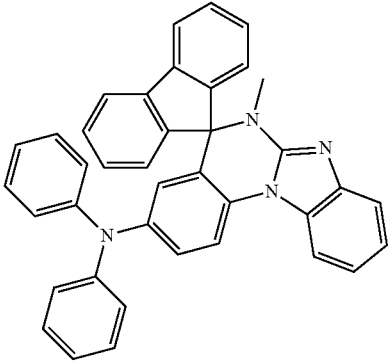
1-82
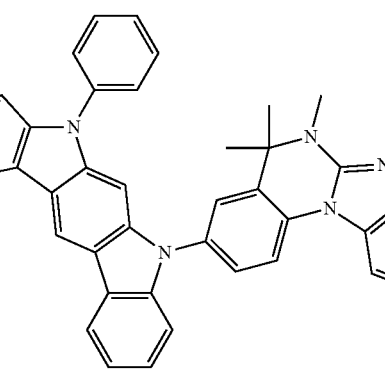

1-83
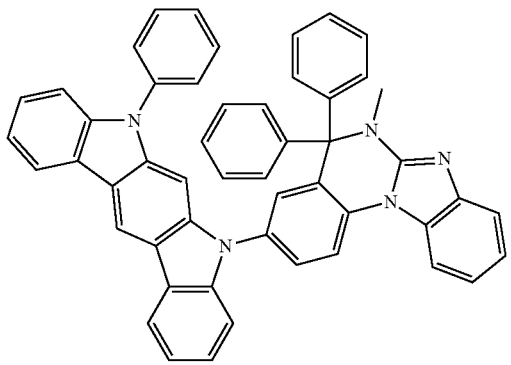
1-84
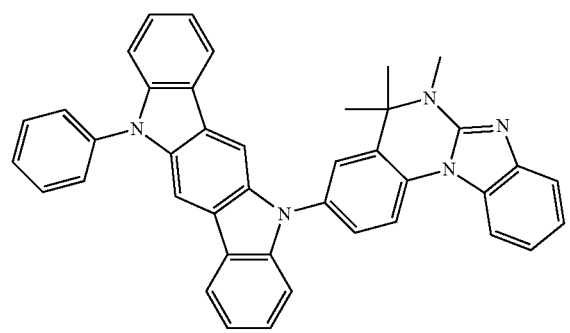
1-85
1-86
1-87
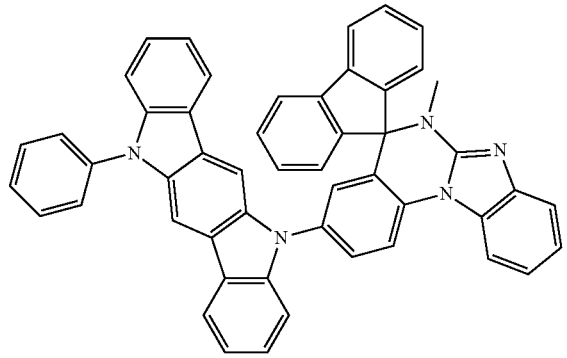
1-88
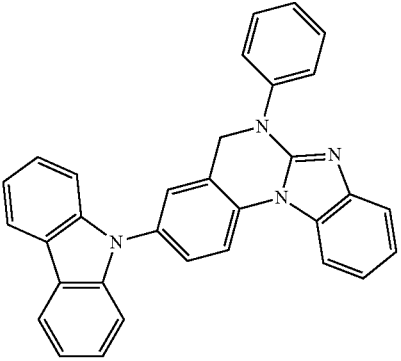
1-89
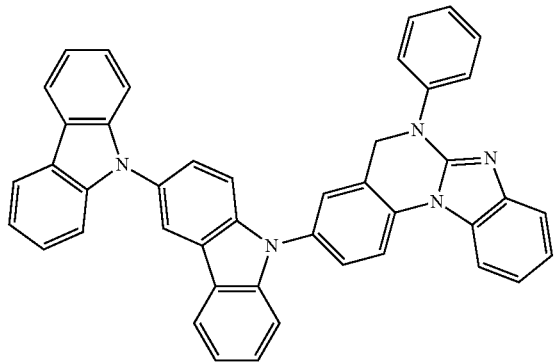

1-90
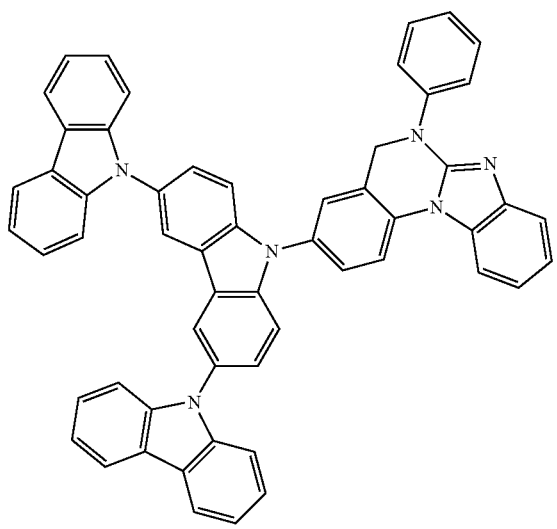
1-91
1-92
1-93
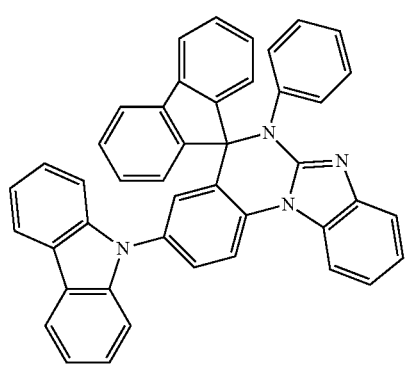
1-94
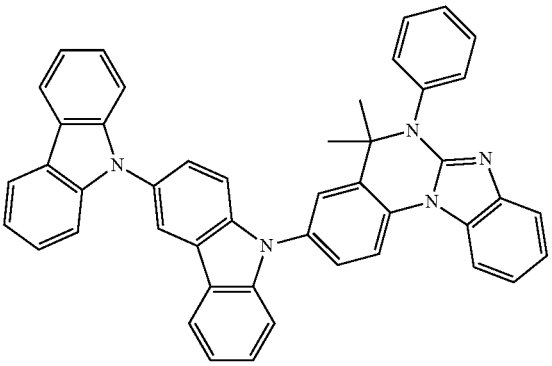
1-95
1-96
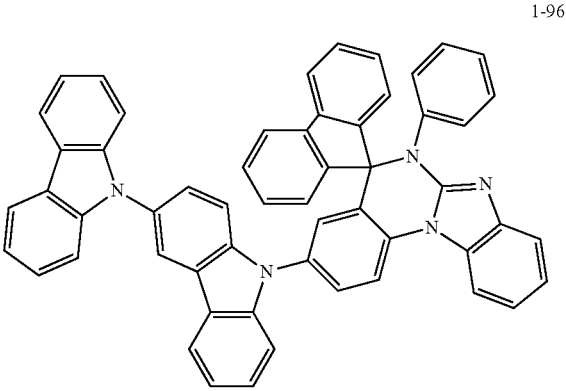

-continued
1-97
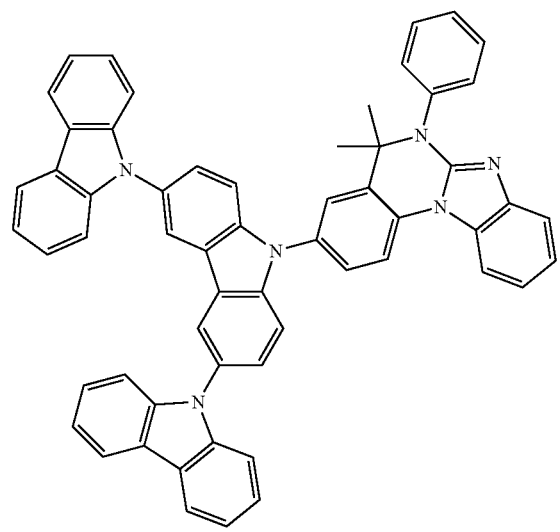
1-98
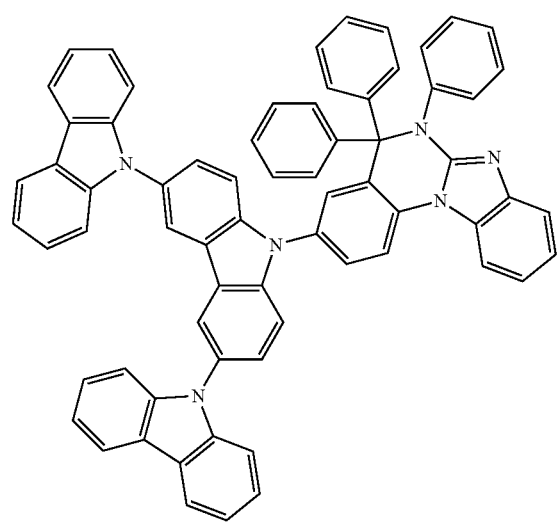
1-99
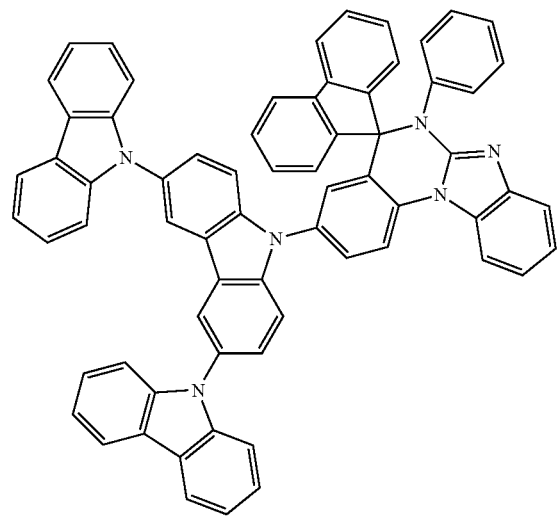
-continued
1-100
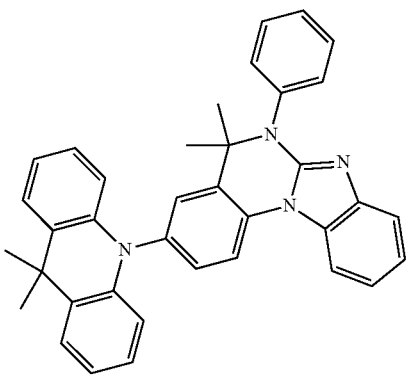
1-101
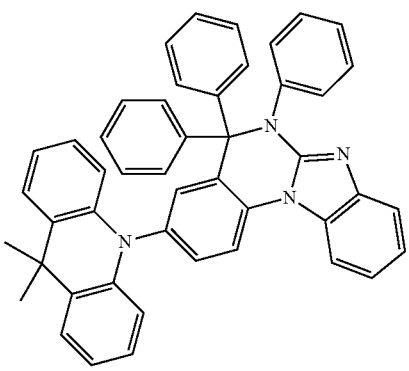
1-102
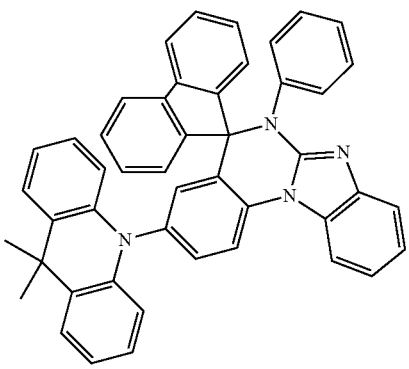
1-103
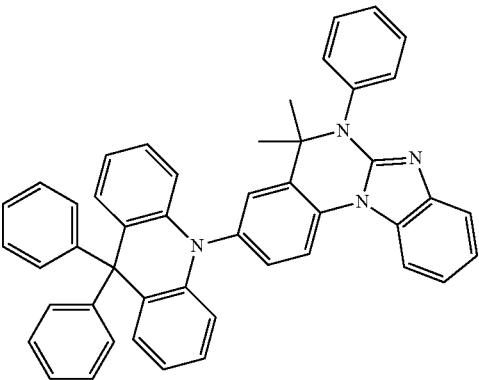

1-104
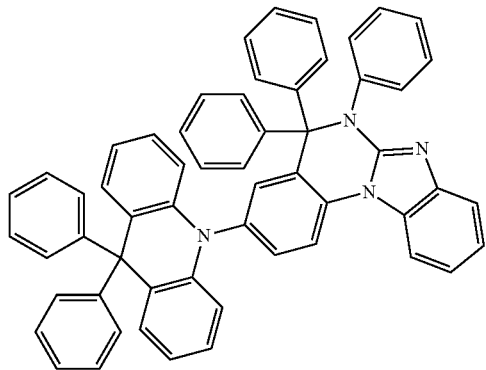
1-105
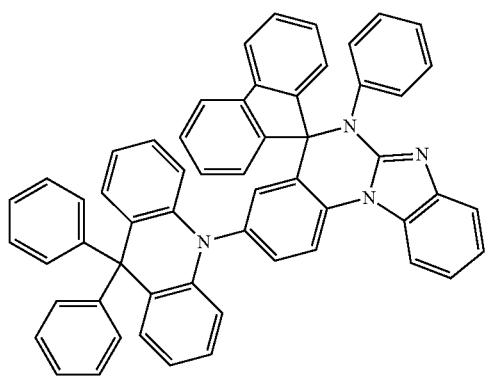
1-106
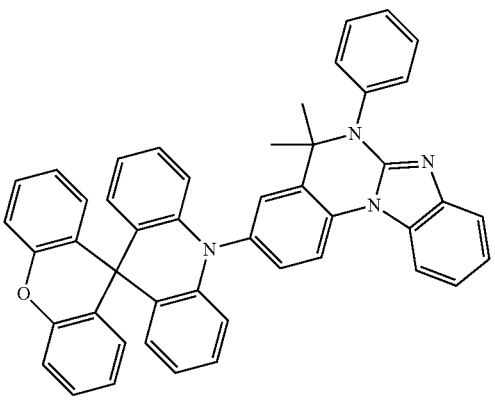
1-107
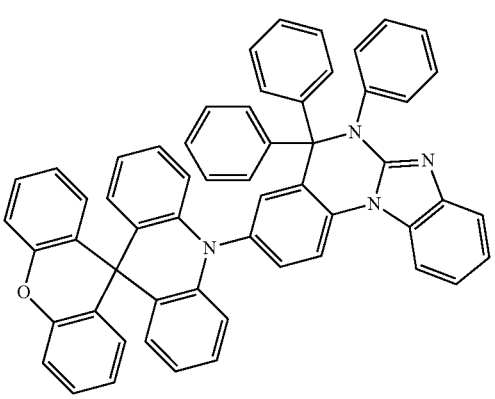
1-108
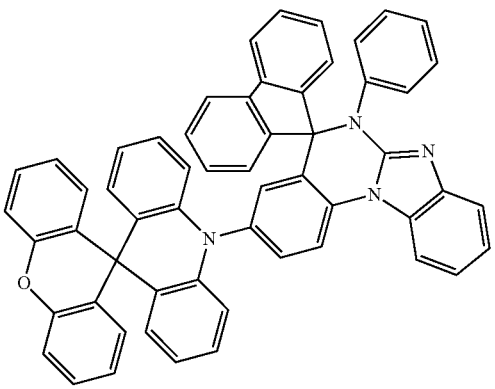
1-109
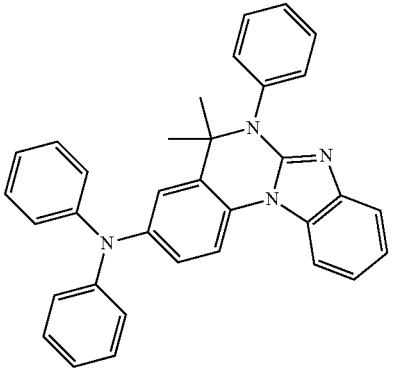
1-110
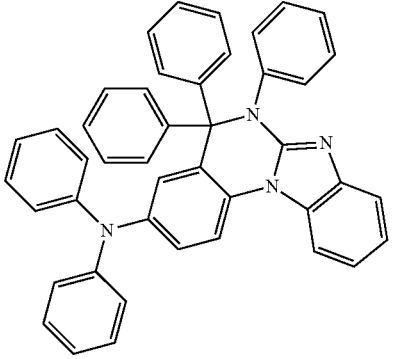
1-111
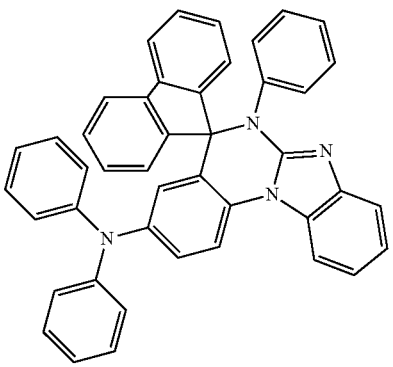

1-112
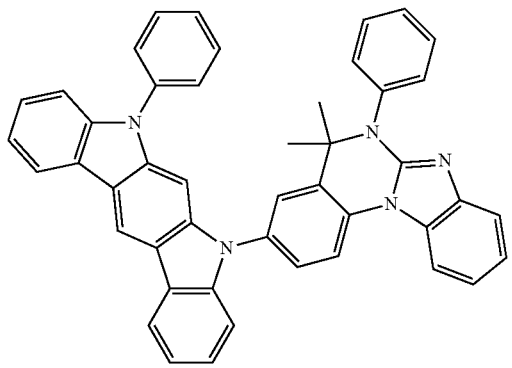
1-113
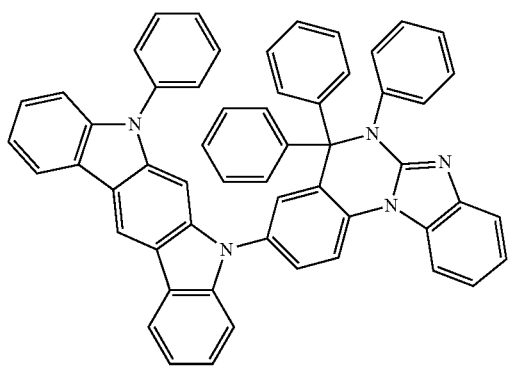
1-114
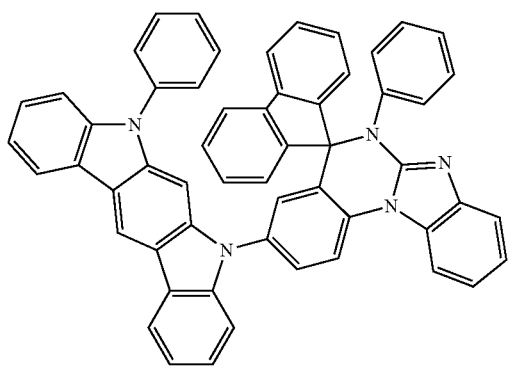
1-115
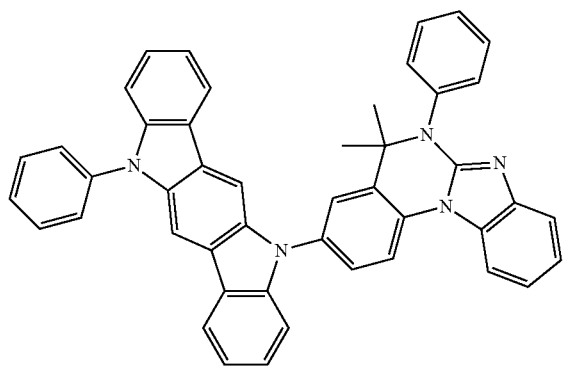
1-116
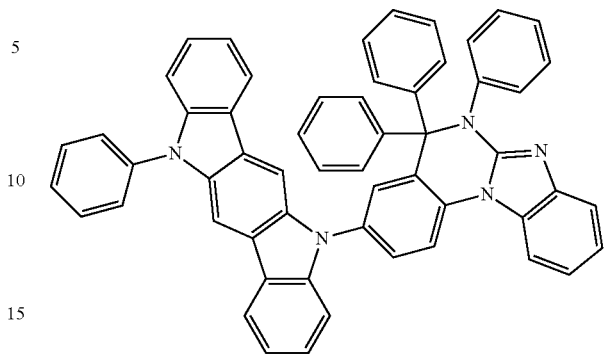
1-117
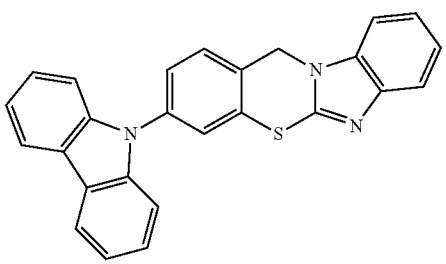
In another exemplary aspect, m is 0 (zero) and n is 1 in chemical Formula 2. Such an organic compound may comprise anyone having the following structure of Chemical Formula 3:
[Chemical Formula 3]
2-1
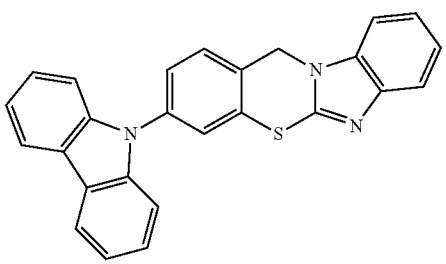
2-2
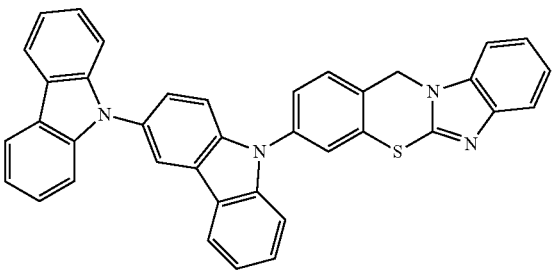

-continued
2-3
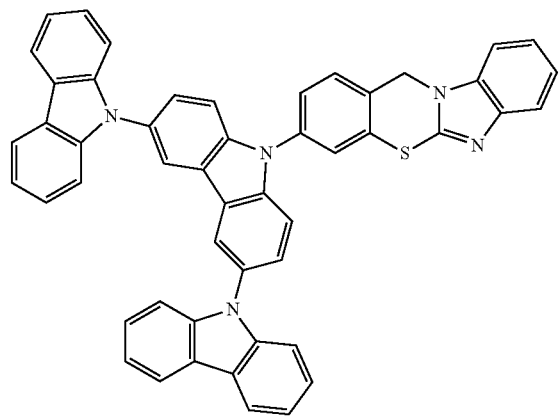
2-4
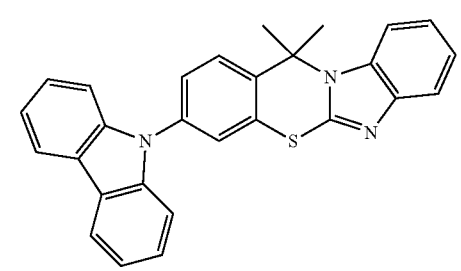
2-5
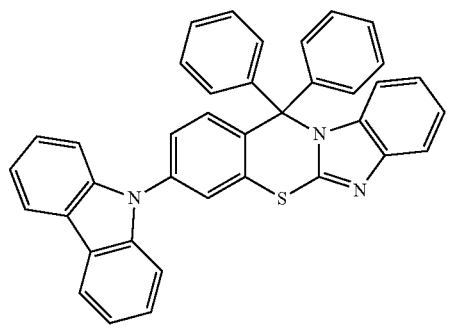
2-6
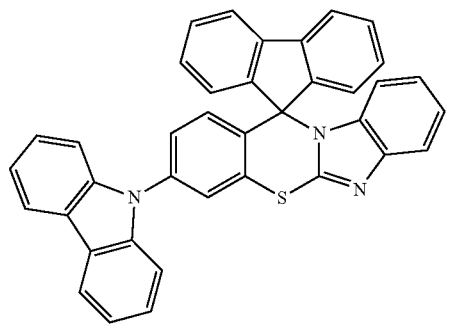
2-7
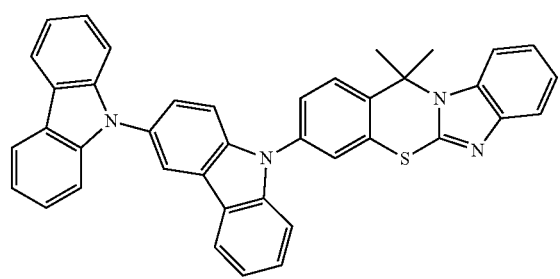
-continued
2-8
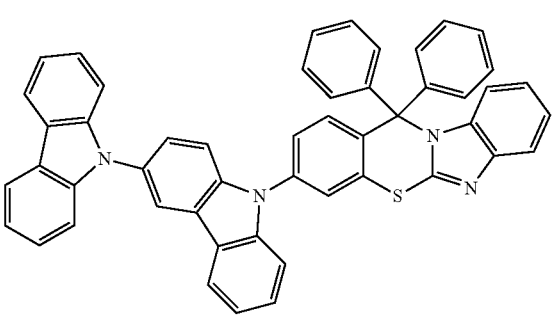
2-9
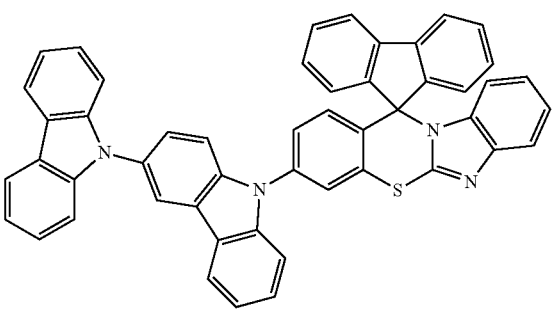
2-10
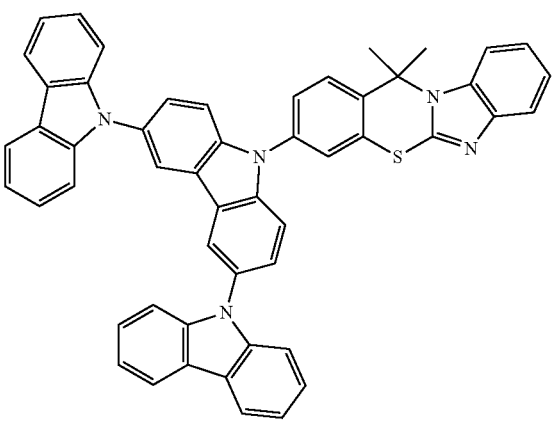
2-11
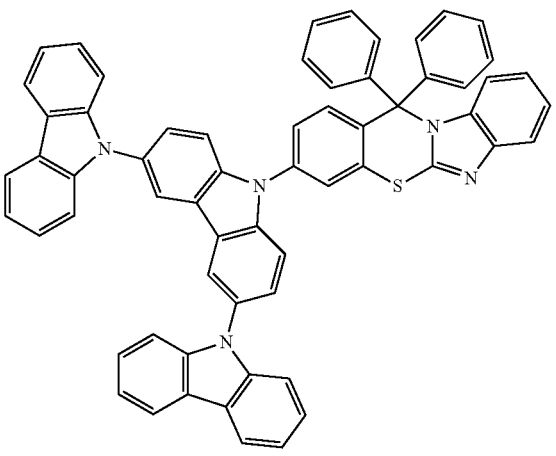

2-12
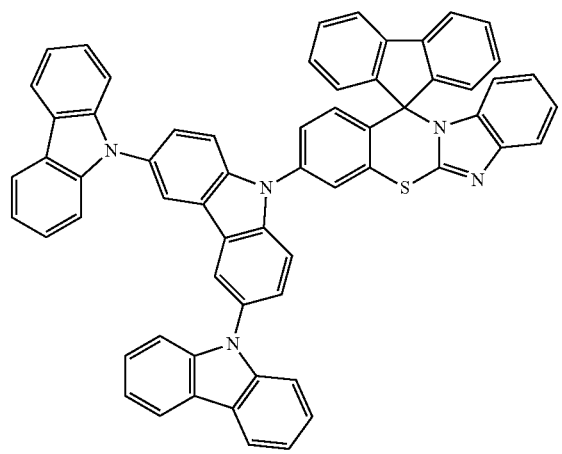
2-13
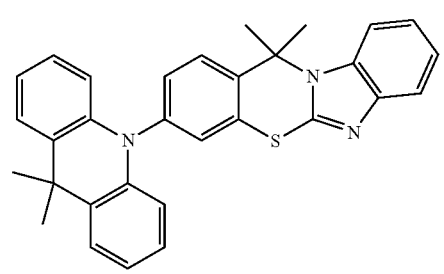
2-14
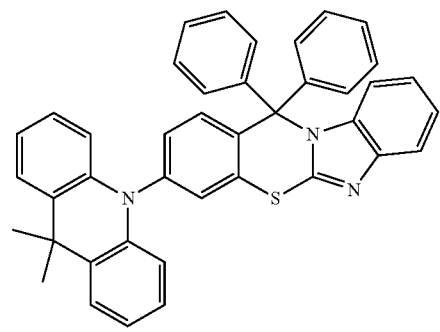
2-15
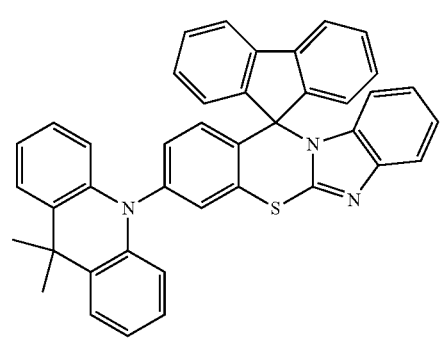
2-16
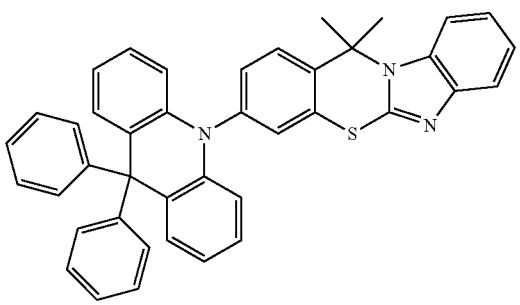
2-17
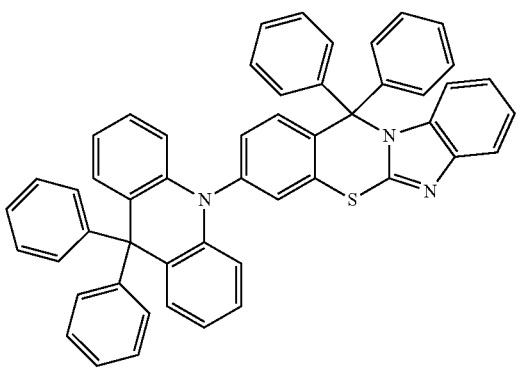
2-18
2-19
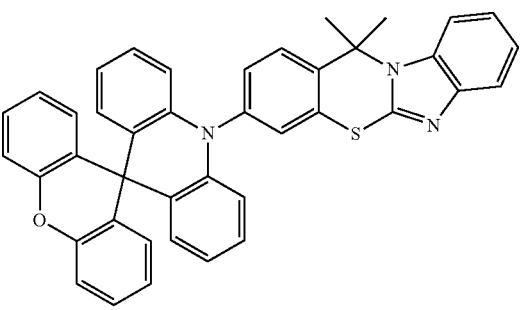

-continued
2-20
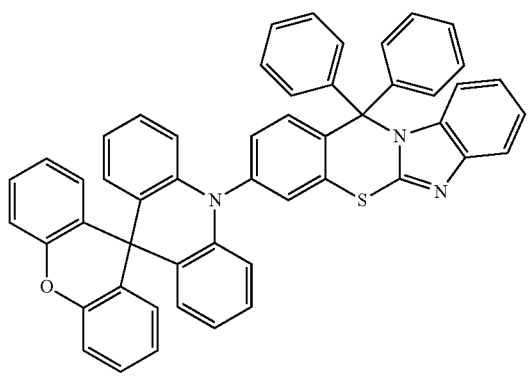
2-21
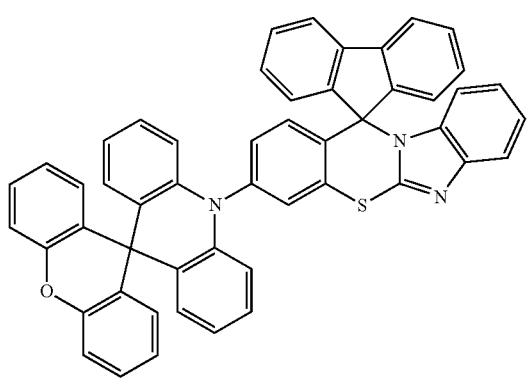
2-22
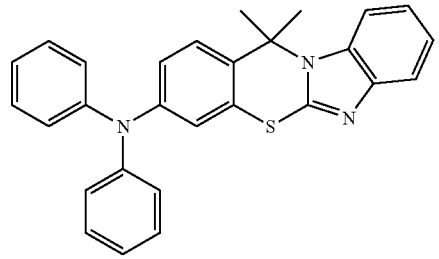
2-23
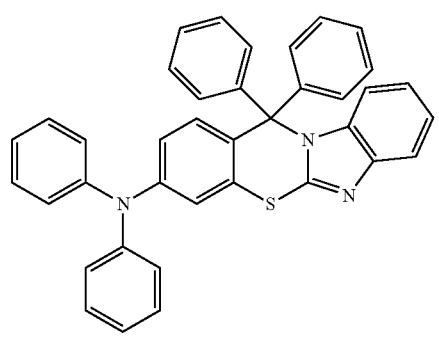
-continued
2-24
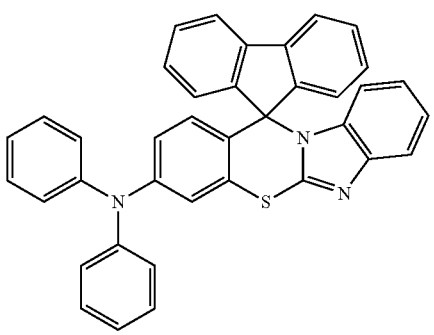
2-25
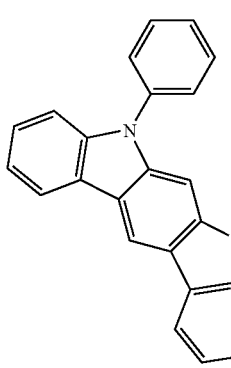
2-26
2-27
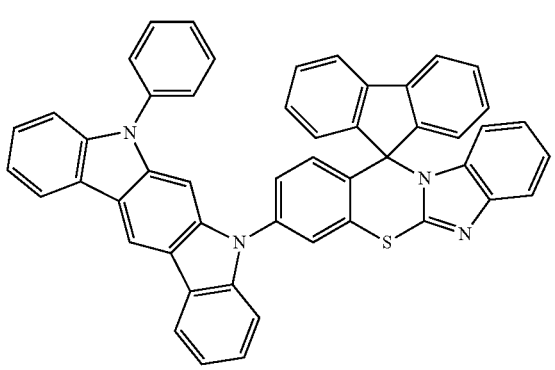

2-28
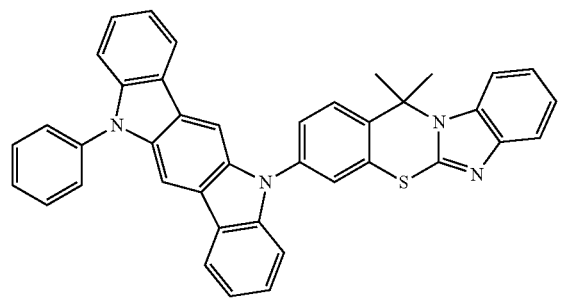
2-29
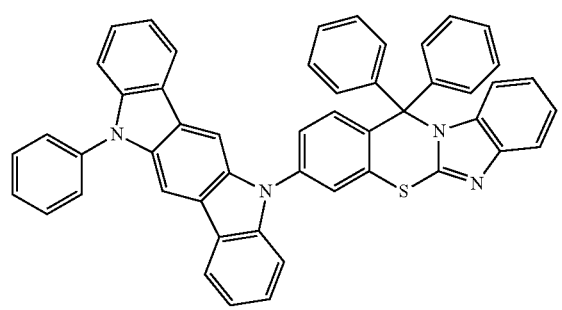
2-30
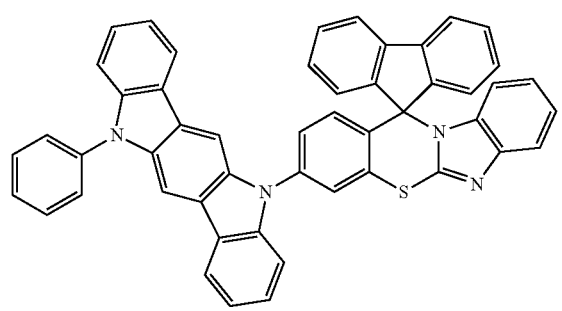
2-31
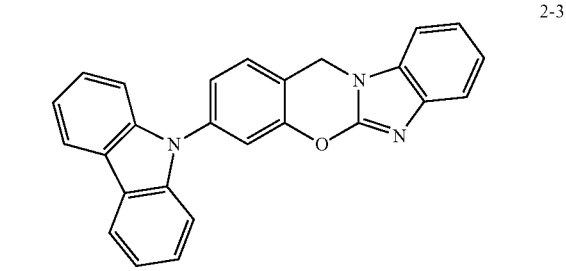
2-32
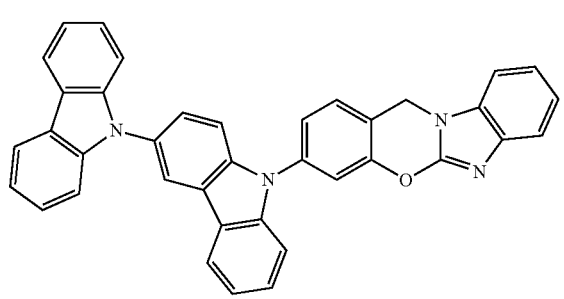
2-33
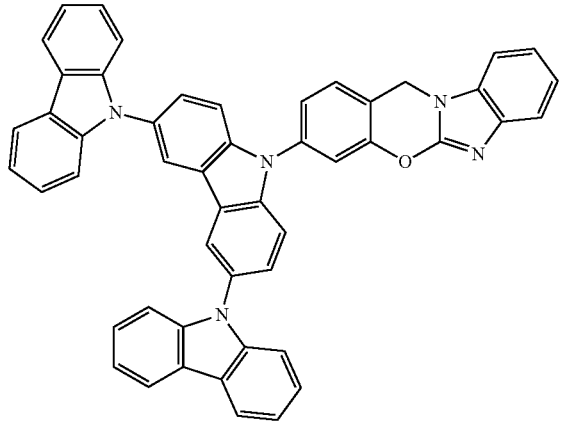
2-34
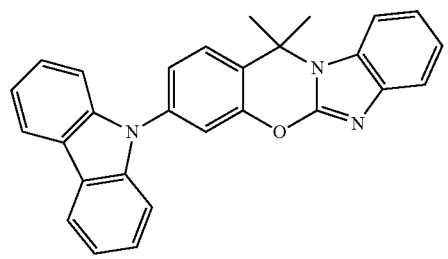
2-35
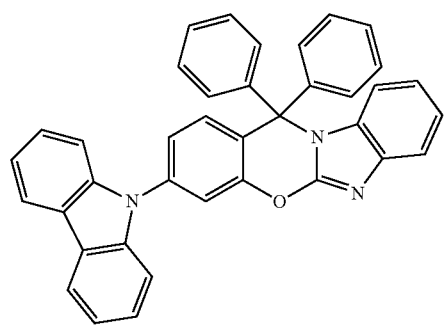
2-36
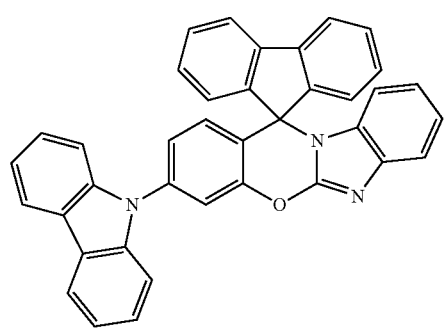

-continued
2-37
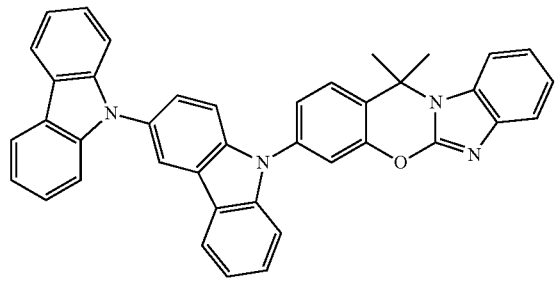
2-38
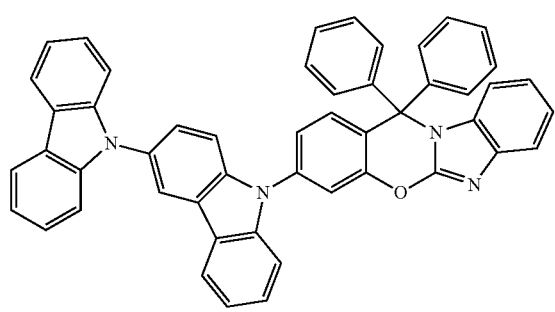
2-39
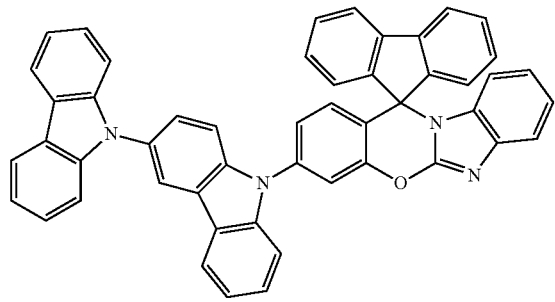
2-40
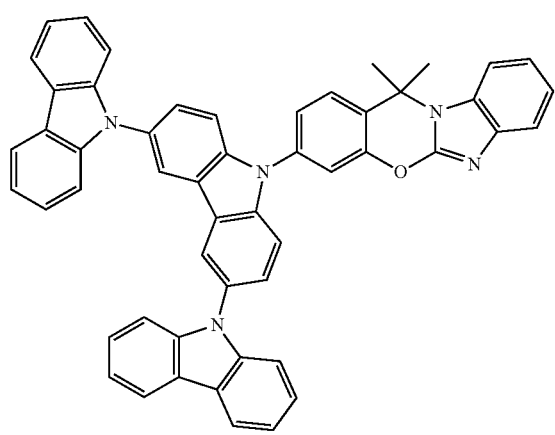
2-41
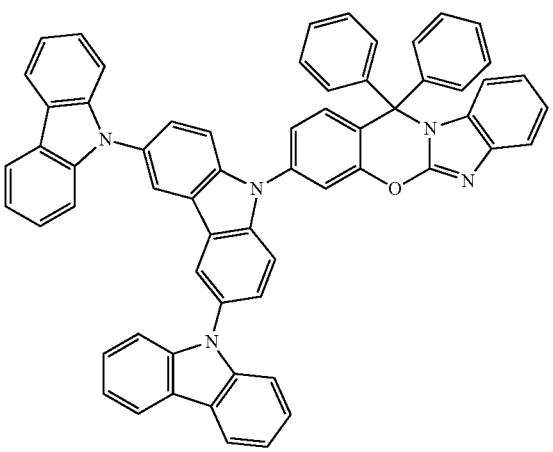
2-42
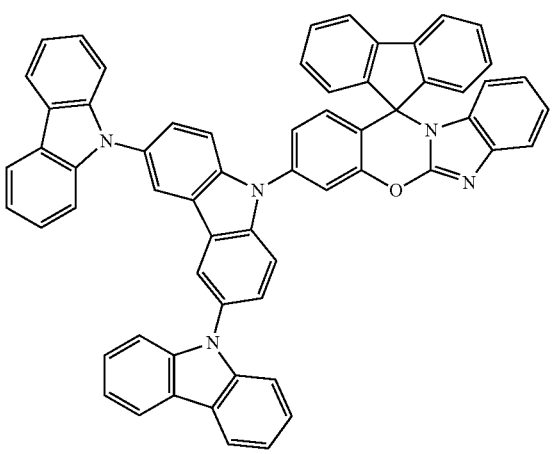
2-43
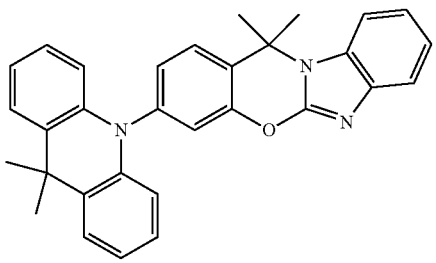
2-44
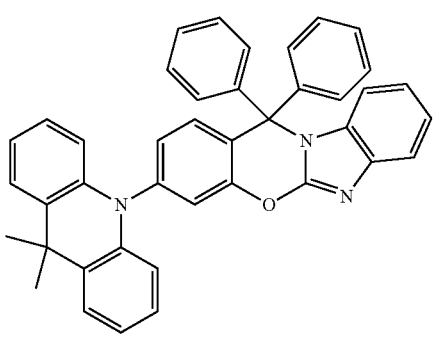

2-45
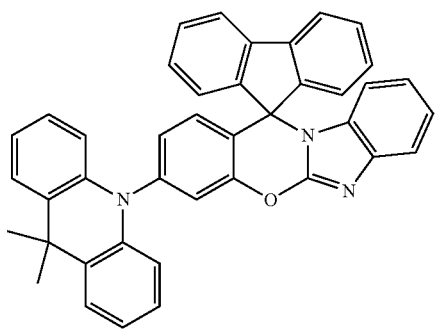
2-49
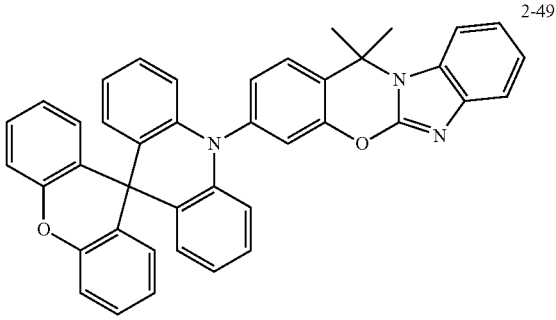
2-46
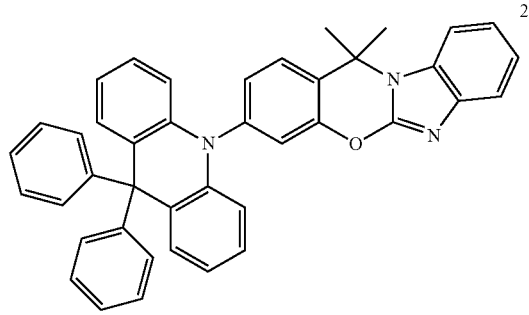
2-50
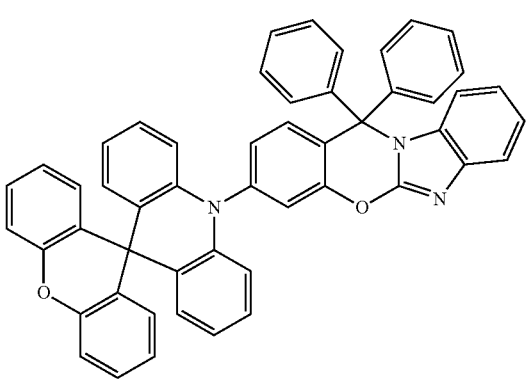
2-47
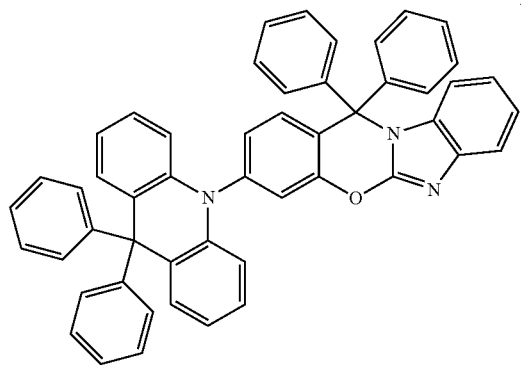
2-51
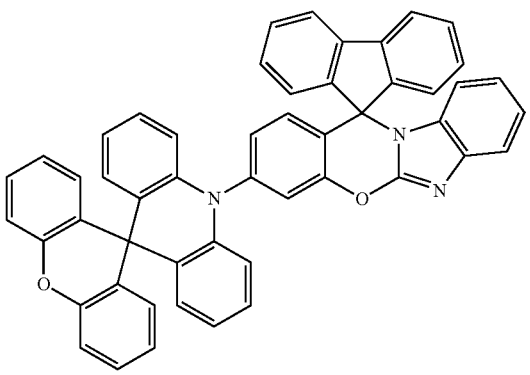
2-48
2-52
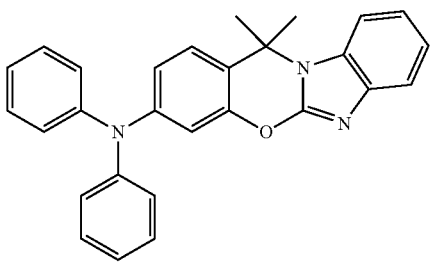

2-53
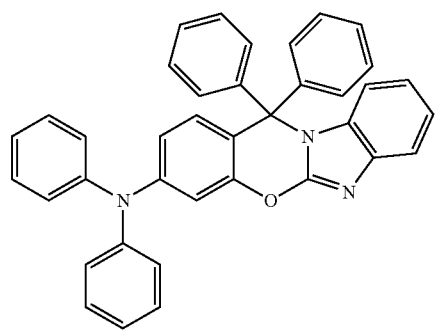
2-54
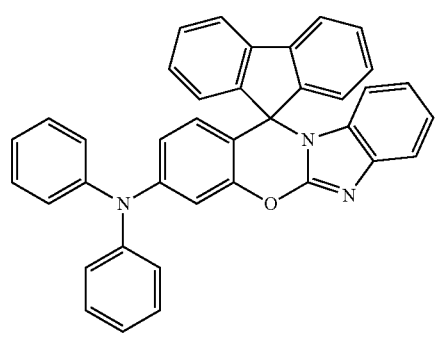
2-55
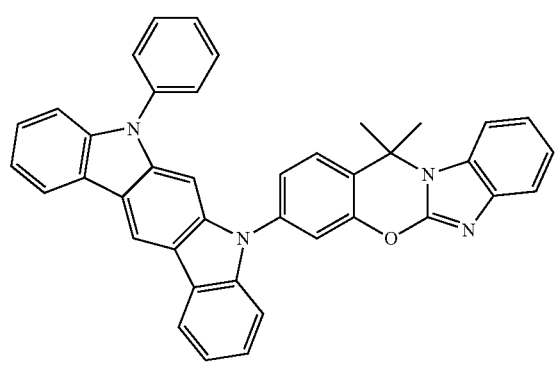
2-56
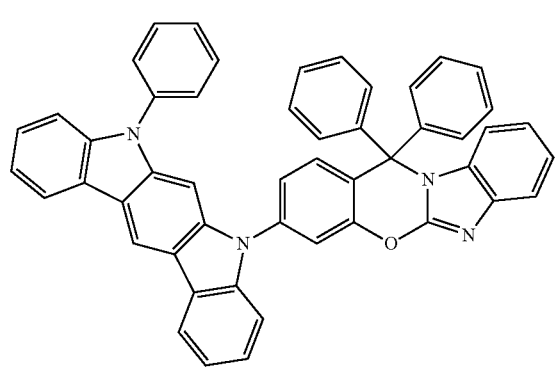
2-57
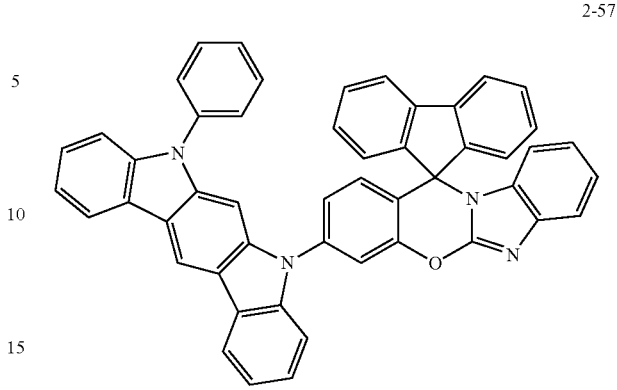
2-58
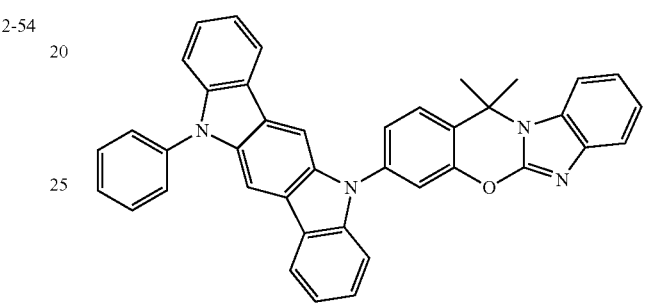
2-59
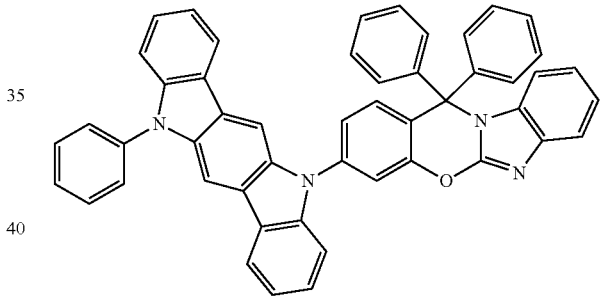
2-60
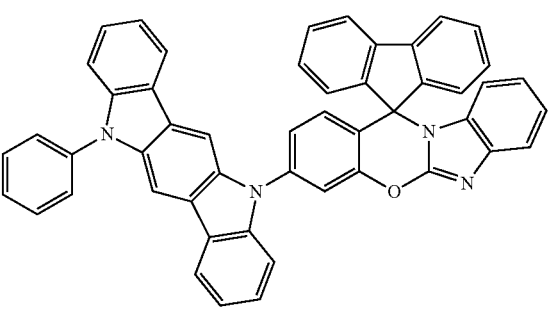
2-61
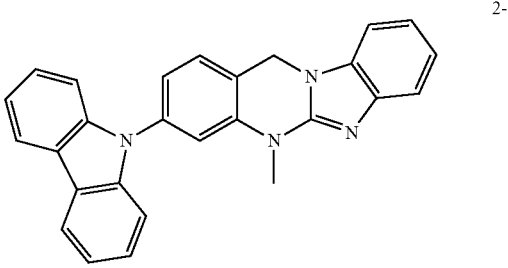

2-62
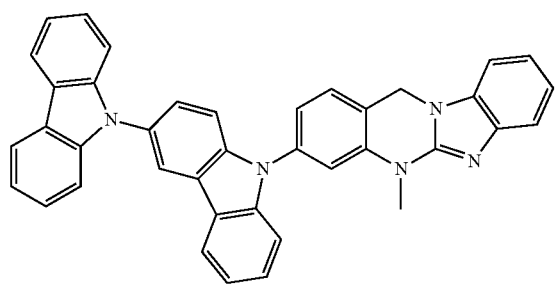
2-63
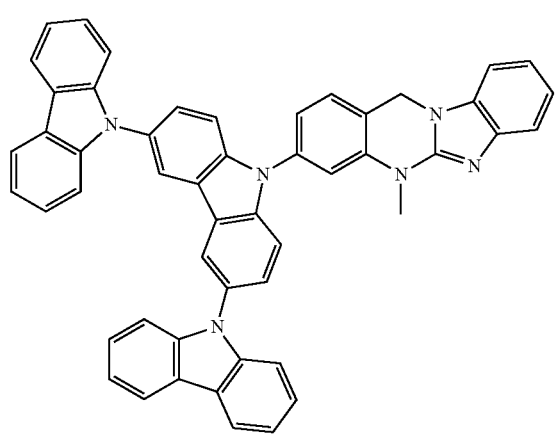
2-64
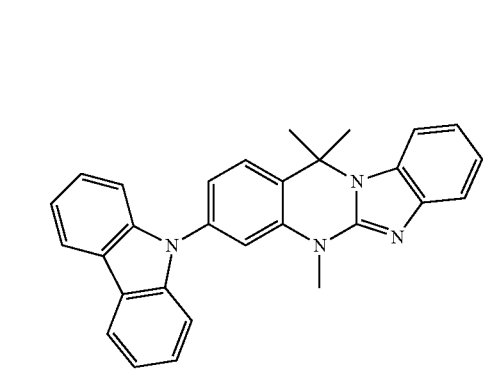
2-65
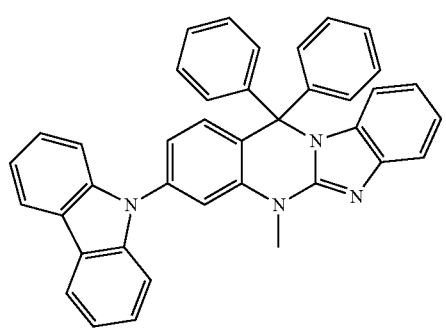
2-66
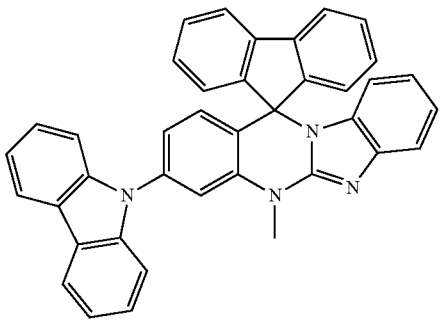
2-67
2-68
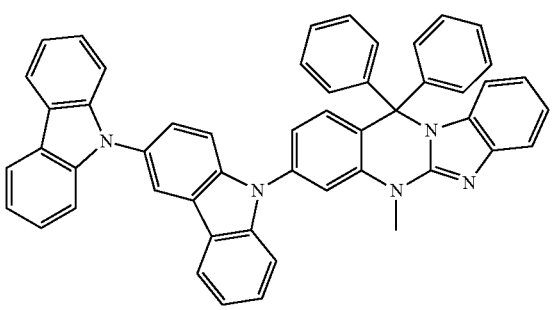
2-69
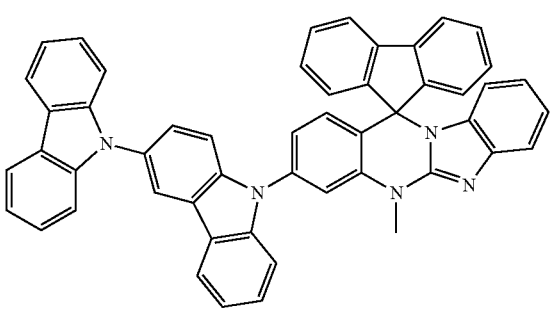

2-70
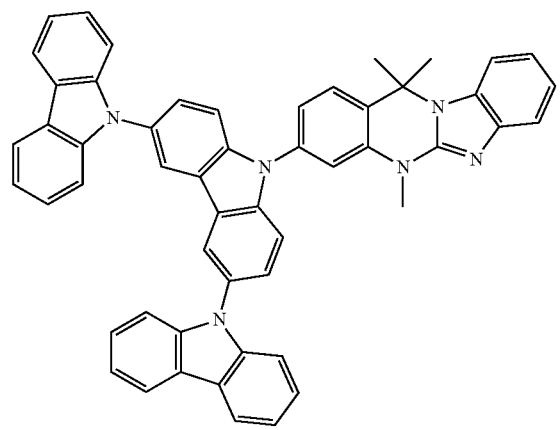
2-71
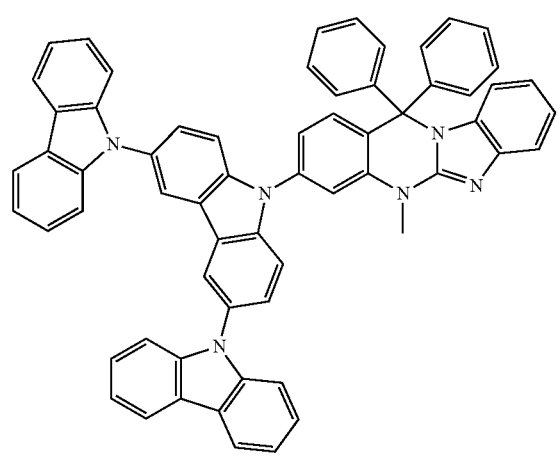
2-72
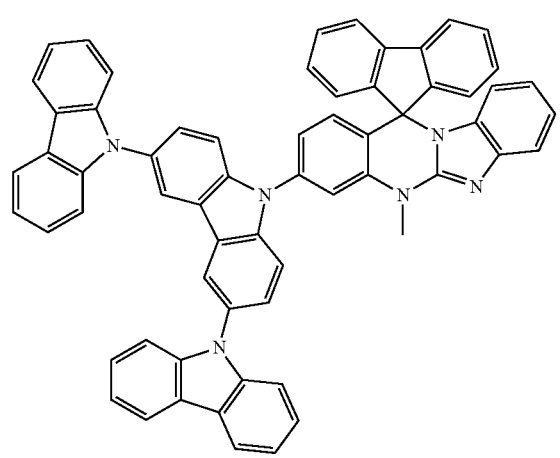
2-73
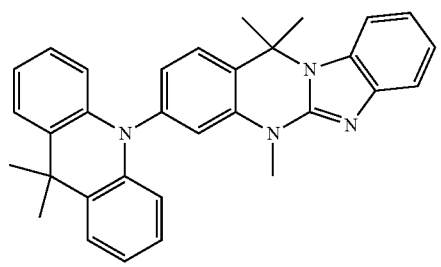
2-74
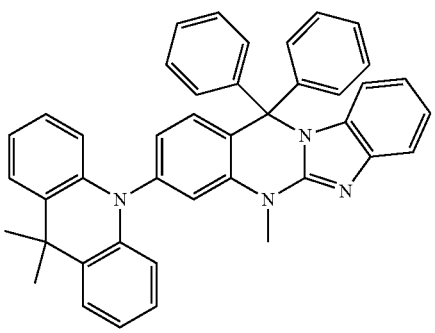
2-75
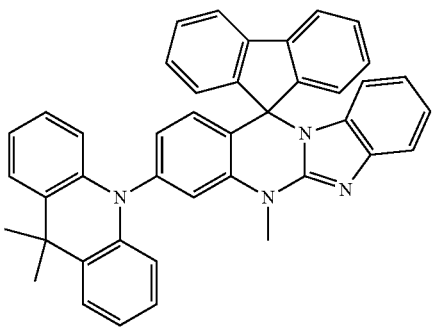
2-76
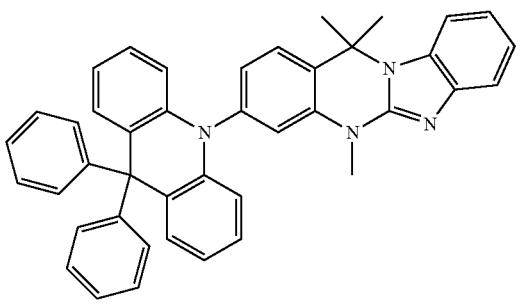
2-77
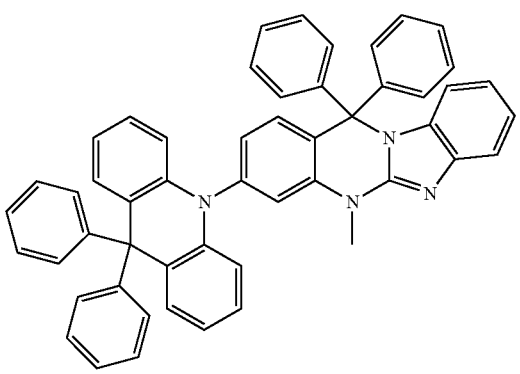

2-78
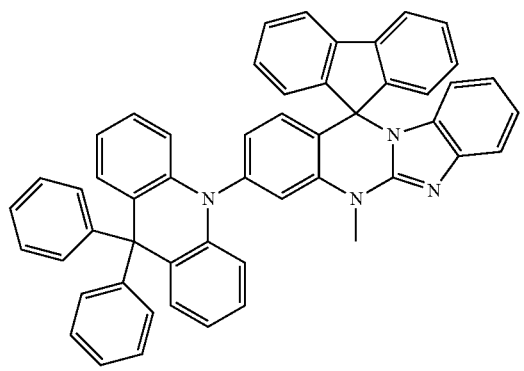
2-79
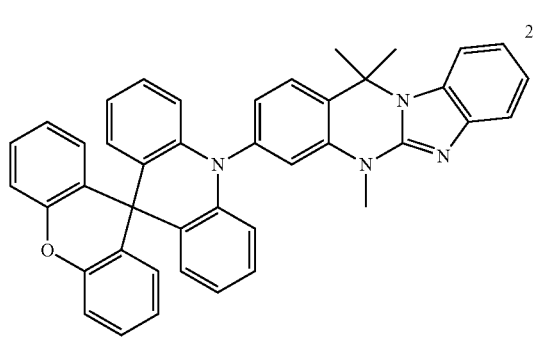
2-80
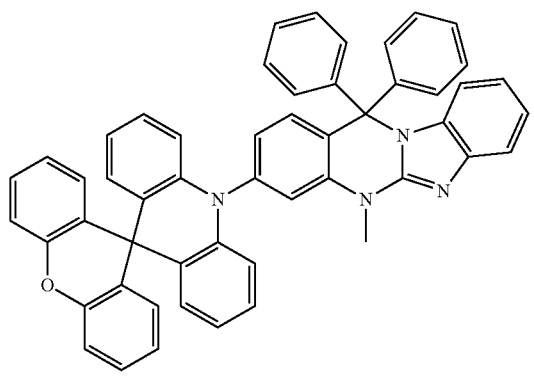
2-81
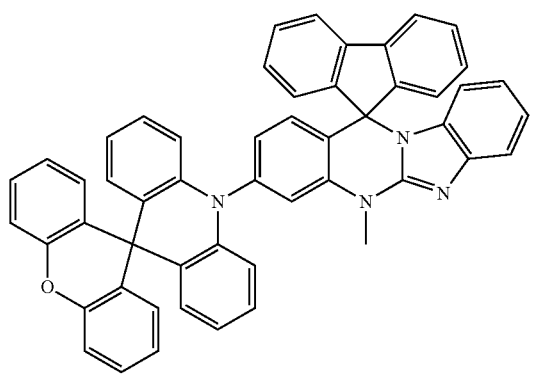
2-82
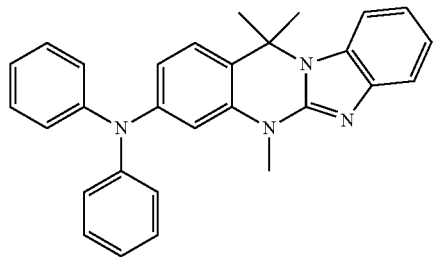
2-83
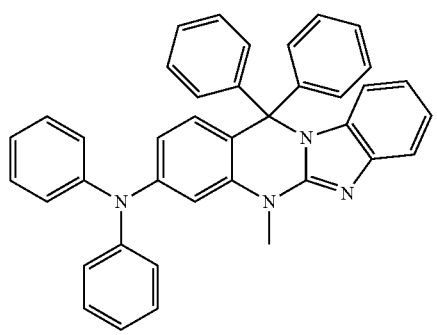
2-84
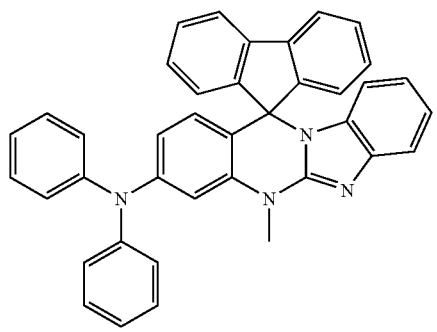
2-85
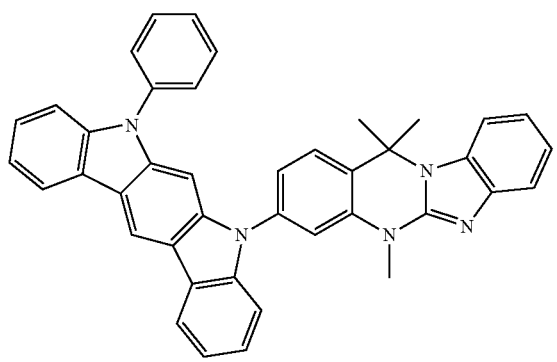

2-86
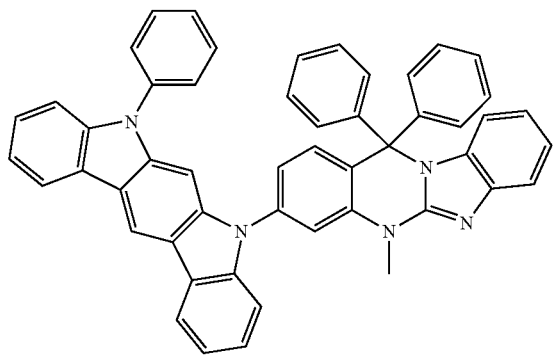
2-87
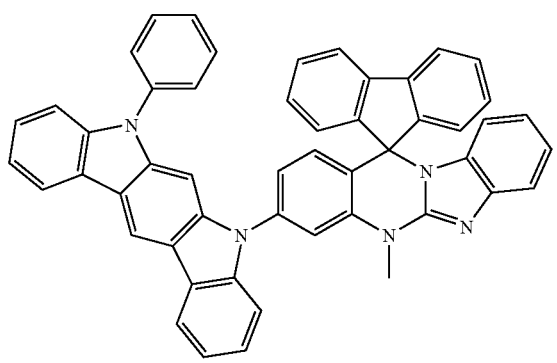
2-88
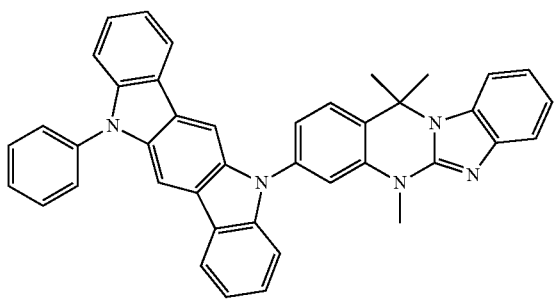
2-89
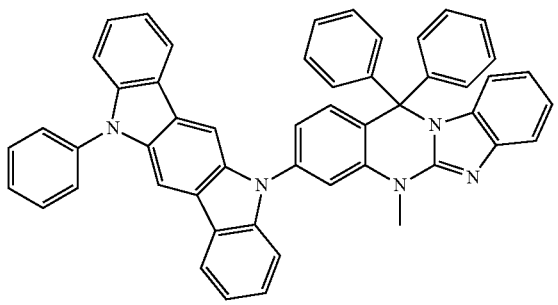
2-90
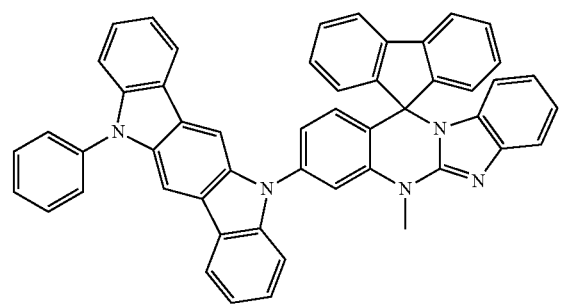
2-91
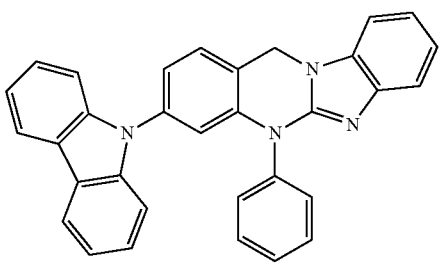
2-92
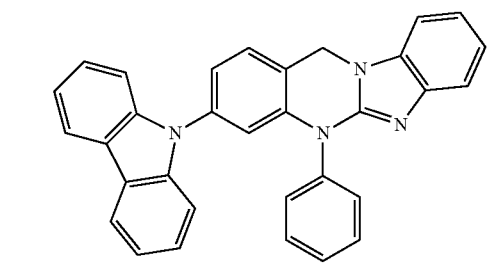
2-93
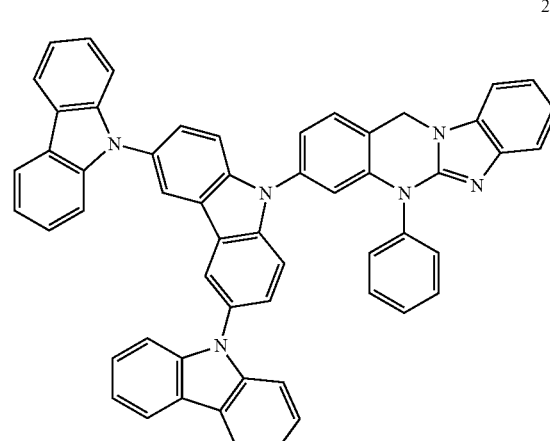
2-94
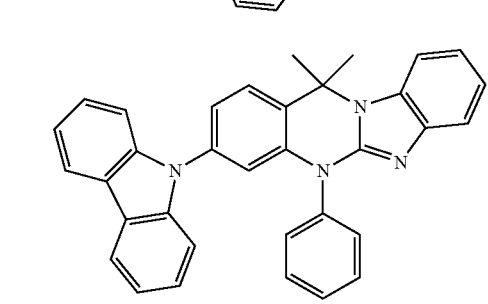

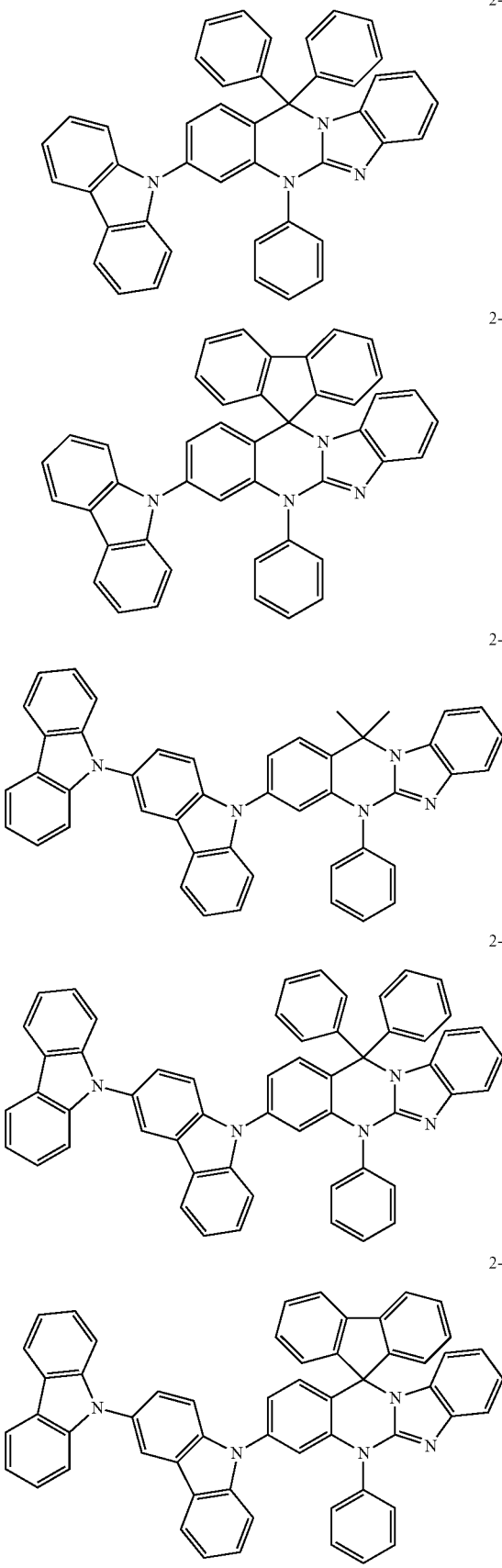
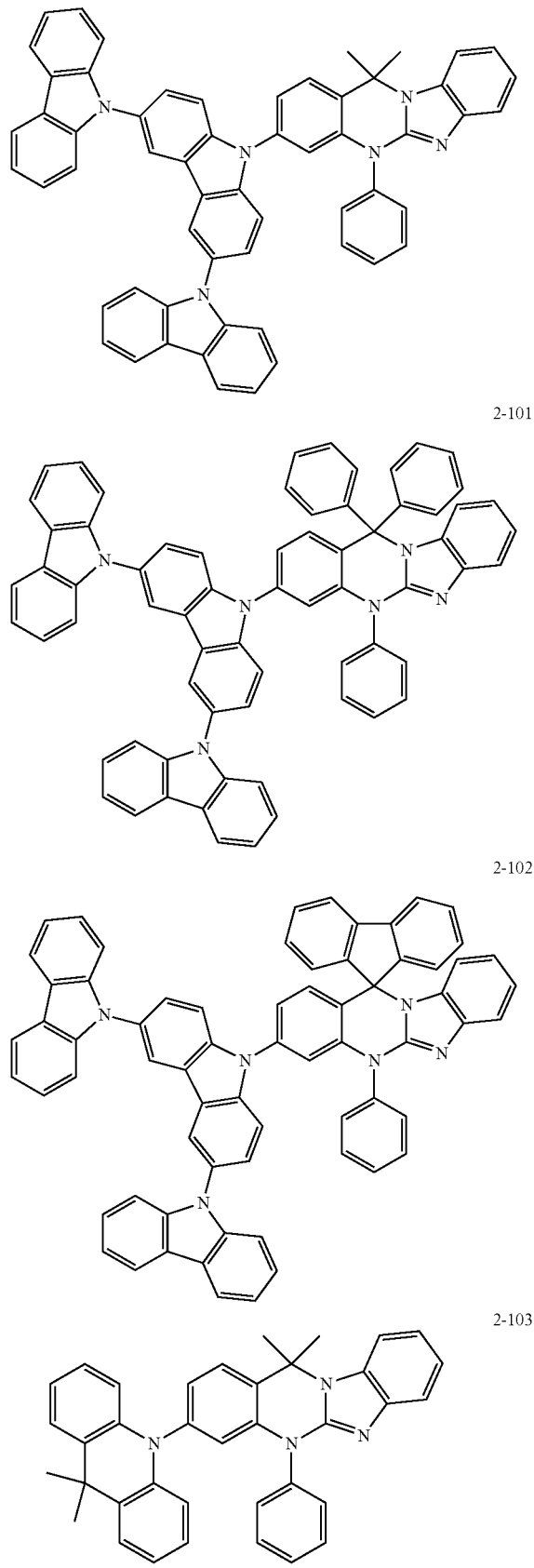

-continued
2-104
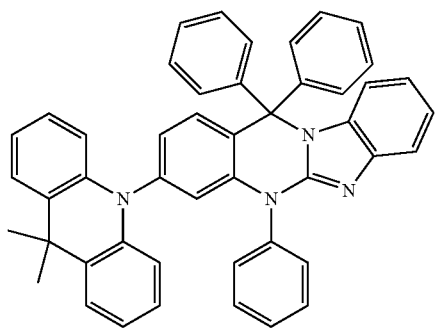
2-105
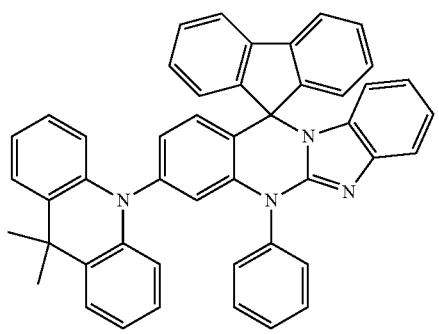
2-106
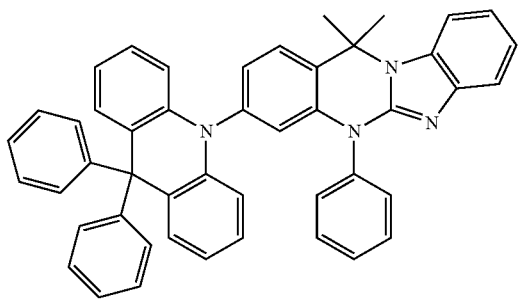
2-107
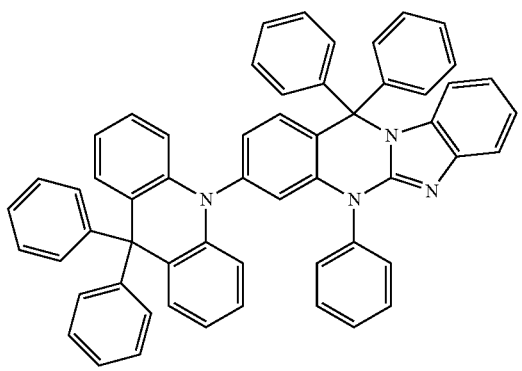
-continued
2-108
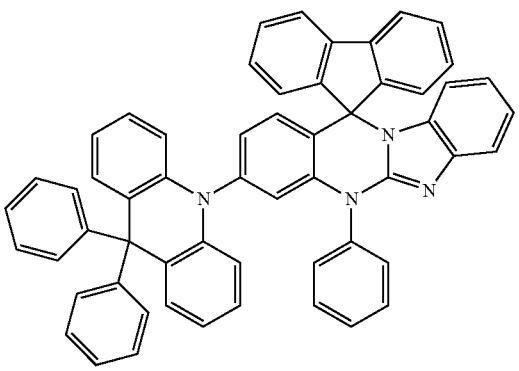
2-109
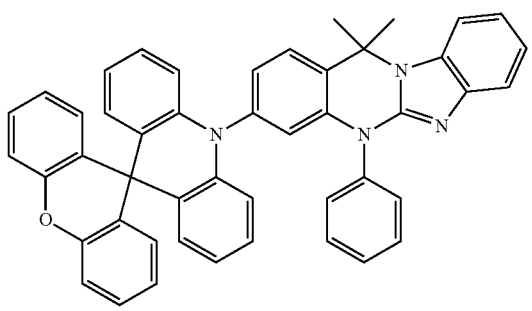
2-110
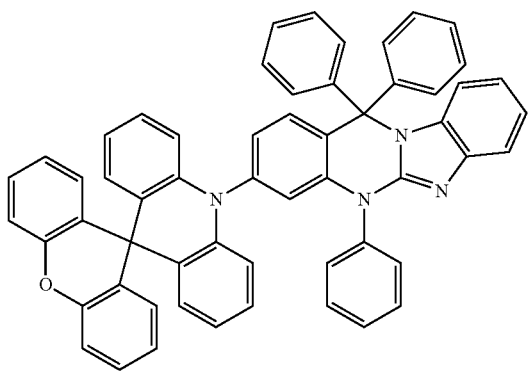
2-111
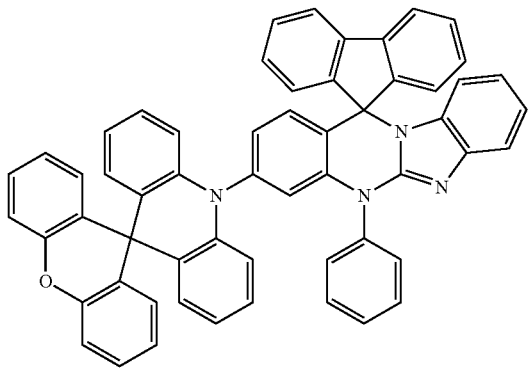

-continued
2-112
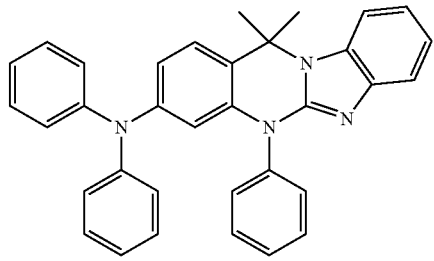
2-113
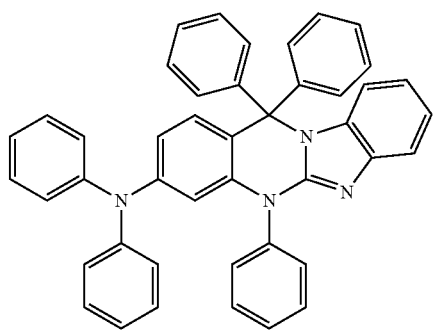
2-114
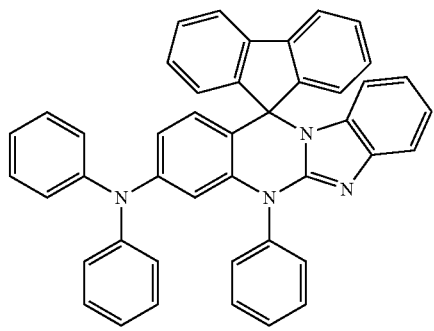
2-115
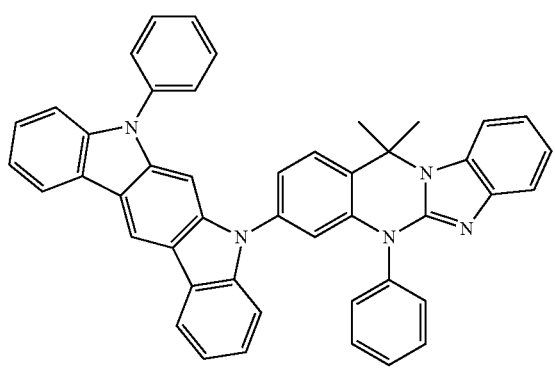
-continued
2-116
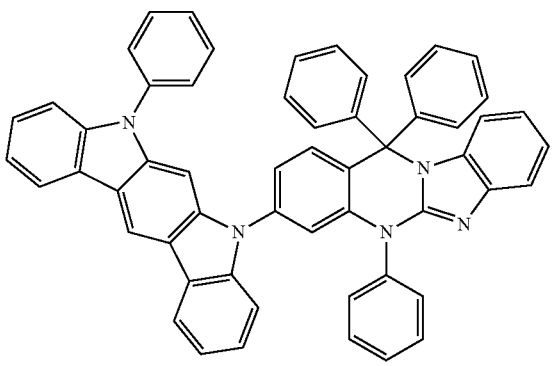
2-117
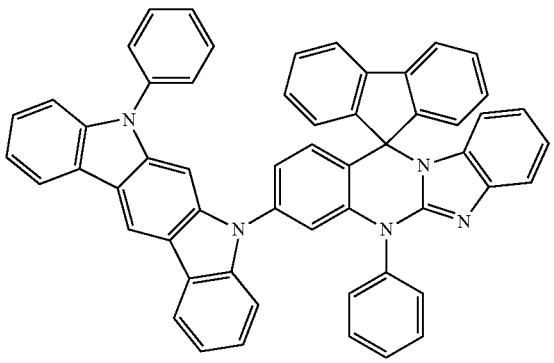
2-118
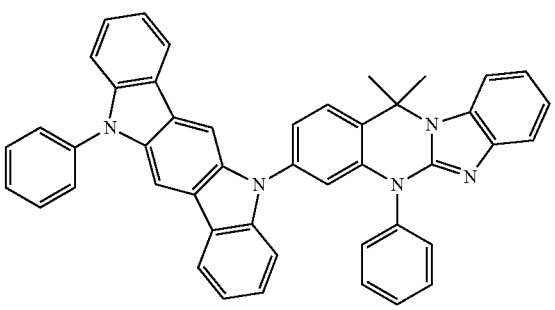
2-119
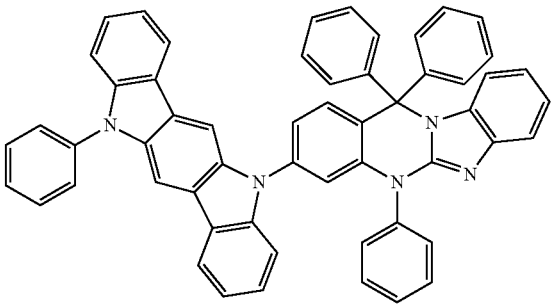

2-120

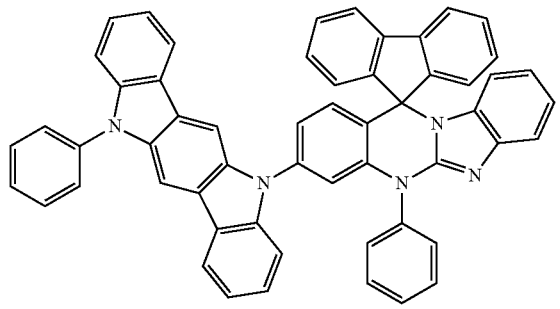

[Organic Light Emitting Device and OLED]

It is possible to realize an OLED having lower driving voltage, excellent luminous efficiency and improved luminous lifetime by applying the organic compound into an emissive layer of the OLED. The OLED of the present disclosure may be applied to an organic light emitting device such as an organic light emitting display device or an organic light emitting illumination device. An organic light emitting display device including the OLED will be explained. FIG. 1 is a schematic cross-sectional view of an organic light emitting display device 100 in accordance with an exemplary aspect of the present disclosure. All component of the organic light emitting display device in accordance with all aspects of the present disclosure are operatively couple and configured. As illustrated in FIG. 1, the organic light emitting display device 100 includes a substrate 110, a thin-film transistor Tr on the substrate 110, and an organic light emitting diode (OLED) D connected to the thin film transistor Tr.

The substrate 110 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The substrate 110, over which the thin film transistor Tr and the OLED D are arranged, form an array substrate.

A buffer layer 122 may be disposed over the substrate 110, and the thin film transistor Tr is disposed over the buffer layer 122. The buffer layer 122 may be omitted.

A semiconductor layer 120 is disposed over the buffer layer 122. In one exemplary aspect, the semiconductor layer 120 may include, but is not limited to, oxide semiconductor materials. In this case, a light-shield pattern may be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 may include, but is not limited to, polycrystalline silicon. In this case, opposite edges of the semiconductor layer 120 may be doped with impurities.

A gate insulating layer 124 formed of an insulating material is disposed on the semiconductor layer 120. The gate insulating layer 124 may include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 may be patterned identically as the gate electrode 130.

An interlayer insulating layer 132 formed of an insulating material is disposed on the gate electrode 130 with covering over an entire surface of the substrate 110. The interlayer insulating layer 132 may include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 1. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

A gate line and a data line, which cross each other to define a pixel region, and a switching element, which is connected to the gate line and the data line, may be further formed in the pixel region of FIG. 1. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter that comprises dyes or pigments for transmitting specific wavelength light of light emitted from the OLED D. For example, the color filter can transmit light of specific wavelength such as red (R), green (G), blue (B) and/or white (W). Each of red, green, and blue color filter may be formed separately in each pixel region. In this case, the organic light emitting display device 100 can implement full-color through the color filter.

For example, when the organic light emitting display device 100 is a bottom-emission type, the color filter may be disposed on the interlayer insulating layer 132 with corresponding to the OLED D. Alternatively, when the organic light emitting display device 100 is a top-emission type, the color filter may be disposed over the OLED D, that is, a second electrode 230.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it may be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 including at least one emitting part and a second electrode 230 each of which is disposed sequentially on the first electrode 210.

The first electrode 210 is disposed in each pixel region. The first electrode 210 may be an anode and include a conductive material having a relatively high work function value. For example, the first electrode 210 may include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a bottom-emission type, the first electrode 201 may have a single-layered structure of the transparent conductive material. Alternatively, when the organic light emitting display device 100 is a top-emission type, a reflective electrode or a reflective layer may be disposed under the first electrode 210. For example, the reflective electrode or the reflective layer may include, but are not limited to, silver (Ag) or aluminum-palladium-copper (APC) alloy. In the OLED D of the top-emission type, the first electrode 210 may have a triple-layered structure of ITO/Ag/ITO or ITO/APC/ITO.

In addition, a bank layer 160 is disposed on the passivation layer 150 in order to cover edges of the first electrode 210. The bank layer 160 exposes a center of the first electrode 210.

An emissive layer 220 is disposed on the first electrode 210. In one exemplary aspect, the emissive layer 220 may have a single-layered structure of an emitting material layer (EML). Alternatively, the emissive layer 220 may have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 5 7 and 9). In one aspect, the emissive layer 220 may have single emitting part. Alternatively, the emissive layer 220 may have multiple emitting parts to form a tandem structure.

The emissive layer 220 comprises anyone having the structure of Chemical Formulae 1 to 3. As an example, the organic compound having the structure of Chemical Formulae 1 to 3 may be applied into the host in the EML, or into the ETL, the HBL and the N-CGL.

The second electrode 230 is disposed over the substrate 110 above which the emissive layer 220 is disposed. The second electrode 230 may be disposed over a whole display area and may include a conductive material with a relatively low work function value compared to the first electrode 210. The second electrode 230 may be a cathode. For example, the second electrode 230 may include, but is not limited to, aluminum (Al), magnesium (Mg), calcium (Ca), silver (Ag), alloy thereof or combination thereof such as aluminum-magnesium alloy (Al—Mg). When the organic light emitting display device 100 is a top-emission type, the second electrode 230 is thin so as to have light-transmissive (semi-transmissive) property.

In addition, an encapsulation film 170 may be disposed over the second electrode 230 in order to prevent outer moisture from penetrating into the OLED D. The encapsulation film 170 may have, but is not limited to, a laminated structure of a first inorganic insulating film 172, an organic insulating film 174 and a second inorganic insulating film 176.

Moreover, the organic light emitting display device 100 may have a polarizer in order to decrease external light reflection. For example, the polarizer may be a circular polarizer. When the organic light emitting display device 100 is a bottom-emission type, the polarizer may be disposed under the substrate 100. Alternatively, when the organic light emitting display device 100 is a top-emission type, the polarizer may be disposed over the encapsulation film 170. In addition, a cover window may be attached to the encapsulation film 170 or the polarizer. In this case, the substrate 110 and the cover window may have a flexible property, thus the organic light emitting display device 100 may be a flexible display device.

As described above, the OLED D includes anyone having the structure of Chemical Formulae 1 to 3 in the emissive layer 220. The organic compound has excellent thermal stability and luminous properties, thus the OLED D can improve its luminous efficiency, lower its driving voltage and power consumption and can increase its luminous lifetime by applying the organic compound into the OLED D.

Figure 2:
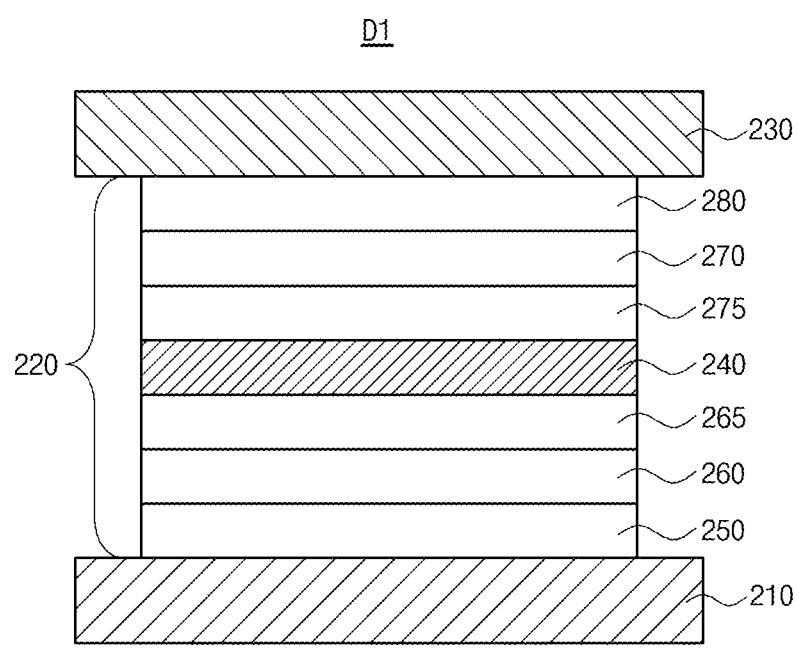
FIG. 2 is a schematic cross-sectional view illustrating an OLED in accordance with an exemplary aspect of the present disclosure.

Now, we will describe the OLED in more detail. FIG. 2 is a schematic cross-sectional view illustrating an OLED in accordance with an exemplary aspect of the present disclosure. As illustrated in FIG. 2, the OLED D1 includes first and second electrodes 210 and 230 facing each other and an emissive layer 220 with single emitting part disposed between the first and second electrodes 210 and 230. The organic light emitting display device 100 includes a red pixel region, a green pixel region and a blue pixel region, and the OLED D1 may be disposed in any pixel region of the red, green and blue pixel regions.

In one exemplary aspect, the emissive layer 220 comprises an EML 240 disposed between the first and second electrodes 210 and 230. Also, the emissive layer 220 may comprise at least one of a HTL 260 disposed between the first electrode 210 and the EML 240 and an ETL 270 disposed between the second electrode 230 and the EML 240. Also, the emissive layer 220 may further comprise at least one of a HIL 250 disposed between the first electrode 210 and the HTL 260 and an EIL 280 disposed between the second electrode 230 and the ETL 270.

Alternatively, the emissive layer 220 may further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 may be an anode that provides a hole into the EML 240. The first electrode 210 may include, but is not limited to, a conductive material having a relatively high work function value, for example, a transparent conductive oxide (TCO). In an exemplary aspect, the first electrode 210 may include, but is not limited to, ITO, IZO, ITZO, SnO, ZnO, ICO, AZO, and the like.

The second electrode 230 may be a cathode that provides an electron into the EML 240. The second electrode 230 may include, but is not limited to, a conductive material having a relatively low work function value, i.e., a highly reflective material such as Al, Mg, Ca, Ag, alloy thereof, combination thereof, and the like.

In this aspect, the EML 240 may comprise a first compound (Compound 1, Host) and a second compound (Compound 2) TD. For example, the first compound may be a (first) host and the second compound TD may be a dopant such as fluorescent material, phosphorescent material and a delayed fluorescent material. Hereinafter, the EML 240 where the second compound is the delayed fluorescent material will be explained. As an example, the organic compound having the structure of Chemical Formulae 1 to 3 may be used as the host. For example, the EML 240 may emit red (R), green (G) or blue (B) light.

The HIL 250 is disposed between the first electrode 210 and the HTL 260 and improves an interface property between the inorganic first electrode 210 and the organic HTL 260. In one exemplary aspect, the HIL 250 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrite (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 250 may be omitted in compliance with a structure of the OLED D1.

The HTL 260 is disposed adjacently to the EML 240 between the first electrode 210 and the EML 240. In one exemplary aspect, the HTL 260 may include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis (phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), 3,5-di(9H-carbazol-9-yl)-N,N-diphenylamine (DCDPA), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The ETL 270 and the EIL 280 may be laminated sequentially between the EML 240 and the second electrode 230. The ETL 270 includes a material having high electron mobility so as to provide electrons stably with the EML 240 by fast electron transportation.

In one exemplary aspect, the ETL 270 may comprise, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 may comprise, but is not limited to, tris-(8-hydroxyquinoline aluminum (Alq$_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ) and/or diphenyl-4-triphenysilyl-phenylphosphine oxide (TSPO1).

In another exemplary aspect, the ETL 270 may comprise anyone having the structure of Chemical Formulae 1 to 3. The organic compound has an excellent affinity to electrons. In this case, the ETL 270 may comprise only the organic compound having the structure of Chemical Formulae 1 to 3, or comprise the above-described electron transporting materials mixed or doped with the organic compound.

The EIL 280 is disposed between the second electrode 230 and the ETL 270, and can improve physical properties of the second electrode 230 and therefore, can enhance the lifetime of the OLED D1. In one exemplary aspect, the EIL 280 may comprise, but is not limited to, an alkali metal halide or an alkaline earth metal halide such as LiF, CsF, NaF, BaF$_2$ and the like, and/or an organic metal compound such as lithium quinolate, lithium benzoate, sodium stearate, and the like.

When holes are transferred to the second electrode 230 via the EML 240 and/or electrons are transferred to the first electrode 210 via the EML 240, the OLED D1 may have short lifetime and reduced luminous efficiency. In order to prevent these phenomena, the OLED D1 in accordance with this aspect of the present disclosure may have at least one exciton blocking layer adjacent to the EML 240.

For example, the OLED D1 in the exemplary aspect includes the EBL 265 between the HTL 260 and the EML 240 so as to control and prevent electron transfers. In one exemplary aspect, the EBL 265 may comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, 1,3-bis(carbazol-9-yl)benzene (mCP), 3,3'-bis(N-carbazolyl)-1,1'-biphenyl (mCBP), CuPc, N,N'-bis[4-(bis(3-methylphenyl)amino)phenyl]-N,N'-dipheny-[1,1'-biphenyl]-4,4'-diamine (DNTPD), TDAPB, DCDPA and/or 2,8-bis(9-phenyl-9H-carbazol-3-yl)dibenzo[b,d]thiophene.

In addition, the OLED D1 may further include the HBL 275 as a second exciton blocking layer between the EML 240 and the ETL 270 so that holes cannot be transferred from the EML 240 to the ETL 270. In one exemplary aspect, the HBL 275 may comprise, but is not limited to, oxadiazole-based compounds, triazole-based compounds, phenanthroline-based compounds, benzoxazole-based compounds, benzothiazole-based compounds, benzimidazole-based compounds, and triazine-based compounds each of which can be used in the ETL 270.

For example, the HBL 275 may comprise a compound having a relatively low HOMO energy level compared to the luminescent materials in EML 240. The HBL 275 may comprise, but is not limited to, mCBP, BCP, BAlq, Alq$_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole, TSPO1 and combination thereof.

In another exemplary aspect, the HBL 275 may comprise anyone having the structure of Chemical Formulae 1 to 3. The organic compound has deep HOMO energy level for blocking holes. In this case, the HBL 275 may comprise only the organic compound having the structure of Chemical Formulae 1 to 3, or comprise the above-described hole blocking materials mixed or doped with the organic compound.

As described above, the EML 240 in the first aspect comprises the first compound that is anyone having the structure of Chemical Formulae 1 to 3 and the second compound that may have the delayed fluorescent property.

In the prior art, the EML 240 has used a p-type host that has excellent affinity to holes. When the p-type host is applied into the EML 240, the recombination zone among holes and electrons is formed at an interface between the EML 240 and the HBL 275 because the p-type host prefers holes to electrons. In this case, some of charges injected into the EML 240 cannot recombine with opposite charges to be quenched without being involved in the luminescence process, and therefore, the luminous efficiency is deteriorated.

On the contrary, the organic compound having the structure of Chemical Formulae 1 to 3 is the bipolar compound. When the organic compound is applied into the host in the EML 240, the recombination zone among the holes and electrons are distributed uniformly in the whole area of the EML 240 including an interface between the EML 240 and the EBL 265. In other words, when applying the organic compound in the EML 240, most holes and electrons injected into the EML 240 are recombined without quenching, the OLED D1 can maximize its luminous efficiency.

External quantum efficiency (EQE, $\eta_{ext}$) of the luminous material applied into the EML is determined by four factors such as a singlet/triplet ratio, a charge balance factor, a radiative efficiency and an out-coupling efficiency. Since the fluorescent material uses only singlet exciton in the luminescence process, the maximum luminous efficiency of the OLED using the conventional fluorescent material is only about 5%.

On the other hand, phosphorescent materials have a luminescent mechanism that converts both the singlet and triplet excitons to light. Phosphorescent materials convert singlet exciton into triplet exciton through intersystem crossing (ISC). Therefore, when using phosphorescent materials using both singlet exciton and triplet exciton, it is possible to improve the low luminous efficiency of the fluorescent materials. However, blue phosphorescent materials have too low color purity and too short lifetime to be applied into commercial display devices. Thus, it is necessary to improve the disadvantages of the phosphorescent materials and the low luminous efficiency of the blue luminescent materials.

Figure 3:
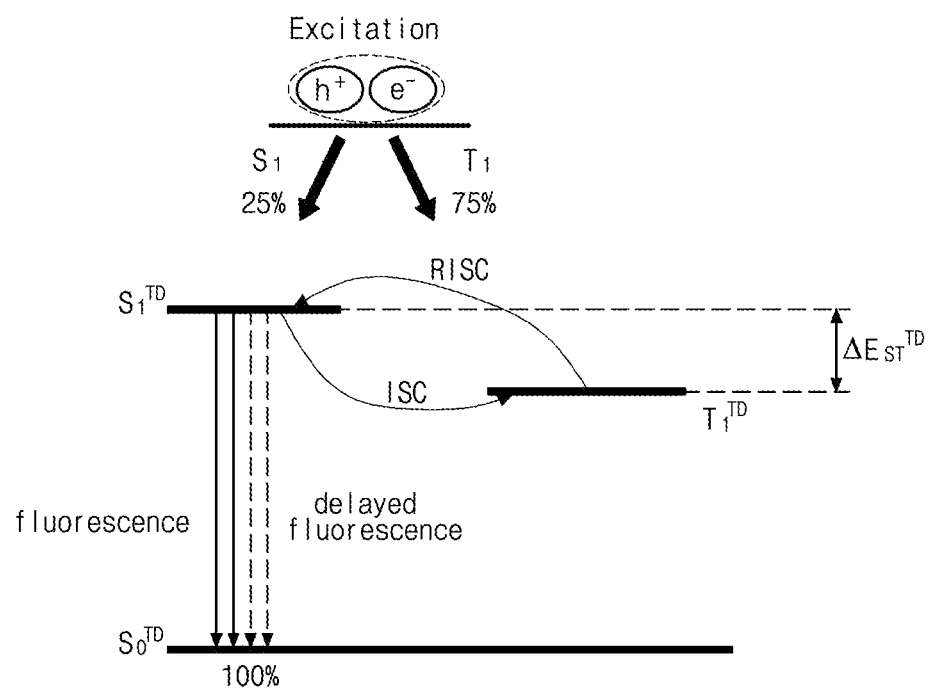
FIG. 3 is a schematic diagram illustrating a luminous mechanism of a delayed fluorescent material.

The delayed fluorescent material, which can solve the problems accompanied by the conventional art fluorescent and/or phosphorescent materials, has been developed. Representative delayed fluorescent material is a thermally-activated delayed fluorescent (TADF) material. FIG. 3 is a schematic diagram illustrating a luminous mechanism of delayed fluorescent material in the EML.

As illustrated in FIG. 3, the excitons of singlet energy level $S_1^{TD}$ as well as the excitons of triplet energy level $T_1^{TD}$ in the delayed fluorescent material TD can be transferred to an intermediate energy level state, i.e. ICT state, and then the intermediate stated excitons can be shifted to the ground state ($S_0^{TD}$; $S_1^{TD} \rightarrow ICT \leftarrow T_1^{TD}$). Since the compound having the ICT state has little orbital overlaps between HOMO and LUMO, there is little interaction between the HOMO state and the LUMO state. As a result, the changes of spin states of electrons do not have an influence on other electrons, and a new charge transfer band (CT band) that does not follow the selection rule is formed within the delayed fluorescent material. When driving an OLED including the delayed fluorescent material TD, both 25% singlet excitons and 75% triplet excitons are converted to ICT state by heat, and then the converted excitons shifts to the ground state $S_0$ with luminescence. Therefore, the delayed fluorescent material TD may have 100% internal quantum efficiency in theory.

The delayed fluorescent material TD must has an energy level bandgap $\Delta E_{ST}^{TD}$ equal to or less than about 0.3 eV, for example, from about 0.05 to about 0.3 eV, between the excited singlet energy level $S_1^{TD}$ and the excited triplet energy level $T_1^{TD}$ so that exciton energy in both the excited singlet energy level $S_1^{TD}$ and the excited triplet energy level $T_1^{TD}$ can be transferred to the ICT state. The material having little energy level bandgap between the singlet energy level $S_1^{TD}$ and the triplet energy level $T_1^{TD}$ can exhibit common fluorescence which the excitons of singlet energy level $S_1^{TD}$ can be directly shifted to the ground state $S_0^{TD}$, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be shifted to the ground state $S_0^{TD}$.

Since the delayed fluorescent material TD obtain 100% luminous efficiency in theory, it can realize excellent internal quantum efficiency as the conventional phosphorescent material. In this case, the host can induce the triplet excitons at the delayed fluorescent material to participate in the luminescent process without quenching or non-radiative recombination. To this end, the energy levels between the host and the delayed fluorescent material should be adjusted.

Figure 4:
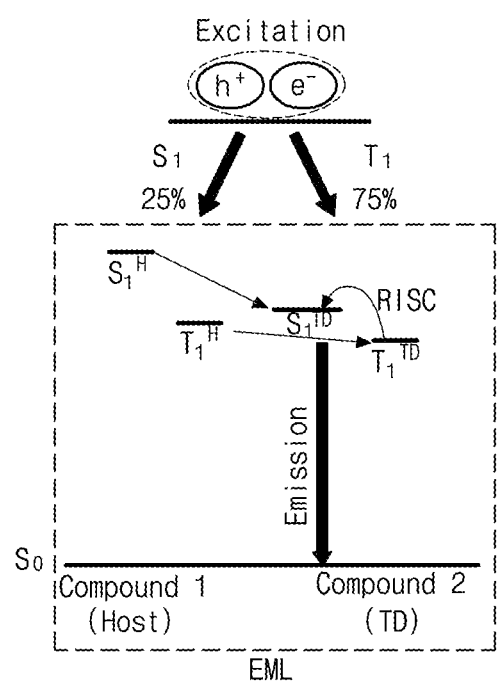
FIG. 4 is a schematic diagram illustrating luminous mechanism by energy level bandgap among luminous materials in accordance with an exemplary aspect of the present disclosure.

FIG. 4 is a schematic diagram illustrating luminous mechanism by energy level bandgap among luminous materials in accordance with an exemplary aspect of the present disclosure. As illustrated in FIG. 4, each of an excited singlet energy level $S_1^H$ and an excited triplet energy level $T_1^H$ of the first compound H, which can be the host in the EML 240, is higher than each of the excited singlet energy level $S_1^{TD}$ and the excited triplet energy level $T_1^{TD}$ of the second compound TD having the delayed fluorescent property. As an example, the excited triplet energy level $T_1^H$ of the first compound H may be higher than the excited triplet energy level $T_1^{TD}$ of the second compound TD by at least about 0.2 eV, at least about 0.3 eV, or at least about 0.5 eV.

When each of the excited triplet energy level $T_1^{TD}$ and the excited singlet energy level $S_1^H$ of the first compound H is not high enough than each of the excited triplet energy level $T_1^{TD}$ and the excited singlet energy level $S_1^{TD}$ of the second compound TD, the triplet state exciton energy of the second compound TD may be reversely transferred to the excited triplet energy level $T_1^H$ of the first compound H. In this case, the triplet exciton reversely transferred to the first compound H where the triplet exciton cannot be emitted is quenched as non-emission so that the triplet exciton energy of the second compound TD having the delayed fluorescent property cannot contribute to luminescence. The second compound TD having the delayed fluorescent property may have the energy level bandgap $\Delta E_{ST}^{TD}$ between the excited singlet energy level $S_1^{TD}$ and the excited triplet energy level $T_1^{TD}$ equal to or less than about 0.3 eV, for example between about 0.05 eV and about 0.3 eV (see, FIG. 3).

In addition, it is necessary to adjust properly HOMO energy levels and LUMO energy levels of the first compound H and the second compound TD. For example, an energy level bandgap ($|HOMO^H - HOMO^{TD}|$) between the HOMO energy level ($HOMO^H$) of the first compound H and the HOMO energy level ($HOMO^{TD}$) of the second compound TD, or an energy level bandgap ($|LUMO^H - LU$-

MO$^{TD}$|) between the LUMO energy level (LUMO$^H$) of the first compound H and the LUMO energy level (LUMO$^{TD}$) of the second compound TD may be equal to or less than about 0.5 eV, for example, between about 0.1 eV to about 0.5 eV.

When the EML 240 comprises the first compound H, any organic compound having the structure of Chemical Formulae 1 to 3 as well as the second compound TD having the delayed fluorescent property, the exciton energy can be transferred to the second compound TD without energy loss in the luminescence process. In this case, it is possible to minimize exciton quenching resulted from the interaction between the host excitons and the adjacent polarons and to prevent the luminous lifetime owing to electrical oxidation and optical oxidation from reducing.

The second compound may be blue-emitting, green-emitting or red-emitting delayed fluorescent material. In one exemplary aspect, the second compound as blue-emitting delayed fluorescent material in the EML 240 may comprise, but is not limited to, 1044-(diphenylphosphoryl)phenyl)-10H-phenoxazine 10,10'-(4,4'-(phenylphosphoyrl)bis(4,1-phenylene))bis(10H-phenoxazine) (DPXZPO), 10,10',10"-(4,4',4"-phosphoryltris(benzene-4,1-diyl))tris(10H-phenoxazine) (TPXZPO), 9,9'-(5-(4,6-diphenyl-1,3,5-triazin-2-yl)-1,3-phenylene)bis(9H-carbazole) (DcZTrz), 9,9',9"'',9""-((6-phenyl-1,3,5-triazin-2,4-diyl)bis(benzene-5,3,1-triyl))tetrakis(9H-carbazole) (DDczTrz), 2,7-bis(9,9-dimethylacridin-10(9H)-yl)-9,9-dimethyl-9H-thioxanthene-10,10-dioxide (DMTDAc), 9,9'-(4,4'-sulfonylbis(4,1-phenylene))bis(3,6-dimethoxyl-9H-carbazole) (DMOC-DPS), 10,10'-(4,4'-Sulfonylbis(4,1-phenylene))bis(9,9-dimethyl-9,10-dihydroacridine (DMAC-DPS), 10-(4-(4,6-diphenyl-1,3,5-triazin-2-yl)phenyl)-9,9-dimethyl-9,10-dihydroacridine (DMAC-TRZ), 10-phenyl-10H,10'H-spiro[acridine-9,9'-anthracen]-10'-one (ACRS A), 3,6-dibenzoyl-4,5-di(1-methyl-9-phenyl-9H-carbazoyl)-2-ethynylbenzonitrile (Cz-VPN), 9,9',9"-(5-(4,6-diphenyl-1,3,5-triazin-2-yl)benzene-1,2,3-triyl) tris(9H-carbazole) (TcZTrz), 2'-(10H-phenoxazin-10-yl)-[1,1':3',1"-terphenyl]-5'-carbonitrile (mPTC), bis(4-(9H-3,9'-bicarbazol-9-yl)phenyl)methanone (CC2BP), 9'-[4-(4,6-diphenyl-1,3,5-triazin-2-yl)phenyl]-3,3",6,6"-tetraphenyl-9,3":6',9"-ter-9H-carbazole (BDPCC-TPTA), 9'-[4-(4,6-diphenyl-1,3,5-triazin-2-yl)phenyl]-9,3':6',9"-ter-9H-carbazole (BCC-TPTA), 9-(4-(4,6-diphenyl-1,3,5-triazin-2-yl)phenyl)-3',6'-diphenyl-9H-3,9'-bicarbazole (DPCC-TPTA), 10-(4,6-diphenyl-1,3,5-triazin-2-yl)-10H-phenoxazine (Phen-TRZ), 9-(4-(4,6-diphenyl-1,3,5-triazin-2-yl)phenyl)-9H-carbazole (Cab-Ph-TRZ), 10-(4-(4,6-diphenyl-1,3,5-triazin-2-yl)phenyl)-10H-spiro[acridine-9,9'-fluorene] (SpiroAC-TRZ), 4,6-di(9H-carbazol-9-yl)isophthalonitrile (DczIPN), 3CzFCN and 2,3,4,6-tetra(9H-carbazol-9-yl)-5-fluorobenzonitrile (4CzFCN).

In another aspect, the second compound as green-emitting delayed fluorescent material in the EML 240 may comprise, but is not limited to, 5'-(phenoxazin-10-yl)-[1,1': 3',1"-terphenyl]-2'-carbonitrile (oPTC), 2-biphenyl-4,6-bis(12-phenylindolo[2,3-a]carbazol-11-yl)-1,3,5-triazine (PIC-TRZ), 9,9',9"(5-(4,6-diphenyl-1,3,5-triazin-2-yl)benzene-1,2,3-triyl)tris(3,6-dimentyl-9H-carbazole (TmCzTrz), 2,5-bis(4-(10H-phenoxazin-10-yl)phenyl)-1,3,4-oxadiazole (2PXZ-OXD), bis(4-(9,9-dimethylacridin-10(9H)-yl)phenyl)methanone (DMAC-BP), 2-(9-phenyl-9H-carbazol-3-yl)-10,10-dioxide-9H-thio xanthen-9-one (TXO-PhCz), 2,4,5,6-tetra(9H-carbazol-9-yl)isophthalonitrile (4CzIPN), 3,4,5,6-tetra(9H-carbazol-9-yl)isophthalonitrile (4CzPN), 2,3,4,6-tetra(9H-carbazol-9-yl)-5-fluorobenzonitrile (4CzFCN), 6,6-(9H,9'H-[3,3'-bicarbazole]-9,9'-diyl)bis(4-(9H-carbazol-9-yl)isophthalonitrile (33TczPN), 4,5-bis(5H-benzofuro[3,2-c]carbazol-5-yl)phthalonitrile (BFCz-2CN), 4,5-bis(5H-benzo[4,5]thieno[3,2-c]carbazol-5-yl)phthalonitrile (BTCz-2CN), 4,4"-bis(9,9-dimethylacridin-10(9H)-yl)-[1,1': 2',1"-terphenyl]-4',5'-dicarbonitrile (Ac-VPN), 4,4"-di(10H-phenoxazin-10-yl)-[1,1': 2',1"-terphenyl]-4',5'-dicarbonitrile (Px-VPN), 5,5'-(9H,9'H-[3,3'-bicarbazole]-9,9'-diyl)diisophthalnonitrile (35IPNDcz), 2,5'-(9H,9'H-[3,3'-bicarbazole]-9,9'-diyl)diisophthalnonitrile (26IPNDcz), 9,9',9"-(5-(4,6-diphenyl-1,3,5-triazin-2-yl)benzene-1,2,3-triyl)-tris(9H-carbazole) (TcZTrz) and 32alCTRZ.

In still another exemplary aspect, the second compound as red-emitting delayed fluorescent material in the EML 240 may comprise, but is not limited to, 1,3-bis[4-(10H-phenoxazin-10-yl)benzoyl]benzene (mPx2BBP), 2,3,5,6-tetrakis(3,6-diphenylcarbazol-9-yl)-1,4-dicyanobenzene (4CzTPN-Ph), 10,10'-(sulfonylbis(4,1-phenylene))bis(5-phenyl-5,10-dihydrophenazine) (PPZ-DPS), 5,10-bis(4-(benzo[d]thiazol-2-yl)phenyl)-5,10-dihydrophenazine (DHPZ-2BTZ), 5,10-bis(4-(4,6-diphenyl-1,3,5-triazin-2-yl)phenyl)-5,10-dihydrophenazine (DHPZ-2TRZ) and 7,10-bis(4-(diphenylamino)phenyl)-2,3-dicyanopyrazino phenanathrene (TPA-DCPP).

When the EML 240 includes the first compound H as the host and the second compound TD as the delayed fluorescent material, the contents of the second compound TD in the EML 240 may be, but is not limited to, about 1 wt % to about 70 wt %, about 10 wt % to about 50 wt %, or about 20 wt % to about 50 wt %.

Figure 5:
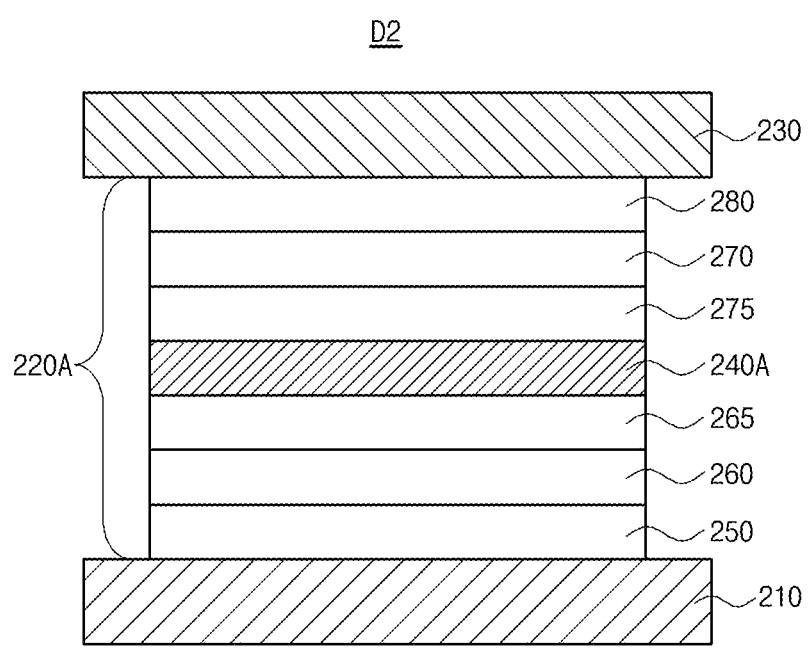
FIG. 5 is a schematic cross-sectional view illustrating an OLED in accordance with another exemplary aspect of the present disclosure.

The EML may include plural dopants having different luminous properties. FIG. 5 is a schematic cross-sectional view illustrating an OLED in accordance with another exemplary aspect of the present disclosure. As illustrated in FIG. 5, the OLED D2 comprises the first electrode 210, the second electrode 230 facing the first electrode 210 and an emissive layer 220A disposed between the first and second electrodes 210 and 230. The emissive layer 220A with single emitting part comprises an EML 240A. The organic light emitting display device 100 (FIG. 1) includes a red pixel region, a green pixel region and a blue pixel region, and the OLED D2 may be disposed in any pixel region of the red, green and blue pixel regions.

The emissive layer 220A may comprise at least one of the HTL 260 disposed between the first electrode 210 and the EML 240 and the ETL 270 disposed between the second electrode 230 and the EML 240. Also, the emissive layer 220A may further comprise at least one of the HIL 250 disposed between the first electrode 210 and the HTL 260 and the EIL 280 disposed between the second electrode 230 and the ETL 270. Alternatively, the emissive layer 220A may further comprise the EBL 265 disposed between the HTL 260 and the EML 240A and/or the HBL 275 disposed between the EML 240A and the ETL 270. The configurations of the first and second electrodes 210 and 230 as well as other layers except the EML 240A in the emissive layer 220A is substantially identical to the corresponding electrodes and layers in the OLED D1.

In the second aspect, the EML 240A comprise the first compound (Compound 1, Host) H, the second compound (Compound 2, first dopant) TD and a third compound (Compound 3, second dopant) FD. The first compound H may be the host, the second compound TD may be the delayed florescent material, and the third compound FD may be the fluorescent material. The first compound H may comprise any organic compound having the structure of Chemical Formulae 1 to 3. When the EML 240A further comprises the fluorescent material as well as the delayed fluorescent material as dopants, the OLED D2 can further improve its luminous efficiency and color purity by adjusting energy levels among those luminous materials.

When the EML includes only the second compound having the delayed fluorescent property as the dopant, the EML may implement high internal quantum efficiency as the prior art phosphorescent materials including heavy metals because the dopant can exhibit 100% internal quantum efficiency in theory.

However, because of the bond formation between the electron acceptor and the electron donor and conformational twists within the delayed fluorescent material, additional charge transfer transition (CT transition) within the delayed fluorescent material is caused thereby, and the delayed fluorescent material has various geometries. As a result, the delayed fluorescent materials show emission spectra having very broad FWHM (full-width at half maximum) in the course of luminescence, which results in poor color purity. In addition, the delayed fluorescent material utilizes the triplet exciton energy as well as the singlet exciton energy in the luminescence process with rotating each moiety within its molecular structure, which results in twisted internal charge transfer (TICT). As a result, the luminous lifetime of an OLED including only the delayed fluorescent materials may be reduced owing to weakening of molecular bonding forces among the delayed fluorescent materials.

Figure 6:
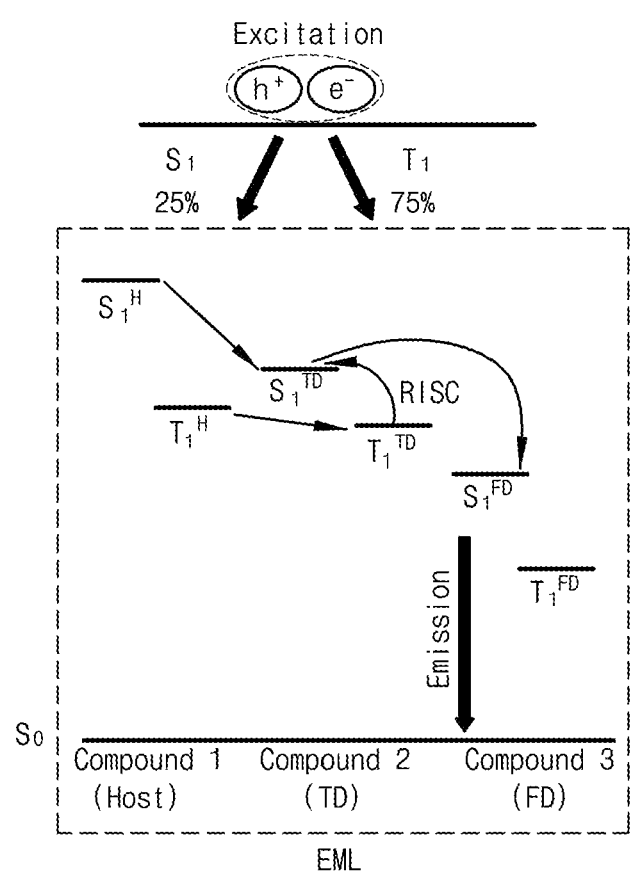
FIG. 6 is a schematic diagram illustrating luminous mechanism by energy level bandgap among luminous materials in accordance with another exemplary aspect of the present disclosure.

In the second aspect, the EML 240A further includes the third compound, which may be fluorescent or phosphorescent material, in order to prevent the color purity and luminous lifetime from being reduced in case of using only the delayed fluorescent material as the dopant. As illustrated in FIG. 6, the triplet exciton energy of the second compound TD having the delayed fluorescent property is converted upwardly to its own singlet exciton energy by RISC mechanism, then the converted singlet exciton energy of the second compound TD can be transferred to the third compound FD, which may be the fluorescent or phosphorescent material, in the same EML 240A by Forster Resonance Energy Transfer (FRET) mechanism to implement a hyper-fluorescence.

When the EML 240A includes the first compound H which may be any organic compound having the structure of Chemical Formulae 1 to 3, the second compound TD having the delayed fluorescent property and the third compound FD which is the fluorescent or phosphorescent material, it is necessary to adjust properly energy levels among those luminous materials. FIG. 6 is a schematic diagram illustrating luminous mechanism by energy level bandgap among luminous materials in accordance with another exemplary aspect of the present disclosure.

An energy level bandgap $\Delta E_{ST}^{TD}$ between the excited singlet energy level $S_1^{TD}$ and the excited triplet energy level $T_1^{TD}$ of the second compound TD, which is the delayed fluorescent material, may be equal to or less than about 0.3 eV in order to realize the delayed fluorescence (see, FIG. 3). In addition, each of the excited singlet energy level $S_1^H$ and the excited triplet energy level $T_1^H$ of the first compound H as the host is higher than each of the excited singlet energy level $S_1^{TD}$ and the excited triplet energy level $T_1^{TD}$ of the second compound TD as the delayed fluorescent material, respectively. As an example, the excited triplet energy level $T_1^H$ of the first compound H may be higher than the excited triplet energy level $T_1^{TD}$ of the second compound TD by at least about 0.2 eV.

Moreover, the excited triplet energy level $T_1^{TD}$ of the second compound TD is higher than an excited triplet energy level $T_1^{FD}$ of the third compound FD, which is the fluorescent or phosphorescent material. In one exemplary aspect, the excited singlet energy level $S_1^{TD}$ of the second compound TD may be higher than an excited singlet energy level $S_1^{FD}$ of the third compound FD.

In addition, the energy level bandgap ($|HOMO^H-HOMO^{TD}|$) between the HOMO energy level ($HOMO^H$) of the first compound H as the host and the HOMO energy level ($HOMO^{TD}$) of the second compound TD as the delayed fluorescent material, or the energy level bandgap ($|LUMO^H-LUMO^{TD}|$) between the LUMO energy level ($LUMO^H$) of the first compound H and the LUMO energy level ($LUMO^{TD}$) of the second compound TD may be equal to or less than about 0.5 eV.

For example, the first compound H which can be the host may include any organic compound having the structure of Chemical Formulae 1 to 3. The second compound may comprise the organic compound as described in the first aspect.

The exciton energy should be effectively transferred from the second compound TD as the delayed fluorescent material to the third compound FD as the fluorescent or phosphorescent material in order to implement hyper-fluorescence. As an example, the fluorescent or phosphorescent material having the absorption spectrum with large overlapping area with the luminescence spectrum of the second compound TD having the delayed fluorescent property may be used as the third compound FD in order to transfer exciton energy efficiently from the second compound to the third compound.

The third compound FD may emit blue (B), green (G) or red (R) light. In one exemplary aspect, the third compound FD as the fluorescent material may emit blue (B) light. For example, the third compound may comprise, but is not limited to, pyrene-based compounds, anthracene-based compounds, fluoranthene-based compounds and boron-based compounds. For example, the third compound FD as is the blue-emitting fluorescent material may comprise any-one having the following structure of Chemical Formula 4:

[Chemical Formula 4]

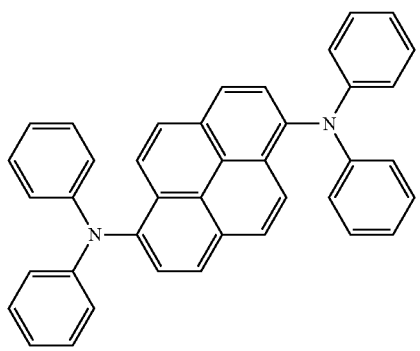

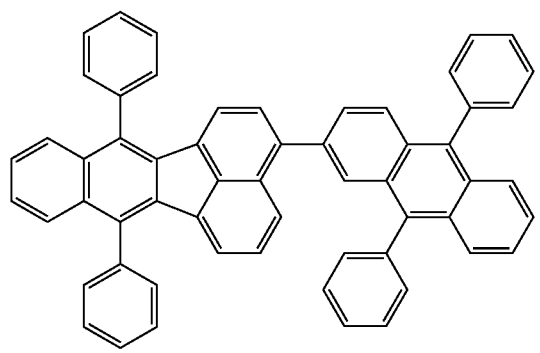
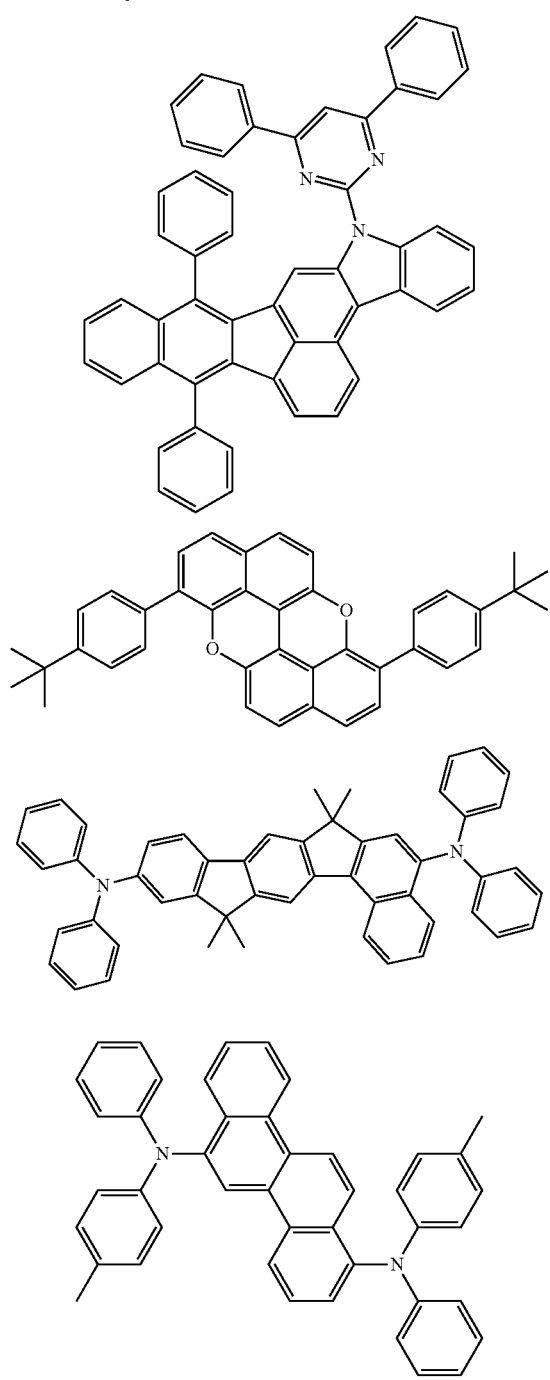
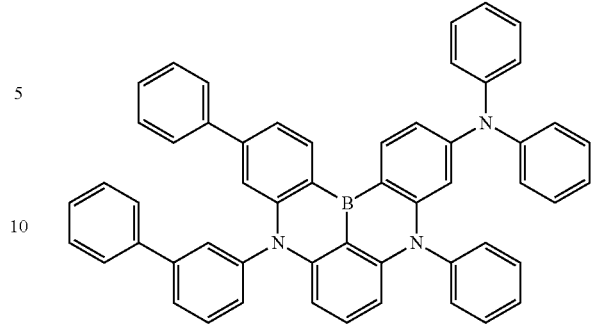

In another exemplary aspect, the third compound FD as the green-emitting fluorescent material may comprise, but is not limited to, a boron-dypyrromethene (4,4-difluoro-4-bora-3a,4a-diaza-s-indacene, BODIPY) core. Alternatively, metal complex as the phosphorescent material emitting blue, green or red may be used as the third compound FD.

In one exemplary aspect, the contents of the first compound H may be larger than the contents of the second compound TD, and the contents of the second compound TD is larger than the contents of the third compound FD. In this case, exciton energy can be transferred efficiently from the second compound TD to the third compound FD via FRET mechanism. As an example, each of the contents of the first to third compounds H, TD and FD in the EML 240 may be, but is not limited to, about 60 wt % to about 75 wt %, about 20 wt % to about 40 wt % and about 0.1 wt % to about 5 wt %, respectively.

Figure 7:
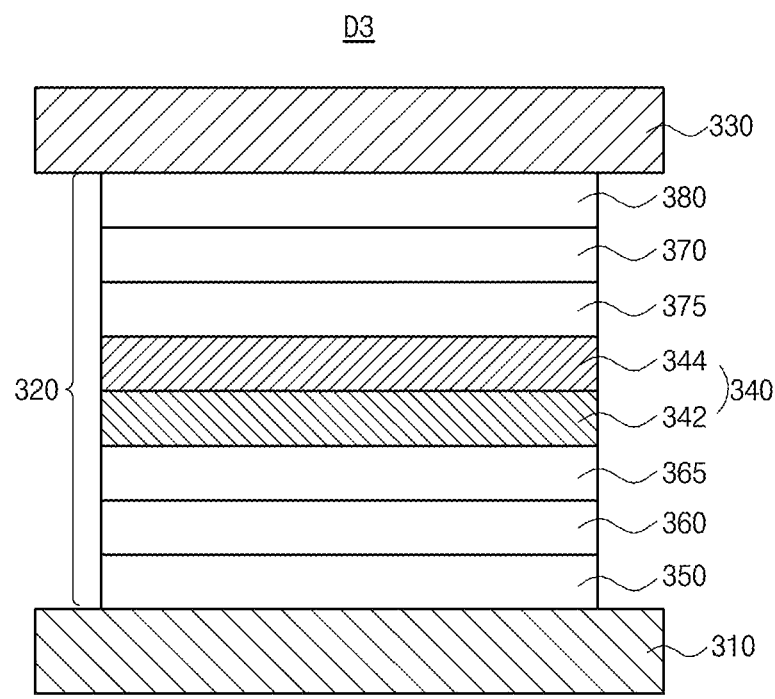
FIG. 7 is a schematic cross-sectional view illustrating an OLED in accordance with another exemplary aspect of the present disclosure.
Figure 8:
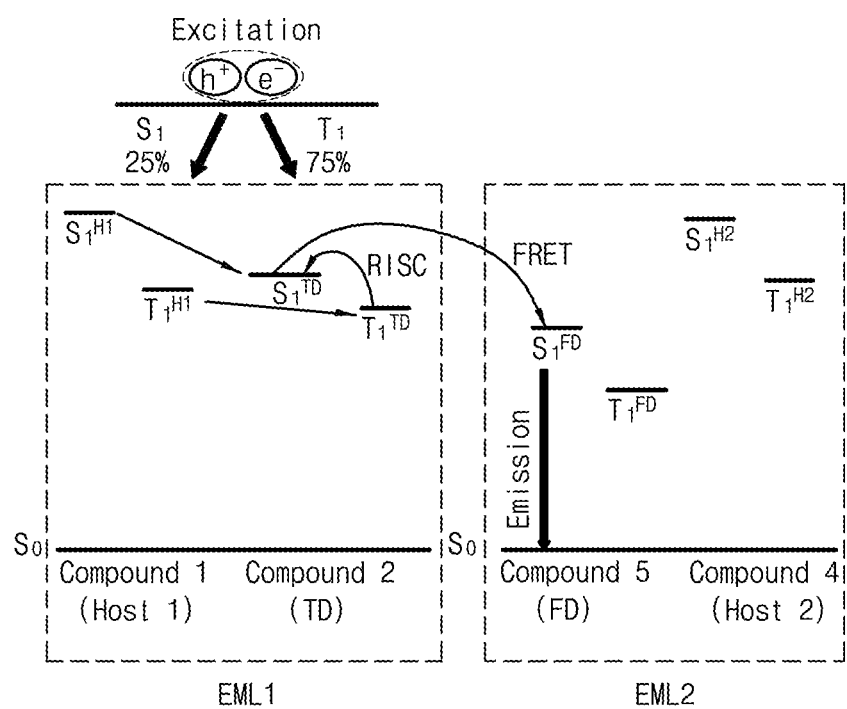
FIG. 8 is a schematic diagram illustrating luminous mechanism by energy level bandgap among luminous materials in accordance with another exemplary aspect of the present disclosure.

Alternatively, an OLED in accordance with the present disclosure may include multiple-layered EML. FIG. 7 is a schematic cross-sectional view illustrating an OLED having a double-layered EML in accordance with another exemplary aspect of the present disclosure. FIG. 8 is a schematic diagram illustrating luminous mechanism by energy level bandgap among luminous materials in accordance with another exemplary aspect of the present disclosure.

As illustrated in FIG. 7, the OLED D3 includes first and second electrodes 310 and 330 facing each other and an emissive layer 320 with single emitting part disposed between the first and second electrodes 310 and 330.

In one exemplary aspect, the emissive layer 320 comprises an EML 340. The organic light emitting display device 100 (FIG. 1) includes a red pixel region, a green pixel region and a blue pixel region, and the OLED D3 may be disposed in any pixel region of the red, green and blue pixel regions. The emissive layer 320 may comprise at least one of an HTL 360 disposed between the first electrode 310 and the EML 340 and an ETL 370 disposed between the second electrode 230 and the EML 340. Also, the emissive layer 320 may further comprise at least one of a HIL 350 disposed between the first electrode 310 and the HTL 360 and an EIL 380 disposed between the second electrode 330 and the ETL 370. Alternatively, the emissive layer 320 may further comprise an EBL 365 disposed between the HTL 360 and the EML 340 and/or a HBL 375 disposed between the EML 340 and the ETL 370. The configurations of the first and second electrodes 310 and 330 as well as other layers except the EML 340 in the emissive layer 320 is substantially identical to the corresponding electrodes and layers in the OLED D1 or the OLED D2.

The EML 340 includes a first EML (EML1, lower EML, first layer) 342 and a second EML (EML2, upper EML, second layer) 344. The EML1 342 is disposed between the EBL 365 and the HBL 375 and the EML2 344 is disposed between the EML1 342 and the HBL 375. One of the EML1 342 and the EML2 344 includes a second compound (Compound 2, first dopant) TD that is the delayed fluorescent material, and the other of the EML1 342 and the EML2 344 includes a fifth compound (Compound 5, second dopant) FD that is the fluorescent or phosphorescent material. Also, each of the EML1 342 and the EML2 344 comprises the first compound (Compound 1, first host (Host 1)) H1 and a fourth compound (Compound 4, second host (Host 2)) H2, respectively. In the exemplary third aspect, the EML1 342 includes the first compound H1 that may be the first host and the second compound TD that may by the delayed fluorescent material. The EML2 344 includes the fourth compound H2 that may be the second host and the fifth compound FD that may be the fluorescent or phosphorescent material.

More particularly, the EML1 342 includes the first compound H1 that is any organic compound having the structure of Chemical Formulae 1 to 3, and the second compound TD that is the delayed fluorescent material. The triplet exciton energy of the second compound TD can be transferred to its own singlet exciton energy via RISC mechanism. While the second compound has high internal quantum efficiency, but it has poor color purity due to its wide FWHM (full-width half maximum).

On the contrary, the EML2 344 may include the fourth compound H2 that may be the second host and the fifth compound FD that is the fluorescent or phosphorescent material. While the fifth compound FD as the fluorescent material has an advantage in terms of color purity due to its narrow FWHM, but its internal quantum efficiency is low because its triplet exciton cannot be involved in the luminescence process.

However, in this exemplary aspect, the singlet exciton energy and the triplet exciton energy of the second compound having the delayed fluorescent property in the EML1 342 can be transferred to the fifth compound, which may be the fluorescent or phosphorescent material, in the EML2 344 disposed adjacently to the EML1 342 by FRET mechanism, which transfers energy non-radially through electrical fields by dipole-dipole interactions. Accordingly, the ultimate light emission occurs in the fifth compound within the EML2 344.

In other words, the triplet exciton energy of the second compound TD is converted upwardly to its own singlet exciton energy in the EML1 342 by RISC mechanism. Then, the converted singlet exciton energy of the second compound TD is transferred to the singlet exciton energy of the fifth compound FD in the EML2 344. The fifth compound FD in the EML2 344 can emit light using the triplet exciton energy as well as the singlet exciton energy. As the exciton energy which is generated at the second compound TD having the delayed fluorescent property in the EML1 342 is efficiently transferred from the second compound TD to the fifth compound FD that is the fluorescent or phosphorescent material in the EML2 344, hyper-fluorescence can be realized. In this case, the substantial light emission is occurred in the EML2 344 including the fifth compound FD which is the fluorescent or phosphorescent material and has a narrow FWHM. Accordingly, the OLED D3 can enhance its quantum efficiency and improve its color purity due to narrow FWHM.

Each of the EML1 342 and the EML2 344 includes the first compound H1 as the first host and the fourth compound H2 as the second host, respectively. The exciton energies generated at the first and fourth compounds H1 and H2 should be transferred to the second compound TD as the delayed fluorescent material to emit light. As illustrated in FIG. 8, each of excited singlet energy levels $S_1^H1$ and $S_1^H2$ and excited triplet energy levels $T_1^H1$ and $T_1^H2$ of the first and fourth compounds H1 and H2 should be higher than each of the excited singlet energy level $S_1^{TD}$ and the excited triplet energy level $T_1^{TD}$ of the second compound TD as the delayed fluorescent material, respectively. As an example, each of the excited triplet energy levels $T_1^H1$ and $T_1^H2$ of the first and fourth compounds H1 and H2 may be higher than the excited triplet energy level $T_1^{TD}$ of the second compound TD by at least about 0.2 eV, for example by at least about 0.3 eV, or by at least about 0.5 eV.

The excited singlet energy level $S_1^H2$ of the fourth compound H2 is higher than the excited singlet energy level $S_1^{FD}$ of the fifth compound FD. In this case, the singlet exciton energy generated at the fourth compound H2 can be transferred to the excited singlet energy level $S_1^{FD}$ of the fifth compound FD. Optionally, the excited triplet energy level $T_1^H2$ of the fourth compound H2 may be higher than the excited triplet energy level $T_1^{TD}$ of the fifth compound FD.

In addition, it is necessary for the EML 340 to implement high luminous efficiency and color purity as well as to transfer exciton energy efficiently from the second compound TD, which is converted to ICT complex state by RISC mechanism in the EML1 342, to the fifth compound FD which is the fluorescent or phosphorescent material in the EML2 344. In order to realize such an OLED D3, the excited triplet energy level $T_1^{TD}$ of the second compound TD is higher than the excited triplet energy level $T_1^{TD}$ of the fifth compound FD. Optionally, the excited singlet energy level $S_1^{TD}$ of the second compound TD may be higher than the excited singlet energy level $S_1^{FD}$ of the fifth compound FD.

Moreover, the energy level bandgap ($|HOMO^H-HOMO^{TD}|$) between the HOMO energy level ($HOMO^H$) of the first and/or fourth compounds H1 and H2 and the HOMO energy level ($HOMO^{TD}$) of the second compound TD, or the energy level bandgap ($|LUMO^H-LUMO^{TD}|$) between a LUMO energy level ($LUMO^H$) of the first and/or fourth compounds H1 and H2 and the LUMO energy level ($LUMO^{TD}$) of the second compound TD may be equal to or less than about 0.5 eV. When the luminous materials do not satisfy the required energy levels as described above, exciton energies are quenched at the second and fifth compounds TD and FD or exciton energies cannot transferred efficiently from the first and fourth compounds H1 and H2 to the second and fifth compounds TD and FD, so that OLED D3 may have reduced quantum efficiency.

The first compound H1 and the fourth compound H2 may be the same or different from each other. For example, each of the first compound H1 and the fourth compound H2 may independently include any organic compound having the structure of Chemical Formulae 1 to 3. The second compound TD may be the same as described above.

The fifth compound FD may have a narrow FWHM and have an absorption spectrum with large overlapping area with a luminescent spectrum of the second compound TD. The fifth compound FD may the fluorescent or phosphorescent material emitting blue, green or red light. For example, the fifth compound FD may be the fluorescent or phosphorescent material emitting blue, green or red light as described above.

In one exemplary embodiment, the contents of the first and fourth compounds H1 and H2 in the EML1 342 and the EML2 344 may be larger than or equal to the contents of the second and fifth compounds TD and FD in the same layer. Also, the contents of the second compound TD in the EML1 342 may be larger than the contents of the fifth compound FD in the EML2 344. In this case, exciton energy can be transferred efficiently from the second compound TD to the fifth compound FD via FRET mechanism. As an example, the contents of the second compound TD in the EML1 342 may be, but is not limited to, about 1 wt % to about 70 wt %, about 10 wt % to about 50 wt %, or about 20 wt % to about 50 wt %. In addition, the contents of the fourth compound H2 in the EML2 344 may be about 90 wt % to about 99 wt %, or 95 wt % to about 99 wt %, and the contents of the fifth compound FD in the EML2 344 may be about 1 wt % to about 10 wt %, or about 1 wt % to about 5 wt %.

When the EML2 344 is disposed adjacently to the HBL 375 in one exemplary aspect, the fourth compound H2, which is included in the EML2 344 together with the fifth compound FD, may be the same material as the HBL 375. In this case, the EML2 344 may have a hole blocking function as well as an emission function. In other words, the EML2 344 can act as a buffer layer for blocking holes. In one aspect, the HBL 375 may be omitted where the EML2 344 may be a hole blocking layer as well as an emitting material layer.

When the EML2 344 is disposed adjacently to the EBL 365 in another exemplary aspect, the fourth compound H2 may be the same material as the EBL 365. In this case, the EML2 344 may have an electron blocking function as well as an emission function. In other words, the EML2 344 can act as a buffer layer for blocking electrons. In one aspect, the EBL 365 may be omitted where the EML2 344 may be an electron blocking layer as well as an emitting material layer.

Figure 9:
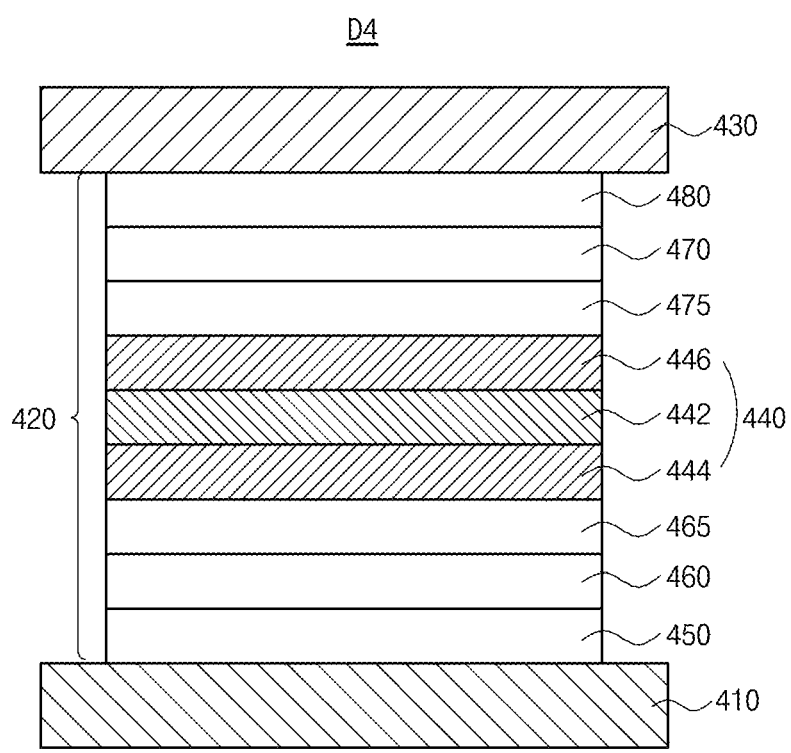
FIG. 9 is a schematic cross-sectional view illustrating an OLED in accordance with another exemplary aspect of the present disclosure.
Figure 10:
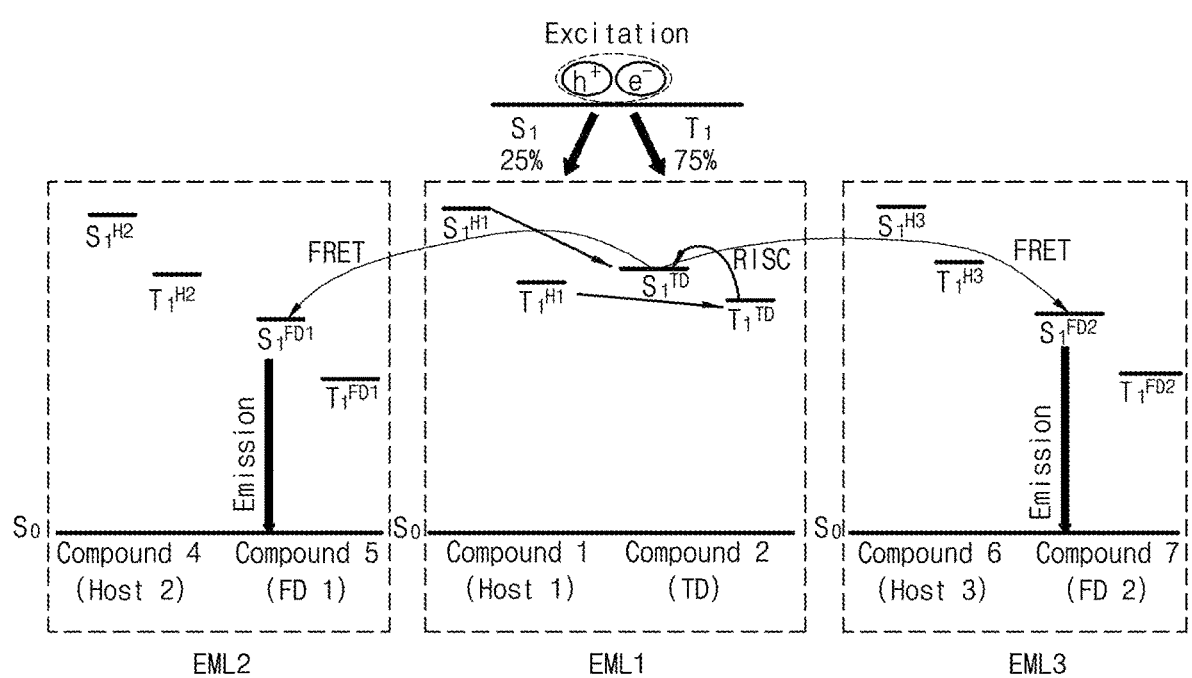
FIG. 10 is a schematic diagram illustrating luminous mechanism by energy level bandgap among luminous materials in accordance with another exemplary aspect of the present disclosure.

An OLED having a triple-layered EML will be explained. FIG. 9 is a schematic cross-sectional view illustrating an OLED having a triple-layered EML in accordance with another exemplary aspect of the present disclosure. FIG. 10 is a schematic diagram illustrating luminous mechanism by energy level bandgap among luminous materials in accordance with another exemplary aspect of the present disclosure.

As illustrated in FIG. 9, the OLED D4 comprises first and second electrodes 410 and 430 facing each other and an emissive layer 420 with single emitting part disposed between the first and second electrodes 410 and 430. The organic light emitting display device 100 (FIG. 1) includes a red pixel region, a green pixel region and a blue pixel region, and the OLED D4 may be disposed in any pixel region of the red, green and blue pixel regions.

In one exemplary aspect, the emissive layer 420 comprises a three-layered EML 440. The emissive layer 420 may comprise at least one of a HTL 460 disposed between the first electrode 410 and the EML 440 and an ETL 370 disposed between the second electrode 430 and the EML 440. Also, the emissive layer 420 may further comprise at least one of a HIL 450 disposed between the first electrode 410 and the HTL 460 and an EIL 480 disposed between the second electrode 420 and the ETL 470. Alternatively, the emissive layer 420 may further comprise an EBL 465 disposed between the HTL 460 and the EML 440 and/or a HBL 475 disposed between the EML 440 and the ETL 470. The configurations of the first and second electrodes 410 and 430 as well as other layers except the EML 440 in the emissive layer 420 is substantially identical to the corresponding electrodes and layers in the OLEDs D1, D2 and D3.

The EML 440 comprises a first EML (EML1, middle EML, first layer) 442, a second EML (EML2, lower EML, second layer) 444 and a third EML (EML3, upper EML, third layer) 446. The EML1 442 is disposed between the EBL 465 and the HBL 475, the EML2 444 is disposed between the EBL 465 and the EML1 442 and the EML3 446 is disposed between the EML1 442 and the HBL 475.

The EML1 442 comprises the second compound (Compound 2, first dopant) TD that may be the delayed fluorescent material. Each of the EML2 444 and the EML3 446 comprises the fifth compound (Compound 5, second dopant) FD1 and a seventh compound (Compound 7, third dopant) FD2 each of which may be the fluorescent or phosphorescent material, respectively. In addition, each of the EML1 442, EML2 444 and EML3 446 further includes the first compound (Compound 1, Host 1) H1, the fourth compound (Compound 4, Host 2) H2 and the sixth compound (Compound 6, Host 3) H3 each of which may be the first to third hosts, respectively.

In accordance with this aspect, the singlet energy as well as the triplet energy of the second compound TD, i.e. the delayed fluorescent material in the EML1 442 can be transferred to the fifth and seventh compounds FD1 and FD2, i.e. the fluorescent or phosphorescent materials each of which is included in the EML2 444 and EML3 446 disposed adjacently to the EML1 442 by FRET mechanism. Accordingly, the ultimate emission occurs in the fifth and seventh compounds FD1 and FD2 in the EML2 444 and the EML3 446.

The triplet exciton energy of the second compound TD having the delayed fluorescent property in the EML1 442 is converted upwardly to its own singlet exciton energy by RISC mechanism, then the singlet exciton energy of the second compound TD is transferred to the singlet exciton energy of the fifth and seventh compounds FD1 and FD2 in the EML2 444 and the EML3 446 because the second compound TD has the excited singlet energy level $S_1^{TD}$ higher than each of the excited singlet energy levels $S_1^{FD}1$ and $S_1^{FD}2$ of the fifth and seventh compounds FD1 and FD2 (see, FIG. 10). The singlet exciton energy of the second compound TD in the EML1 442 is transferred to the fifth and seventh compounds FD1 and FD2 in the EML2 444 and the EML3 446 which are disposed adjacently to the EML1 442 by FRET mechanism.

The fifth and seventh compounds FD1 and FD2 in the EML2 444 and EML3 446 can emit light using the singlet exciton energy and the triplet exciton energy derived from the second compound TD. Each of the fifth and seventh compounds FD1 and FD2 may have narrower FWHM compared to the second compound TD. As the exciton energy, which is generated at the second compound TD having the delayed fluorescent property in the EML1 442, is transferred to the fifth and seventh compounds FD1 and FD2 in the EML2 444 and the EML3 446, hyper-fluorescence can be realized. Particularly, each of the fifth and seventh compounds FD1 and FD2 may have a luminescent spectrum having a large overlapping area with an absorption spectrum of the second compound TD, so that exciton energy of the second compound TD may be transferred efficiently to each of the fifth and seventh compounds FD1 and FD2. In this case, substantial light emission is occurred in the EML2 444 and in the EML3 446.

To implement efficient luminescence in the EML 440, it is necessary to adjust properly energy levels among luminous materials in the EML1 442, the EML2 444 and the EML3 446. As illustrated in FIG. 10, each of excited singlet energy levels $S_1^H1$, $S_1^H2$ and $S_1^H3$ and excited triplet energy levels $T_1^H1$, $T_1^H2$ and $T_1^H3$ of the first, fourth and sixth compounds H1, H2 and H3, each of which may be the first to third hosts, respectively, should be higher than each of the excited singlet energy level $S_1^{TD}$ and the excited triplet energy level $T_1^{TD}$ of the second compound TD that may be the delayed fluorescent material, respectively.

In addition, it is necessary for the EML 440 to implement high luminous efficiency and color purity as well as to transfer exciton energy efficiently from the second compound TD, which is converted to ICT complex state by RISC mechanism in the EML1 442, to the fifth and seventh compounds FD1 and FD2 each of which is the fluorescent or phosphorescent material in the EML2 444 and the EML3 446. In order to realize such an OLED D4, the excited triplet energy level $T_1^{TD}$ of the second compound TD in the EML1 442 is higher than each of excited triplet energy levels $T_1^{FD}1$ and $T_1^{FD}2$ of the fifth and seventh compounds FD1 and FD2. Alternatively, the excited singlet energy level $S_1^{TD}$ of the second compound TD may be higher than each of excited singlet energy levels $S_1^{FD}1$ and $S_1^{FD}2$ of the fifth and seventh compounds FD1 and FD2 as fluorescent or phosphorescent material.

Moreover, the exciton energy, which is transferred from the second compound TD to each of the fifth and seventh compounds FD1 and FD2, should not be transferred to the fourth and sixth compounds H2 and H3 in order to realize efficient light emission. As an example, each of the excited singlet energy levels $S_1^{H}2$ and $S_1^{H}3$ of the fourth and sixth compounds H2 and H3 may be higher than each of the excited singlet energy levels $S_1^{FD}1$ and $S_1^{FD}2$ of the fifth and seventh compounds FD1 and FD2, respectively.

Each of the EML1 442, the EML2 444 and the EML3 446 may include the first, fourth and sixth compounds H1, H2 and H3 each of which may be the first to third hosts, respectively. For example, each of the first, fourth and sixth compounds H1, H2 and H3 may be the same or different from each other. For Example, each of the first, fourth and sixth compounds H1, H2 and H3 may independently include any organic compound having the structure of Chemical Formulae 1 to 3. The second compound TD may be the same as described above.

Each of the fifth and seventh compounds FD1 and FD2 may have a narrow FWHM and have an absorption spectrum with large overlapping area with a luminescent spectrum of the second compound TD. Each of the fifth and seventh compounds FD1 and FD2 may the fluorescent or phosphorescent material emitting blue, green or red light. For example, each of the fifth and seventh compounds FD1 and FD2 may be the fluorescent or phosphorescent material emitting blue, green or red light as described above.

In one exemplary aspect, each of the contents of the fourth and sixth compounds H2 and H3 in the EML2 444 and the EML3 446 may be larger than or equal to each of the contents of the fifth and seventh compounds in the same layer. Also, the contents of the second compound TD in the EML1 442 may be larger than each of the contents of the fifth and seventh compounds FD1 and FD2 in the EML2 444 and in the EML3 446. In this case, exciton energy can be transferred efficiently from the second compound to the fifth and seventh compounds via FRET mechanism. As an example, the contents of the second compound TD in the EML1 442 may be, but is not limited to, about 1 wt % to about 70 wt %, or about 10 wt % to about 50 wt %, or about 20 wt % to about 50 wt %. In addition, each of the contents of the fourth and sixth compounds H2 and H3 in the EML2 444 and in the EML3 446 may be about 90 wt % to about 99 wt %, or about 95 wt % to about 99 wt %, and each of the contents of the fifth and seventh compounds FD1 and FD2 in the EML2 444 and in the EML3 446 may be about 1 wt % to about 10 wt %, or about 1 wt % to about 5 wt %.

When the EML2 444 is disposed adjacently to the EBL 465 in one exemplary aspect, the fourth compound H2, which is included in the EML2 444 together with the fifth compound FD1, may be the same material as the EBL 465. In this case, the EML2 444 may have an electron blocking function as well as an emission function. In other words, the EML2 444 can act as a buffer layer for blocking electrons. In one aspect, the EBL 465 may be omitted where the EML2 444 may be an electron blocking layer as well as an emitting material layer.

When the EML3 446 is disposed adjacently to the HBL 475 in another exemplary aspect, the sixth compound H3, which is included in the EML3 446 together with the seventh compound FD2, may be the same material as the HBL 475. In this case, the EML3 446 may have a hole blocking function as well as an emission function. In other words, the EML3 446 can act as a buffer layer for blocking holes. In one aspect, the HBL 475 may be omitted where the EML3 446 may be a hole blocking layer as well as an emitting material layer.

In still another exemplary aspect, the fourth compound H2 in the EML2 444 may be the same material as the EBL 465 and the sixth compound H3 in the EML3 446 may be the same material as the HBL 475. In this aspect, the EML2 444 may have an electron blocking function as well as an emission function, and the EML3 446 may have a hole blocking function as well as an emission function. In other words, each of the EML2 444 and the EML3 446 can act as a buffer layer for blocking electrons or hole, respectively. In one aspect, the EBL 465 and the HBL 475 may be omitted where the EML2 444 may be an electron blocking layer as well as an emitting material layer and the EML3 446 may be a hole blocking layer as well as an emitting material layer.

Figure 11:
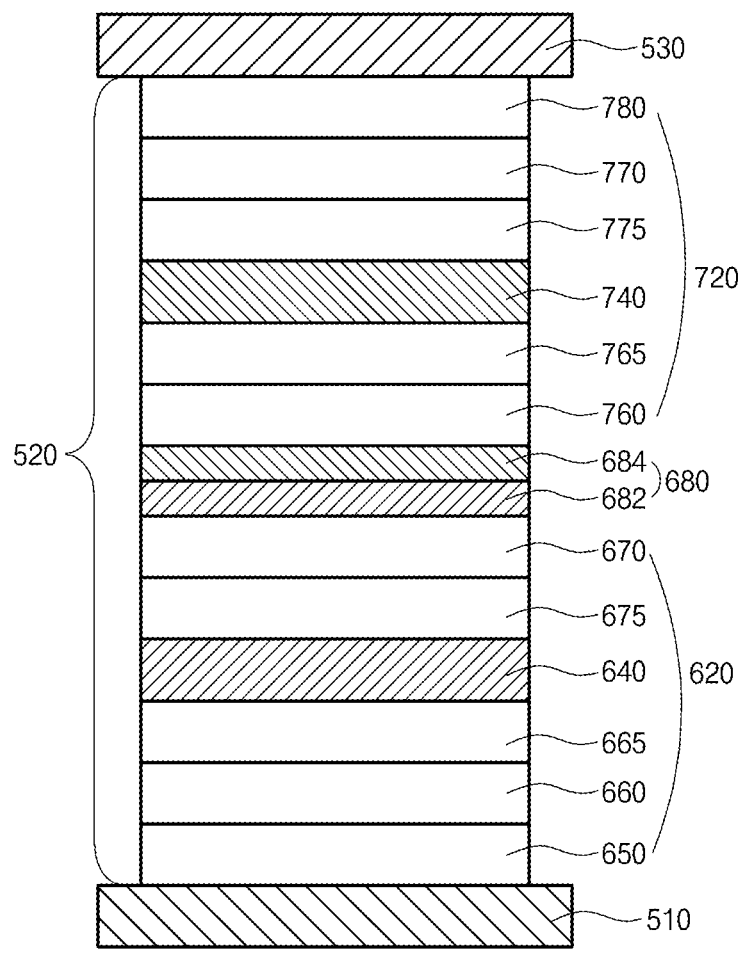
FIG. 11 is a schematic cross-sectional view illustrating an OLED in accordance with still another exemplary aspect of the present disclosure.

In an alternative aspect, an OLED may include multiple emitting parts. FIG. 11 is a schematic cross-sectional view illustrating an OLED in accordance with still another exemplary aspect of the present disclosure.

As illustrated in FIG. 11, the OLED D5 comprises first and second electrodes 510 and 530 facing each other and an emissive layer 520 with two emitting parts disposed between the first and second electrodes 510 and 530. The organic light emitting display device 100 (FIG. 1) includes a red pixel region, a green pixel region and a blue pixel region, and the OLED D5 may be disposed in any pixel region of the red, green and blue pixel regions. In one exemplary aspect, the OLED D5 may be disposed in the blue pixel region. The first electrode 510 may be an anode and the second electrode 520 may be a cathode.

The emissive layer 520 includes a first emitting part 620 that includes a first EML (EML1) 640, and a second emitting part 720 that includes a second EML (EML2) 740. Also, the emissive layer 520 may further comprise a charge generation layer (CGL) 680 disposed between the first emitting part 620 and the second emitting part 720.

The CGL 680 is disposed between the first and second emitting parts 620 and 720 so that the first emitting part 620, the CGL 680 and the second emitting part 720 are sequentially disposed on the first electrode 510. In other words, the first emitting part 620 is disposed between the first electrode 510 and the CGL 680 and the second emitting part 720 is disposed between the second electrode 530 and the CGL 680.

The first emitting part 620 comprises the EML1 640. The first emitting part 620 may further comprise at least one of a first HTL (HTL1) 660 disposed between the first electrode 510 and the EML1 640, a HIL 650 disposed between the first electrode 510 and the HTL1 660 and a first ETL (ETL1) 670 disposed between the EML1 640 and the CGL 680. Alternatively, the first emitting part 620 may further comprise a first EBL (EBL1) 665 disposed between the HTL1 660 and the EML1 640 and/or a first HBL (HBL1) 675 disposed between the EML1 640 and the ETL1 670.

The second emitting part 720 comprises the EML2 740. The second emitting part 720 may further comprise at least one of a second HTL (HTL2) 760 disposed between the CGL 680 and the EML2 740, a second ETL (ETL2) 770 disposed between the EML2 740 and the second electrode 530 and an EIL 780 disposed between the ETL2 770 and the second electrode 530. Alternatively, the second emitting part 720 may further comprise a second EBL (EBL2) 765 disposed between the HTL2 760 and the EML2 740 and/or a second HBL (HBL2) 775 disposed between the EML2 740 and the ETL2 770.

The first emitting part 620 and the second emitting part 720 are connected via the CGL 680. The CGL 680 may be a PN-junction CGL that junctions an N-type CGL (N-CGL) 682 with a P-type CGL (P-CGL) 684.

The N-CGL 682 is disposed between the ETL1 670 and the HTL2 760 and the P-CGL 684 is disposed between the N-CGL 682 and the HTL2 760. The N-CGL 682 transports electrons to the EML1 640 of the first emitting part 620 and the P-CGL 684 transport holes to the EML2 740 of the second emitting part 720. In one exemplary aspect, the N-CGL 682 may include any organic compound having the structure of Chemical Formulae 1 to 3.

In this aspect, each of the EML1 640 and the EML2 740 may be blue, green or red emitting material layer. For example, at least one of the EML1 640 and the EML2 740 comprise a first compound H as a host, a second compound TD as delayed fluorescent material and/or a third compound FD as fluorescent or phosphorescent material. For example, the EML1 640 may comprise the first compound, the second compound and the third compound.

When the EML1 640 includes the first compound H, the second compound TD and the third compound FD, the contents of the first compound H may be larger than the contents of the second compound TD, and the contents of the second compound TD is larger than the contents of the third compound FD. In this case, exciton energy can be transferred efficiently from the second compound TD to the third compound FD. As an example, each of the contents of the first to third compounds H, TD and FD in the EML1 640 may be, but is not limited to, about 60 wt % to about 75 wt %, about 20 wt % to about 40 wt % and about 0.1 wt % to about 5 wt %, respectively.

In one exemplary aspect, the EML2 740 may comprise the first compound H as a host having the structure of Chemical Formulae 1 to 3, the second compound TD as delayed fluorescent material and/or the third compound FD as fluorescent or phosphorescent material. Alternatively, the EML2 740 may include another compound that is different from at least one of the second compound TD and the third compound FD in the EML1 640, and thus the EML2 740 may emit light different from the light emitted from the EML1 640 or may have different luminous efficiency different from the luminous efficiency of the EML1 640.

In FIG. 11, each of the EML1 640 and the EML2 740 has a single-layered structure. Alternatively, each of the EML1 640 and the EML2 740, each of which may include the first to third compounds, may have a double-layered structure (FIG. 7) or a triple-layered structure (FIG. 9), respectively.

In the OLED D5, the singlet exciton energy of the second compound TD of delayed fluorescent material is transferred to the third compound FD of fluorescent or phosphorescent material, and the final emission is occurred at the third compound. Accordingly, the OLED D5 can have excellent luminous efficiency and color purity. In addition, the OLED D5 has a double stack structure of blue, green or red emitting material layer, the OLED D5 improve its color sense or optimize its luminous efficiency.

Figure 12:
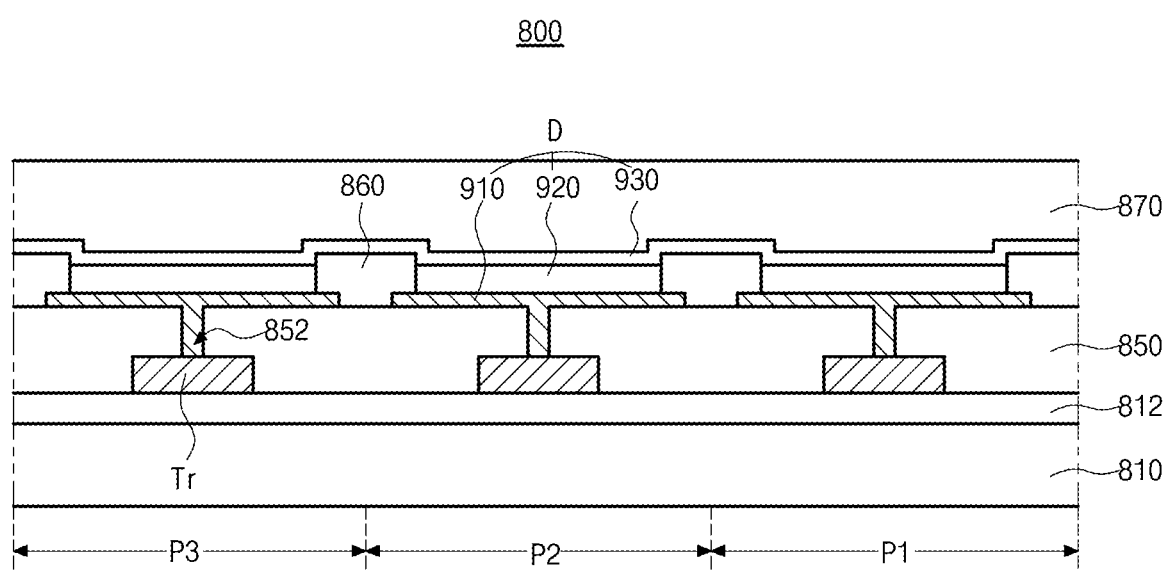
FIG. 12 is a schematic cross-sectional view illustrating an organic light emitting display device in accordance with another exemplary aspect of the present disclosure.

FIG. 12 is a schematic cross-sectional view illustrating an organic light emitting display device in accordance with another exemplary aspect of the present disclosure. As illustrated in FIG. 12, an organic light emitting display device 800 includes a substrate 810 that defines first to third pixel regions P1, P2 and P3, a thin film transistor Tr disposed over the substrate 810 and an OLED D disposed over the thin film transistor Tr and connected to the thin film transistor Tr. As an example, the first pixel region P1 may be a blue pixel region, the second pixel region P2 may be a green pixel region and the third pixel region P3 may be a red pixel region.

The substrate 810 may be a glass substrate or a flexible substrate. For example, the flexible substrate may be any one of a PI substrate, a PES substrate, a PEN substrate, a PET substrate and a PC substrate.

A buffer layer 812 is disposed over the substrate 810 and the thin film transistor Tr is disposed over the buffer layer 812. The buffer layer 812 may be omitted. As illustrated in FIG. 1, the thin film transistor Tr includes a semiconductor layer, a gate electrode, a source electrode and a drain electrode and acts as a driving element.

A passivation layer 850 is disposed over the thin film transistor Tr. The passivation layer 850 has a flat top surface and a drain contact hole 852 that exposes a drain electrode of the thin film transistor Tr.

The OLED D is disposed over the passivation layer 850, and includes a first electrode 910 that is connected to the drain electrode of the thin film transistor Tr, and an emissive layer 920 and a second electrode 930 each of which is disposed sequentially on the first electrode 910. The OLED D is disposed in each of the first to third pixel regions P1, P2 and P3 and emits different light in each pixel region. For example, the OLED D in the first pixel region P1 may emit blue light, the OLED D in the second pixel region P2 may emit green light and the OLED D in the third pixel region P3 may emit red light.

The first electrode 910 is separately formed for each of the first to third pixel regions P1, P2 and P3, and the second electrode 930 corresponds to the first to third pixel regions P1, P2 and P3 and is formed integrally.

The first electrode 910 may be one of an anode and a cathode, and the second electrode 930 may be the other of the anode and the cathode. In addition, one of the first electrode 910 and the second electrode 930 is a transmissive (or semi-transmissive) electrode and the other of the first electrode 910 and the second electrode 930 is a reflective electrode.

For example, the first electrode 910 may be an anode and may include conductive material having a relatively high work function value, i.e., a transparent conductive oxide layer of transparent conductive oxide (TCO). The second electrode 930 may be a cathode and may include conductive material having relatively low work function value, i.e., a metal material layer of low-resistant metal. For example, the first electrode 910 may include any one of ITO, IZO, ITZO, SnO, ZnO, ICO and AZO, and the second electrode 930 may include Al, Mg, Ca, Ag, alloy thereof or combination thereof.

When the organic light emitting display device 800 is a bottom-emission type, the first electrode 910 may have a single-layered structure of a transparent conductive oxide layer.

Alternatively, when the organic light emitting display device 800 is a top-emission type, a reflective electrode or a reflective layer may be disposed under the first electrode 910. For example, the reflective electrode or the reflective layer may include, but is not limited to, Ag or APC alloy. In the OLED D of the top-emission type, the first electrode 910 may have a triple-layered structure of ITO/Ag/ITO or ITO/APC/ITO. Also, the second electrode 930 is thin so as to have light-transmissive (or semi-transmissive) property.

An emissive layer 920 is disposed on the first electrode 910. In one exemplary aspect, the emissive layer 920 may have a single-layered structure of an EML. Alternatively, the emissive layer 920 may include at least one of a HIL, a HTL, and an EBL disposed sequentially between the first electrode 910 and the EML and/or a HBL, an ETL and an EIL disposed sequentially between the EML and the second electrode 930.

In one exemplary aspect, the EML of the emissive layer 930 in the first pixel region P1 of a blue pixel region may comprise a first compound H as a host, a second compound as blue delayed fluorescent material and/or a third compound as blue fluorescent or phosphorescent material. The EML of the emissive layer 930 in the second pixel region P2 of a green pixel region may comprise a first compound H as a host, a second compound as green delayed fluorescent material and/or a third compound as green fluorescent or phosphorescent material. The EML of the emissive layer 930 in the third pixel region P3 of a red pixel region may comprise a first compound H as a host, a second compound as red delayed fluorescent material and/or a third compound as red fluorescent or phosphorescent material. In this case, each of the EMLs in the emissive layers 930 in the first to third pixel regions P1, P2 and P3 may have a single-layered structure, a double-layered structure or a triple-layered structure.

Alternatively, any EMLs in the emissive layers 930 in any of the first to third pixel regions P1, P2 and P3 may include organic compounds other than the first to third compounds.

An encapsulation film 870 is disposed over the second electrode 930 in order to prevent outer moisture from penetrating into the OLED D. The encapsulation film 870 may have, but is not limited to, a triple-layered structure of a first inorganic insulating film, an organic insulating film and a second inorganic insulating film.

A bank layer 860 is disposed over the passivation layer 850 in order to cover edges of the first electrode 910. Moreover, the organic light emitting display device 800 may have a polarizer in order to decrease external light reflection. For example, the polarizer may be a circular polarizer. When the organic light emitting display device 800 is a bottom-emission type, the polarizer may be disposed under the substrate 810. Alternatively, when the organic light emitting display device 800 is a top emission type, the polarizer may be disposed over the encapsulation film 870.

Figure 13:
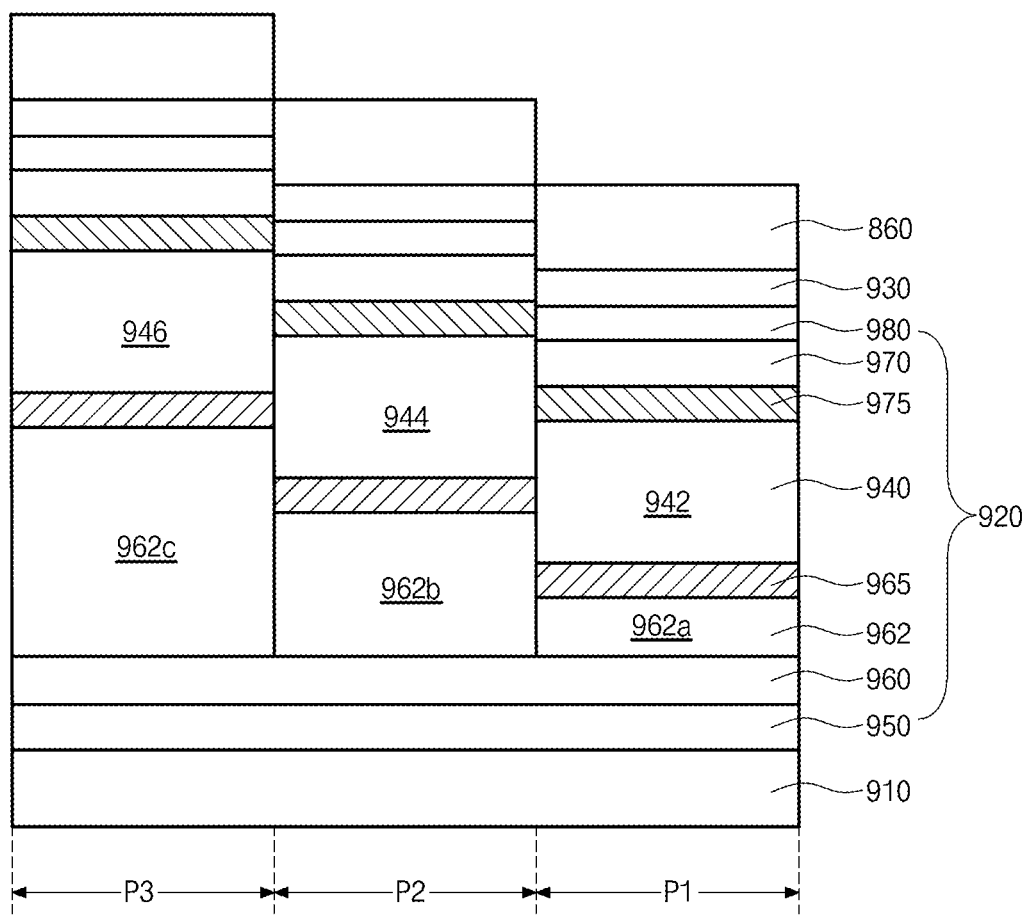
FIG. 13 is a schematic cross-sectional view illustrating an OLED in accordance with still another exemplary aspect of the present disclosure.

FIG. 13 is a schematic cross-sectional view illustrating an OLED in accordance with still another exemplary aspect of the present disclosure. As illustrated in FIG. 13, the OLED D6 comprises a first electrode 910, a second electrode 930 facing the first electrode 910 and an emissive layer 920 disposed between the first and second electrodes 910 and 930.

The first electrode 910 may be an anode and the second electrode 930 may be a cathode. As an example, the first electrode 910 may be a reflective electrode and the second electrode 930 may be a transmissive (or semi-transmissive) electrode.

The emissive layer 920 comprises an EML 940. The emissive layer 930 may comprise at least one of a HTL 960 disposed between the first electrode 910 and the EML 940 and an ETL 970 disposed between the second electrode 940 and the EML 940. Also, the emissive layer may further comprise at least one of a HIL 950 disposed between the first electrode 910 and the HTL 960 and an EIL 980 disposed between the second electrode 930 and the ETL 970. Alternatively, the emissive layer 920 may further comprise an EBL 965 disposed between the HTL 960 and the EML 940 and/or a HBL 975 disposed between the EML 940 and the ETL 970.

In addition, the emissive layer 920 may further comprise an auxiliary hole transport layer (auxiliary HTL) 962 disposed between the HTL 960 and the EBL 965. The auxiliary HTL 9620 may comprise a first auxiliary HTL 962a located in the first pixel region P1, a second auxiliary HTL 962b located in the second pixel region P2 and a third auxiliary HTL 962c located in the third pixel region P3.

The first auxiliary HTL 962a has a first thickness, the second auxiliary HTL 962b has a second thickness and the third auxiliary HTL 962c has a third thickness. The first thickness is less than the second thickness, and the second thickness is less than the third thickness. Accordingly, the OLED D6 has a micro-cavity structure.

Owing to the first to third auxiliary HTLs 962a, 962b and 962c having different thickness to each other, the distance between the first electrode 910 and the second electrode 930 in the first pixel region P1 emitting light in the first wavelength range (blue light) is smaller than the distance between the first electrode 910 and the second electrode 930 in the second pixel region P2 emitting light in the second wavelength (green light). In addition, the distance between the first electrode 910 and the second electrode 930 in the second pixel region P2 emitting light in the second wavelength is smaller than the distance between the first electrode 910 and the second electrode 930 in the third pixel region P3 emitting light in the third wavelength range (red light). Accordingly, the OLED D6 has improved luminous efficiency.

In FIG. 13, the first auxiliary HTL 962a is located in the first pixel region P1. Alternatively, the OLED D6 may implement the micro-cavity structure without the first auxiliary HTL 962a. In addition, a capping layer may be disposed over the second electrode in order to improve out-coupling of the light emitted from the OLED D6.

The EML 940 comprises a first EML (EML1) 942 located in the first pixel region P1, a second EML (EML2) 944 located in the second pixel region P2 and a third EML (EML3) 946 located in the third pixel region P3. Each of the EML1 942, the EML2 944 and the EML3 946 may be a blue EML, a green EML and a red EML, respectively.

In one exemplary aspect, the EML1 942 located in the first pixel region P1 may comprise a first compound H of a host, a second compound TD of blue delayed fluorescent material and/or a third compound FD of blue fluorescent or phosphorescent material. The EML2 944 located in the second pixel region P2 may comprise a first compound H of a host, a second compound TD of green delayed fluorescent material and/or a third compound FD of green fluorescent or phosphorescent material. The EML3 946 located in the third pixel region P3 may comprise a first compound H of a host, a second compound TD of red delayed fluorescent material and/or a third compound FD of red fluorescent or phosphorescent material. The first compound H in the EML1 942, the EML2 944 and the EML3 946 may be any organic compound having the structure of Chemical Formulae 1 to 3.

When the EML1 942, the EML2 944 and the EML3 946 include the first compound H, the second compound TD and the third compound FD, the contents of the first compound H may be larger than the contents of the second compound TD, and the contents of the second compound TD is larger than the contents of the third compound FD. In this case, exciton energy can be transferred efficiently from the second compound TD to the third compound FD. As an example, each of the contents of the first to third compounds H, TD and FD in each of the EML1 942, the EML2 944 and the EML3 946 may be, but is not limited to, about 60 wt % to about 75 wt %, about 20 wt % to about 40 wt % and about 0.1 wt % to about 5 wt %, respectively.

While each of the EML1 942, the EML2 944 and the EML3 946 has a single-layered structure in FIG. 13, each of the EML1 942, the EML2 944 and the EML3 946 may have a double-layered structure (FIG. 7) or a triple-layered structure (FIG. 9), respectively.

In another exemplary aspect, at least one of the EML1 942, the EML2 944 and the EML3 946 may comprise the first compound H, the second compound TD and the third compound while the rest of the EML1 942, the EML2 944 and the EML3 946 may comprise other organic compound. In this case, the EML1 942, the EML2 944 and the EML3 946 having the first to third compounds may have a single-layered structure, a double-layered structure or a triple-layered structure.

For example, the first EML1 942 located in the first pixel region P1 may comprise a first compound H of a host, a second compound TD of blue delayed fluorescent material and/or a third compound FD of blue fluorescent or phosphorescent material. The EML2 944 located in the second pixel region P2 may comprise a host and a green dopant, and the EML3 946 located in the third pixel region P3 may comprise a host and a red dopant. The host of the EML1 942 and/or the EML3 944 may comprise the first compound H. Each of the green dopant or the red dopant may comprise at least one of green or red phosphorescent material, green or red fluorescent material and green or red delayed fluorescent material.

The OLED D6 emits blue light, green light and red light in each of the first to third pixel regions P1, P2 and P3 so that the organic light emitting display device 800 (FIG. 12) may implement a full-color image.

The organic light emitting display device 800 may further comprise a color filter layer corresponding to the first to third pixel regions P1, P2 and P3 for improving color purity of the light emitted from the OLED D. As an example, the color filter layer may comprise a first color filter layer (blue color filter layer) corresponding to the first pixel region P1, the second color filter layer (green color filter layer) corresponding to the second pixel region P2 and the third color filter layer (red color filter layer) corresponding to the third pixel region P3.

When the organic light emitting display device 800 is a bottom-emission type, the color filter layer may be disposed between the OLED D and the substrate 810. Alternatively, when the organic light emitting display device 800 is a top-emission type, the color filter layer may be disposed over the OLED D.

Figure 14:
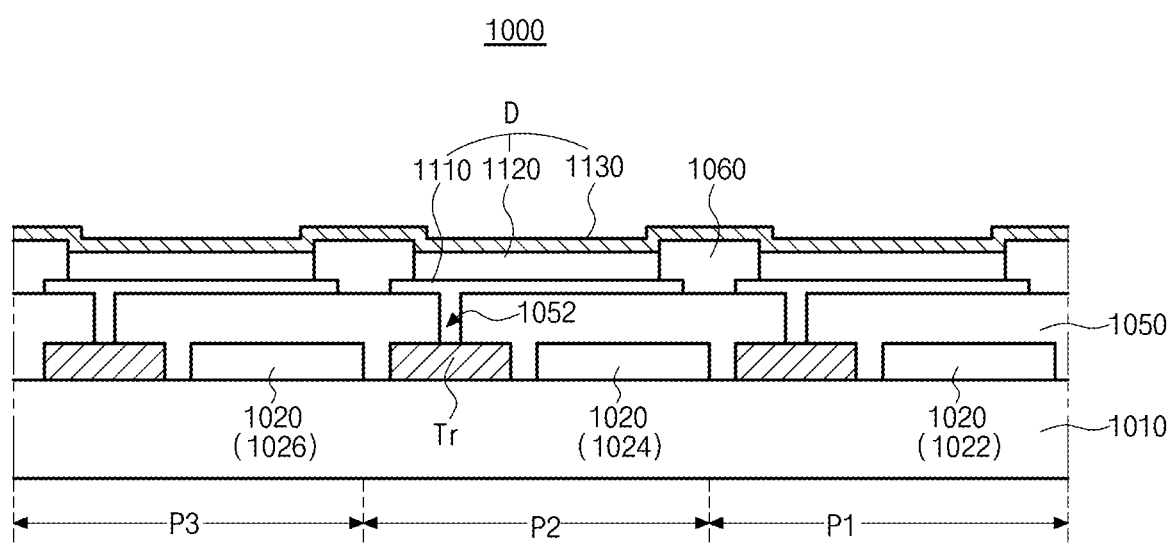
FIG. 14 is a schematic cross-sectional view illustrating an organic light emitting display device in accordance with still another exemplary aspect of the present disclosure.

FIG. 14 is a schematic cross-sectional view illustrating an organic light emitting display device in accordance with still another exemplary aspect of the present disclosure. As illustrated in FIG. 14, the organic light emitting display device 1000 comprise a substrate 1010 defining a first pixel region P1, a second pixel region P2 and a third pixel region P3, a thin film transistor Tr disposed over the substrate 1010, an OLED D disposed over the thin film transistor Tr and connected to the thin film transistor Tr and a color filter layer 1020 corresponding to the first to third pixel regions P1, P2 and P3. As an example, the first pixel region P1 may be a blue pixel region, the second pixel region P2 may be a green pixel region and the third pixel region P3 may be a red pixel region.

The substrate 1010 may be a glass substrate or a flexible substrate. For example, the flexible substrate may be any one of a PI substrate, a PES substrate, a PEN substrate, a PET substrate and a PC substrate. The thin film transistor Tr is located over the substrate 1010. Alternatively, a buffer layer may be disposed over the substrate 1010 and the thin film transistor Tr may be disposed over the buffer layer. As illustrated in FIG. 1, the thin film transistor Tr includes a semiconductor layer, a gate electrode, a source electrode and a drain electrode and acts as a driving element.

The color filter layer 1020 is located over the substrate 1010. As an example, the color filter layer 1020 may comprise a first color filter layer 1022 corresponding to the first pixel region P1, a second color filter layer 1024 corresponding to the second pixel region P2 and a third color filter layer 1026 corresponding to the third pixel region P3. The first color filter layer 1022 may be a blue color filter layer, the second color filter layer 1024 may be a green color filter layer and the third color filter layer 1026 may be a red color filter layer. For example, the first color filter layer 1022 may comprise at least one of blue dye or blue pigment, the second color filter layer 1024 may comprise at least one of green dye or green pigment and the third color filter layer 1026 may comprise at least one of red dye or red pigment.

A passivation layer 1050 is disposed over the thin film transistor Tr and the color filter layer 1020. The passivation layer 1050 has a flat top surface and a drain contact hole 1052 that exposes a drain electrode of the thin film transistor Tr.

The OLED D is disposed over the passivation layer 1050 and corresponds to the color filter layer 1020. The OLED D includes a first electrode 1110 that is connected to the drain electrode of the thin film transistor Tr, and an emissive layer 1120 and a second electrode 1130 each of which is disposed sequentially on the first electrode 1110. The OLED D emits white light in the first to third pixel regions P1, P2 and P3.

The first electrode 1110 is separately formed for each of the first to third pixel regions P1, P2 and P3, and the second electrode 1130 corresponds to the first to third pixel regions P1, P2 and P3 and is formed integrally.

The first electrode 1110 may be one of an anode and a cathode, and the second electrode 1130 may be the other of the anode and the cathode. In addition, the first electrode 1110 may be a transmissive (or semi-transmissive) electrode and the second electrode 1130 may be a reflective electrode.

For example, the first electrode 1110 may be an anode and may include conductive material having a relatively high work function value, i.e., a transparent conductive oxide layer of transparent conductive oxide (TCO). The second electrode 1130 may be a cathode and may include conductive material having relatively low work function value, i.e., a metal material layer of low-resistant metal. For example, the transparent conductive oxide layer of the first electrode 1110 may include any one of ITO, IZO, ITZO, SnO, ZnO, ICO and AZO, and the second electrode 1130 may include Al, Mg, Ca, Ag, alloy thereof (ex. Mg—Ag) or combination thereof.

The emissive layer 1120 is disposed on the first electrode 1110. The emissive layer 1120 includes at least two emitting parts emitting different colors. Each of the emitting part may have a single-layered structure of an EML. Alternatively, each of the emitting parts may include at least one of a HIL, a HTL, and an EBL, a HBL, an ETL and an EIL. In addition, the emissive layer may further comprise a CGL disposed between the emitting parts.

At least one of the at least two emitting parts may comprise a first compound H of a host having the structure of Chemical Formulae 1 to 3, a second compound TD of delayed fluorescent material and/or a third compound FD of fluorescent or phosphorescent material.

A bank layer 1060 is disposed on passivation layer 1050 in order to cover edges of the first electrode 1110. The bank layer 1060 corresponds to each of the first to third pixel regions P1, P2 and P3 and exposes a center of the first electrode 1110. As described above, since the OLED D emits white light in the first to third pixel regions P1, P2 and P3, the emissive layer 1120 may be formed as a common layer without being separated in the first to third pixel regions P1, P2 and P3. The bank layer 1060 is formed to prevent current leakage from the edges of the first electrode 1110, and the bank layer 1060 may be omitted.

Moreover, the organic light emitting display device 1000 may further comprise an encapsulation film disposed on the second electrode 1130 in order to prevent outer moisture from penetrating into the OLED D. In addition, the organic light emitting display device 1000 may further comprise a polarizer disposed under the substrate 1010 in order to decrease external light reflection.

In the organic light emitting display device 1000 in FIG. 14, the first electrode 1110 is a transmissive electrode, the second electrode 1130 is a reflective electrode, and the color filter layer 102 is disposed between the substrate 1010 and the OLED D. That is, the organic light emitting display device 1000 is a bottom-emission type. Alternatively, the first electrode 1110 may be a reflective electrode, the second electrode 1120 may be a transmissive electrode (or semi-transmissive electrode) and the color filter layer 1020 may be disposed over the OLED D in the organic light emitting display device 1000.

In the organic light emitting display device 1000, the OLED D located in the first to third pixel regions P1, P2 and P3 emits white light, and the white light passes through each of the first to third pixel regions P1, P2 and P3 so that each of a blue color, a green color and a red color is displayed in the first to third pixel regions P1, P2 and P3, respectively.

A color conversion film may be disposed between the OLED D and the color filter layer 1020. The color conversion film corresponds to the first to third pixel regions P1, P2 and P3, and comprises a blue color conversion film, a green color conversion film and a red color conversion film each of which can convert the white light emitted from the OLED D into blue light, green light and red light, respectively. For example, the color conversion film may comprise quantum dots. Accordingly, the organic light emitting display device 1000 may further enhance its color purity. Alternatively, the color conversion film may displace the color filter layer 1020.

Figure 15:
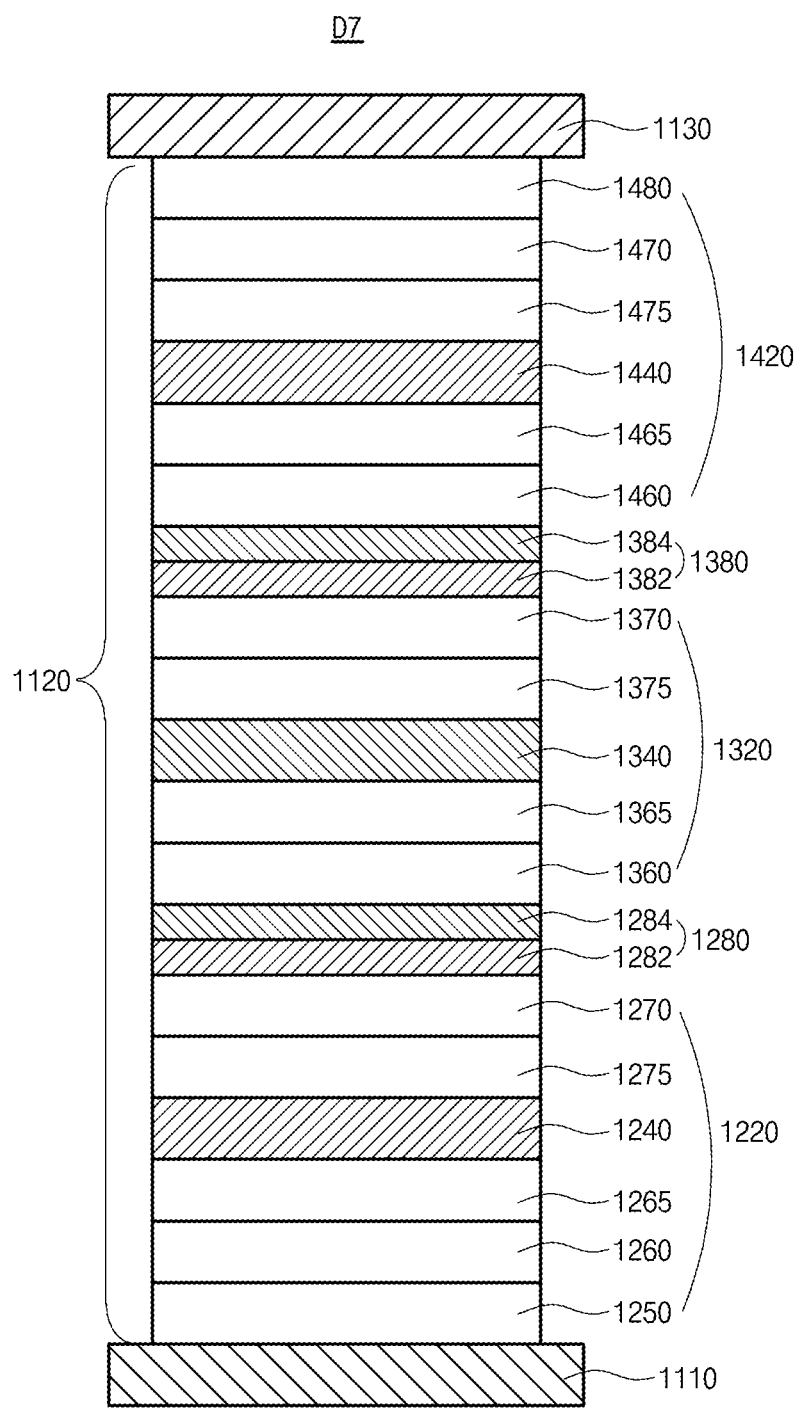
FIG. 15 is a schematic cross-sectional view illustrating an OLED in accordance with still another exemplary aspect of the present disclosure.

FIG. 15 is a schematic cross-sectional view illustrating an OLED in accordance with still another exemplary aspect of the present disclosure. As illustrated in FIG. 15, the OLED D7 comprises first and second electrodes 1110 and 1120 facing each other and an emissive layer 1120 disposed between the first and second electrodes 1110 and 1120. The first electrode 1110 may be an anode and the second electrode 1120 may be a cathode. For example, the first electrode 1100 may be a transmissive electrode and the second electrode 1120 may be a reflective electrode.

The emissive layer 1120 includes a first emitting part 1220 comprising a first EML (EML1) 1240, a second emitting part 1320 comprising a second EML (EML2) 1340 and a third emitting part 1420 comprising a third EML (EML3) 1440. In addition, the emissive layer 1120 may further comprise a first charge generation layer (CGL1) 1280 disposed between the first emitting part 1220 and the second emitting part 1320 and a second charge generation layer (CGL2) 1380 disposed between the second emitting part 1320 and the third emitting part 1420. Accordingly, the first emitting part 1220, the CGL1 1280, the second emitting part 1320, the CGL2 1380 and the third emitting part 1420 are disposed sequentially on the first electrode 1110.

The first emitting part 1220 may further comprise at least one of a first HTL (HTL1) 1260 disposed between the first electrode 1110 and the EML1 1240, a HIL 1250 disposed between the first electrode 1110 and the HTL1 1260 and a first ETL (ETL1) 1270 disposed between the EML1 1240 and the CGL1 1280. Alternatively, the first emitting part 1220 may further comprise a first EBL (EBL1) 1265 disposed between the HTL1 1260 and the EML1 1240 and/or a first HBL (HBL1) 1275 disposed between the EML1 1240 and the ETL1 1270.

The second emitting part 1320 may further comprise at least one of a second HTL (HTL2) 1360 disposed between the CGL1 1280 and the EML2 1340, a second ETL (ETL2) 1370 disposed between the EML2 1340 and the CGL2 1380. Alternatively, the second emitting part 1320 may further comprise a second EBL (EBL2) 1365 disposed between the HTL2 1360 and the EML2 1340 and/or a second HBL (HBL2) 1375 disposed between the EML2 1340 and the ETL2 1370.

The third emitting part 1420 may further comprise at least one of a third HTL (HTL3) 1460 disposed between the CGL2 1380 and the EML3 1440, a third ETL (ETL3) 1470 disposed between the EML3 1440 and the second electrode 1130 and an EIL 1480 disposed between the ETL3 1470 and the second electrode 1130. Alternatively, the third emitting part 1420 may further comprise a third EBL (EBL3) 1465 disposed between the HTL3 1460 and the EML3 1440 and/or a third HBL (HBL3) 1475 disposed between the EML3 1440 and the ETL3 1470.

The CGL1 1280 is disposed between the first emitting part 1220 and the second emitting part 1320. That is, the first emitting part 1220 and the second emitting part 1320 are connected via the CGL1 1280. The CGL1 1280 may be a PN-junction CGL that junctions a first N-type CGL (N-CGL1) 1282 with a first P-type CGL (P-CGL1) 1284.

The N-CGL1 1282 is disposed between the ETL1 1270 and the HTL2 1360 and the P-CGL1 1284 is disposed between the N-CGL1 1282 and the HTL2 1360. The N-CGL1 1282 transports electrons to the EML1 1240 of the first emitting part 1220 and the P-CGL1 1284 transport holes to the EML2 1340 of the second emitting part 1320.

The CGL2 1380 is disposed between the second emitting part 1320 and the third emitting part 1420. That is, the second emitting part 1320 and the third emitting part 1420 are connected via the CGL2 1380. The CGL2 1380 may be a PN-junction CGL that junctions a second N-type CGL (N-CGL2) 1382 with a second P-type CGL (P-CGL2) 1384.

The N-CGL2 1382 is disposed between the ETL2 1370 and the HTL3 1460 and the P-CGL2 1384 is disposed between the N-CGL2 1382 and the HTL3 1460. The N-CGL2 1382 transports electrons to the EML2 1340 of the second emitting part 1320 and the P-CGL2 1384 transport holes to the EML3 1440 of the third emitting part 1420. In one exemplary aspect, at least one of the N-CGL1 1282 and the N-CGL2 1382 may include any organic compound having the structure of Chemical Formulae 1 to 3.

In this aspect, one of the first to third EMLs 1240, 1340 and 1440 may be a blue EML, another of the first to third EMLs 1240, 1340 and 1440 may be a green EML and the third of the first to third EMLs 1240, 1340 and 1440 may be a red EML.

As an example, the EML1 1240 may be a blue EML, the EML2 1340 may be a green EML and the EML3 1440 may be a red EML. Alternatively, the EML1 1240 may be a red EML, the EML2 1340 may be a green EML and the EML3 1440 may be a blue EML1. Hereinafter, the OLED D6 where the EML1 1240 is a blue EML, the EML2 1340 is a green EML and the EML3 1440 is a red EML will be described.

As described below, at least one of the EML1 1240, the EML2 1340 and the EML3 1440 may comprise a first compound H, a second compound TD and/or a third compound FD. The EMLs 1240, 1340 and 1440 including the first to third compounds may have a single-layered structure, a double-layered structure or a triple-layered structure.

The EML1 1240 may comprise a first compound H of a host which may an organic compound having the structure of Chemical Formulae 1 to 3, a second compound TD of blue delayed fluorescent material and/or a third compound FD of blue fluorescent or phosphorescent material. Alternatively, the EML1 1240 may comprise a host and other blue dopant. The host may comprise the first compound and other blue dopant may comprise at least one of blue phosphorescent material, blue fluorescent material and blue delayed fluorescent material.

The EML2 1340 may comprise a first compound H of a host which may an organic compound having the structure of Chemical Formulae 1 to 3, a second compound TD of green delayed fluorescent material and/or a third compound FD of green fluorescent or phosphorescent material. Alternatively, the EML2 1340 may comprise a host and other green dopant. The host may comprise the first compound and other green dopant may comprise at least one of green phosphorescent material, green fluorescent material and green delayed fluorescent material.

The EML3 1340 may comprise a first compound H of a host which may an organic compound having the structure of Chemical Formulae 1 to 3, a second compound TD of red delayed fluorescent material and/or a third compound FD of red fluorescent or phosphorescent material. Alternatively, the EML3 1440 may comprise a host and other red dopant. The host may comprise the first compound and other red dopant may comprise at least one of red phosphorescent material, red fluorescent material and red delayed fluorescent material.

When each of the EML1 1240, the EML2 1340 and the EML3 1440 includes the first compound H, the second compound TD and the third compound FD, the contents of the first compound H may be larger than the contents of the second compound TD, and the contents of the second compound TD is larger than the contents of the third compound FD. In this case, exciton energy can be transferred efficiently from the second compound TD to the third compound FD. As an example, each of the contents of the first to third compounds H, TD and FD in each of the EML1 1240, the EML2 1340 and the EML3 1440 may be, but is not limited to, about 60 wt % to about 75 wt %, about 20 wt % to about 40 wt % and about 0.1 wt % to about 5 wt %, respectively.

The OLED D7 emits white light in each of the first to third pixel regions P1, P2 and P3 and the white light passes though the color filter layer 1020 (FIG. 14) correspondingly disposed in the first to third pixel regions P1, P2 and P3. Accordingly, the OLED D7 can implement a full-color image.

Figure 16:
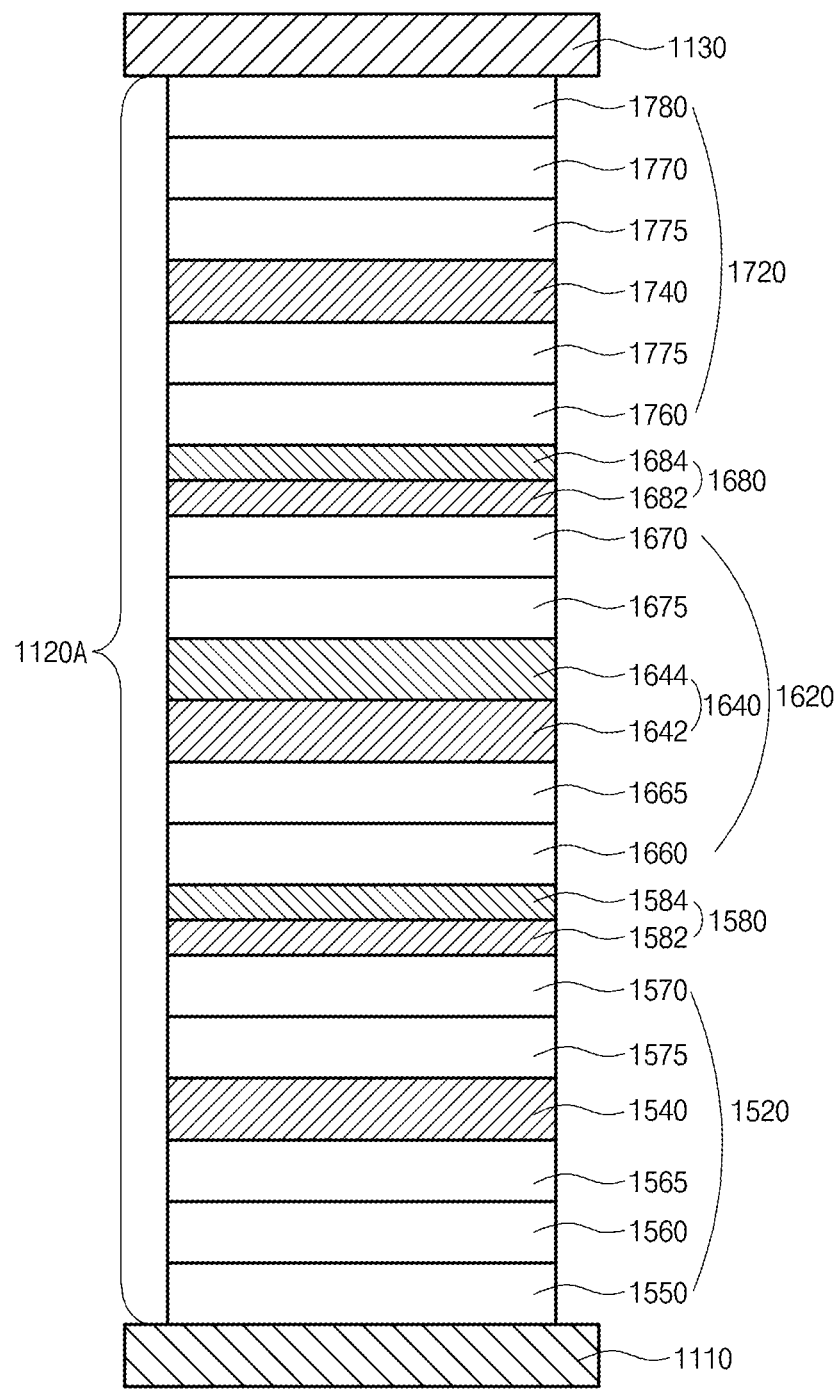
FIG. 16 is a schematic cross-sectional view illustrating an OLED in accordance with still another exemplary aspect of the present disclosure.

FIG. 16 is a schematic cross-sectional view illustrating an OLED in accordance with still another exemplary aspect of the present disclosure. As illustrated in FIG. 16, the OLED D8 comprises first and second electrodes 1110 and 1120 facing each other and an emissive layer 1120A disposed between the first and second electrodes 1110 and 1120. The first electrode 1110 may be an anode and the second electrode 1120 may be a cathode. For example, the first electrode 1100 may be a transmissive electrode and the second electrode 1120 may be a reflective electrode.

The emissive layer 1120A includes a first emitting part 1520 comprising an EML1 1540, a second emitting part 1620 comprising an EML2 1640 and a third emitting part 1720 comprising an EML3 1740. In addition, the emissive layer 1120A may further comprise a CGL1 1580 disposed between the first emitting part 1520 and the second emitting part 1620 and a CGL2 1680 disposed between the second emitting part 1620 and the third emitting part 1720. Accordingly, the first emitting part 1520, the CGL1 1580, the second emitting part 1620, the CGL2 1680 and the third emitting part 1720 are disposed sequentially on the first electrode 1110.

The first emitting part 1520 may further comprise at least one of a HTL1 1560 disposed between the first electrode 1110 and the EML1 1540, a HIL 1550 disposed between the first electrode 1110 and the HTL1 1560 and an ETL1 1570 disposed between the EML1 1540 and the CGL1 1580. Alternatively, the first emitting part 1520 may further comprise an EBL1 1565 disposed between the HTL1 1560 and the EML1 1540 and/or a HBL1 1575 disposed between the EML1 1540 and the ETL1 1570.

The EML2 1640 of the second emitting part 1620 comprises a lower EML 1642 and an upper EML 1644. The lower EML 1642 is located adjacently to the first electrode 1110 and the upper EML 1644 is located adjacently too the second electrode 1130. In addition, the second emitting part 1620 may further comprise at least one of a HTL2 1660 disposed between the CGL1 1580 and the EML2 1640, an ETL2 1670 disposed between the EML2 1640 and the CGL2 1680. Alternatively, the second emitting part 1620 may further comprise an EBL2 1665 disposed between the HTL2 1660 and the EML2 1640 and/or a HBL2 1675 disposed between the EML2 1640 and the ETL2 1670.

The third emitting part 1720 may further comprise at least one of a HTL3 1760 disposed between the CGL2 1680 and the EML3 1740, an ETL3 1770 disposed between the EML3 1740 and the second electrode 1130 and an EIL 1780 disposed between the ETL3 1770 and the second electrode 1130. Alternatively, the third emitting part 1720 may further comprise an EBL3 1765 disposed between the HTL3 1760 and the EML3 1740 and/or a HBL3 1775 disposed between the EML3 1740 and the ETL3 1770.

The CGL1 1380 is disposed between the first emitting part 1520 and the second emitting part 1620. That is, the first emitting part 1520 and the second emitting part 1620 are connected via the CGL1 1580. The CGL1 1580 may be a PN-junction CGL that junctions an N-CGL1 1582 with a P-CGL1 1584. The N-CGL1 1582 is disposed between the ETL1 1570 and the HTL2 1660 and the P-CGL1 1584 is disposed between the N-CGL1 1582 and the HTL2 1560.

The CGL2 1680 is disposed between the second emitting part 1620 and the third emitting part 1720. That is, the second emitting part 1620 and the third emitting part 1720 are connected via the CGL2 1680. The CGL2 1680 may be a PN-junction CGL that junctions an N-CGL2 1682 with a P-CGL2 1684. The N-CGL2 1682 is disposed between the ETL2 1570 and the HTL3 1760 and the P-CGL2 1684 is disposed between the N-CGL2 1682 and the HTL3 1760. In one exemplary aspect, at least one of the N-CGL1 1582 and the N-CGL2 1682 may include any organic compound having the structure of Chemical Formulae 1 to 3.

As described below, at least one of the EML1 1540, the EML2 1640 and the EML3 1740 may comprise a first compound H, a second compound TD and/or a third compound FD. The EMLs 1540, 1640 and 1740 including the first to third compounds may have a single-layered structure, a double-layered structure or a triple-layered structure.

In this aspect, each of the EML1 1540 and the EML3 1740 may be a blue EML. In an exemplary aspect, each of the EML1 1540 and the EMl3 1740 may comprise a first compound H of a host and a second compound TD of blue delayed fluorescent material and/or a third compound FD of blue fluorescent or phosphorescent material. Alternatively, at least one of the EML1 1540 and the EML3 1740 may comprise a host and other blue dopant. The host may comprise the first compound and the other blue dopant may comprise at least one of blue phosphorescent material, blue fluorescent material and blue delayed fluorescent material. The first to third compounds in one of the EML1 1540 and the EML3 1740 may be the same as or different from the host and the blue dopant in the other of the EML1 1540 and the EML3 1740. As an example, the dopant in the EML1 1540 may be different from the dopant in the EML3 1740 in terms of luminous efficiency and/or emission wavelength.

One of the lower EML 1642 and the upper EML 1644 in the EML2 1640 may be a green EML and the other of the lower EML 1642 and the upper EML 1644 in the EML2 1640 may be a red EML. The green EML and the red EML is sequentially disposed to form the EML2 1640.

In one exemplary aspect, the lower EML 1642 as the green EML may comprise a first compound H of a host, and a second compound TD of green delayed fluorescent material and/or a third compound FD of green fluorescent or phosphorescent material. Alternatively, the lower EML 1642 as the green EML may comprise a host and other green dopant. The host may comprise the first compound H and the other green dopant may comprise at least one of green phosphorescent material, green fluorescent material and green delayed fluorescent material.

In addition, the upper EML 1644 as the red EML may comprise a first compound H of a host, and a second compound TD of red delayed fluorescent material and/or a third compound FD of red fluorescent or phosphorescent material. Alternatively, the upper EML 1644 as the red EML may comprise a host and other red dopant. The host may comprise the first compound H and the other red dopant may comprise at least one of red phosphorescent material, red fluorescent material and red delayed fluorescent material.

When each of the EML1 1540, the EML2 1640 and the EML3 1740 includes the first compound H, the second compound TD and the third compound FD, the contents of the first compound H may be larger than the contents of the second compound TD, and the contents of the second compound TD is larger than the contents of the third compound FD. In this case, exciton energy can be transferred efficiently from the second compound TD to the third compound FD. As an example, each of the contents of the first to third compounds H, TD and FD in each of the EML1 1540, the EML2 1640 and the EML3 1740 may be, but is not limited to, about 60 wt % to about 75 wt %, about 20 wt % to about 40 wt % and about 0.1 wt % to about 5 wt %, respectively.

The OLED D8 emits white light in each of the first to third pixel regions P1, P2 and P3 and the white light passes though the color filter layer 1020 (FIG. 14) correspondingly disposed in the first to third pixel regions P1, P2 and P3. Accordingly, the OLED D8 can implement a full-color image.

In FIG. 16, the OLED D8 has a three-stack structure including the first to three emitting parts 1520, 1620 and 1720 which includes the EML1 1540 and the EML3 1740 as a blue EML. Alternatively, the OLED D8 may have a two-stack structure where one of the first emitting part 1520 and the third emitting part 1720 each of which includes the EML1 1540 and the EML3 1740 as a blue EML is omitted.

Synthesis Example 1: Synthesis of Compound 1-1

(1) Synthesis of Intermediate B

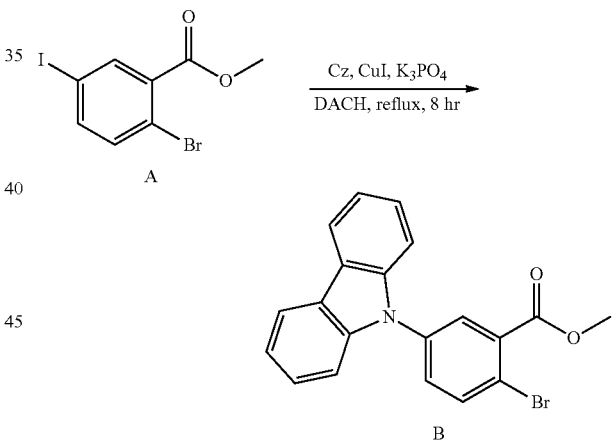

Compound A (4.48 g, 0.013 mol), carbazole (2.0 g, 0.012 mol) and $K_3PO_4$ dissolved in toluene (60 mL) were placed into a reactor, and then the solution was stirred for 20 minutes under nitrogen atmosphere. CuI (460 mg, 20 mol %) and (±)-trans-1,2-diaminocyclohexane (DACH, 0.72 mL, 50 mol %) was added into the reactor, and then the solution was stirred at 110° C. for 8 hours. After the temperature was cooled down to a room temperature, the reaction solvent was removed, and then the obtained crude product was purified with a column chromatography to give a white solid Intermediate B (1.9 g, yield: 42%).

$^1$H NMR (500 MHz, CDCl$_3$): δ (ppm) 8.13 (d, J=7.9 Hz, 2H), 8.02 (d, J=2.4 Hz, 1H), 7.89 (d, J=8.5 Hz, 1H), 7.55 (dd, J=8.5, 2.7 Hz, 1H), 7.42 (ddd, J=8.2, 7.1, 0.9 Hz, 3H), 7.37 (d, J=8.2 Hz, 3H), 7.33-7.28 (m, 2H), 3.94 (s, 3H).

(2) Synthesis of Intermediate C

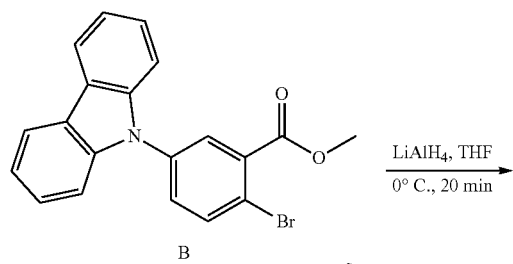

LiAlH₄ (0.22 g, 0.006 mol) dissolved in THF (10 mL) were placed into a reactor under nitrogen atmosphere, and then the solution was cooled down to 0° C. The intermediate B (2.0 g, 0.005 mol) dissolved in THF (15 ML) was added slowly drop wise into the solution. After stirring at the same temperature for 20 minutes, the solution was extracted with ethyl acetate to remove the solvent. The obtained crude product was purified with a column chromatography to give a white solid Intermediate C (1.7 g, yield: 92%).

¹H NMR (500 MHz, CDCl₃): δ (ppm) 8.13 (dt, J=7.9, 1.0 Hz, 2H), 7.75 (d, J=8.2 Hz, 1H), 7.73 (d, J=2.4 Hz, 1H), 7.43-7.35 (m, 5H), 7.31-7.26 (m, 2H), 4.84 (d, J=6.1 Hz, 2H), 2.05 (t, J=6.1 Hz, 1H).

(3) Synthesis of Intermediate D

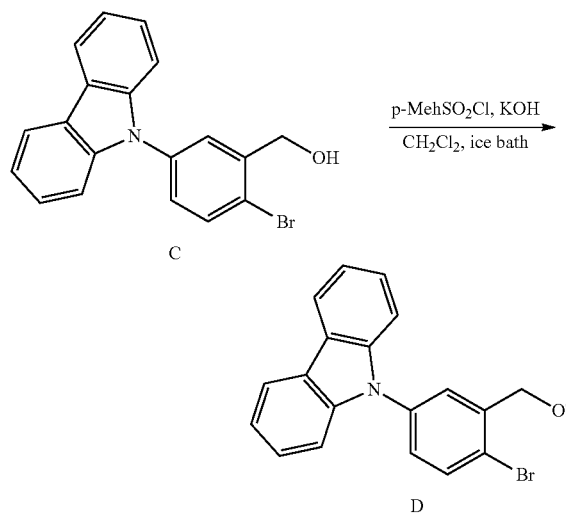

The intermediate C (1.8 g, 0.005 mol) and KOH (2.3 g, 0.041 mol) dissolved in methylene chloride (15 mL) was placed into a reactor, and then the temperature was cooled down to 0° C. with stirring. P-toluene-sulfonyl chloride (1.17 g, 0.006 mol) dissolved in methylene chloride (10 mL) was added slowly drop wise into the reaction solution. After stirring at the same temperature for 20 minutes, the reaction mixture was stirred again at a room temperature for 4 hours, and then was extracted with CH₂Cl₂ to remove the solvent. The obtained product was purified with a column chromatography to give a white solid Intermediate D (2.2 g, yield: 85%)

¹H NMR (500 MHz, CDCl₃): δ (ppm) 8.13 (d, J=7.6 Hz, 2H), 7.81 (d, J=8.2 Hz, 2H), 7.73 (d, J=8.5 Hz, 1H), 7.54 (d, J=2.4 Hz, 1H), 7.44-7.38 (m, 3H), 7.33-7.29 (m, 4H), 7.29-7.27 (m, 2H), 5.23 (s, 2H), 2.35 (s, 3H).

(4) Synthesis of Compound 1-1

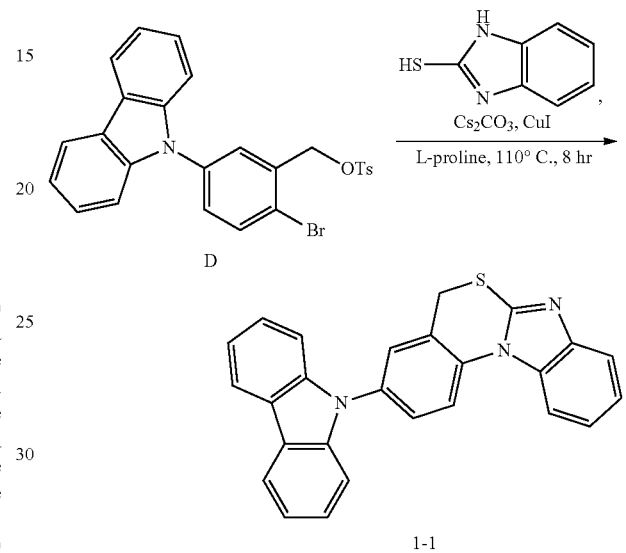

1H-benzo[d]imdiazole-2-thiol (0.5 g, 0.003 mol), CuI (63 mg, 10 mol %) and Cs₂CO₃ (2.17 g, 0.007 mol) dissolved in DMF (20 mL) were placed into a reactor, and then the solution was stirred for 20 minutes under nitrogen atmosphere. The intermediate D (1.68 g, 0.003 mol) and L-proline (77 mg, 20 mol %) dissolved in DMF (20 mL) were added slowly drop wise into the reaction solution. After stirring at 160° C. for 8 hours, the reactor was cooled down to a room temperature, and then the solution was extracted with EtOAc to remove the solvent. The obtained crude product was purified with a column chromatography to give a white solid Compound 1-1 (1.2 g, yield: 89%).

¹H NMR (500 MHz, CDCl₃): δ (ppm) 8.18-8.14 (m, 2H), 8.07 (d, J=8.5 Hz, 1H), 7.91-7.86 (m, 1H), 7.82-7.77 (m, 1H), 7.68 (dd, J=8.5, 2.1 Hz, 1H), 7.61 (d, J=2.1 Hz, 1H), 7.47-7.41 (m, 4H), 7.39-7.35 (m, 2H), 7.34-7.29 (m, 2H), 4.10 (s, 2H).

Synthesis Example 2: Synthesis of Compound 1-2

(1) Synthesis of Intermediate E

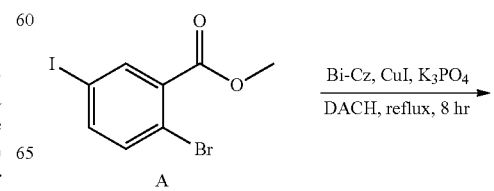

-continued

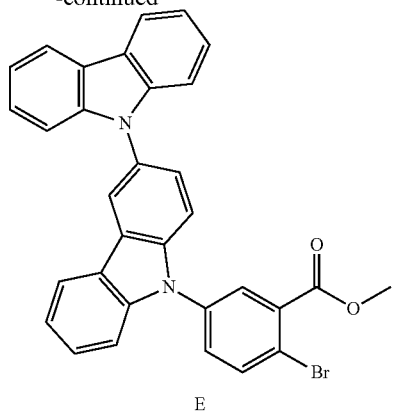

E

Compound A (4.50 g, 0.013 mol) and 9H-3,9'-bicarbazole (4.0 g, 0.012 mol) were reacted in the same manner as the synthesis of the intermediate B to finally give a white solid Intermediate E (3.0 g, yield: 46%).

$^1$H NMR (500 MHz, CDCl$_3$): δ (ppm) 8.29-8.27 (m, 1H), 8.20-8.16 (m, 2H), 8.12-8.10 (m, 1H), 7.95 (d, J=8.5 Hz, 1H), 7.64 (dd, J=8.2, 2.6 Hz, 1H), 7.56 (dd, J=2.1, 1.2 Hz, 2H), 7.50-7.48 (m, 1H), 7.45-7.37 (m, 6H), 7.36-7.27 (m, 3H), 3.98 (s, 3H).

(2) Synthesis of Intermediate F

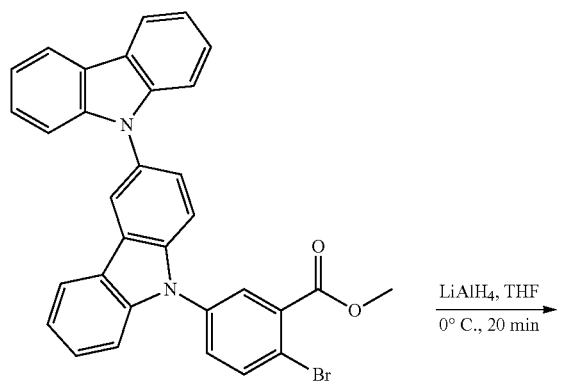

LiAlH$_4$, THF
0° C., 20 min

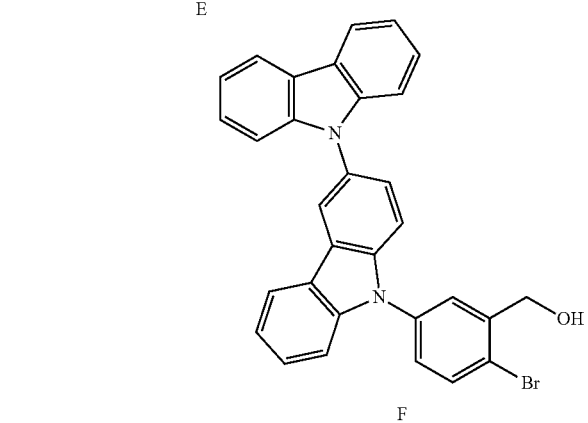

F

The intermediate E (2.0 g, 0.004 mol) was used in the same manner as the synthesis of the intermediate C to finally give a white solid Intermediate F (1.6 g, yield: 84%).

1H NMR (500 MHz, CDCl3): δ (ppm) 8.29-8.26 (m, 1H), 8.18 (d, J=7.6 Hz, 2H), 8.10 (d, J=7.6 Hz, 1H), 7.84-7.79 (m, 2H), 7.59-7.52 (m, 2H), 7.50-7.37 (m, 7H), 7.34-7.27 (m, 3H), 4.88 (d, J=6.1 Hz, 2H), 2.12 (t, J=6.1 Hz, 1H).

(3) Synthesis of Intermediate G

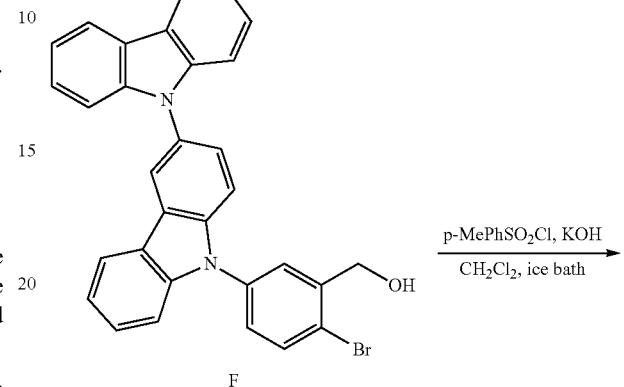

F p-MePhSO$_2$Cl, KOH
CH$_2$Cl$_2$, ice bath

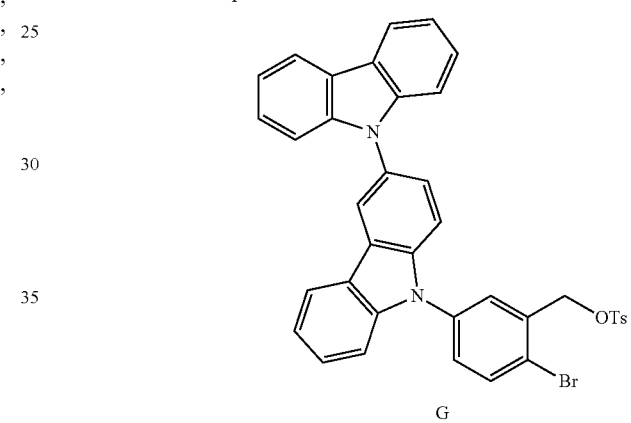

G

The intermediate F (2.2 g, 0.004 mol) was used in the same manner as the synthesis of intermediate D to finally give a white solid Intermediate G (2.5 g, yield: 88%).

$^1$H NMR (500 MHz, CDCl$_3$): δ (ppm) 8.28 (d, J=1.5 Hz, 1H), 8.19 (d, J=7.9 Hz, 2H), 8.11 (d, J=7.6 Hz, 1H), 7.87-7.84 (m, 2H), 7.82 (d, J=8.2 Hz, 1H), 7.68 (d, J=2.4 Hz, 1H), 7.58-7.54 (m, 1H), 7.53-7.29 (m, 13H).

(4) Synthesis of Compound 1-2

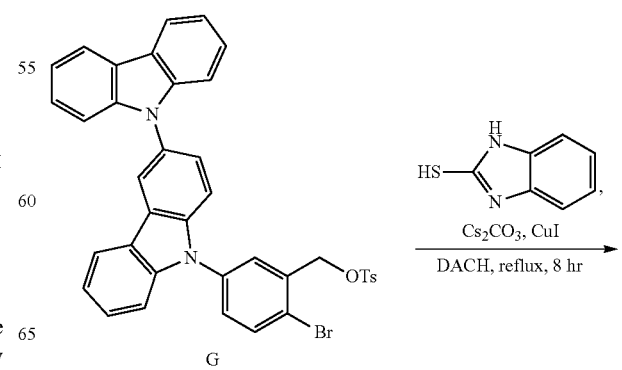

G

Cs$_2$CO$_3$, CuI
DACH, reflux, 8 hr

103

-continued

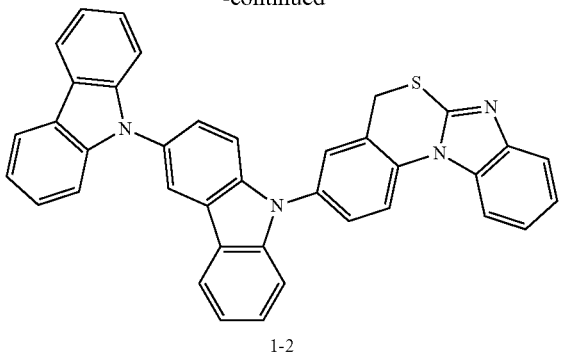

1-2

1H-benzop[d]imidazole-2-thiol (0.5 g, 0.003 mol) and the intermediate G (2.23 g, 0.003 mol) were reacted in the same manner as the synthesis of the compound 1-1 to finally give a white solid Compound 1-2 (1.6 g, yield: 85%).

$^1$H NMR (500 MHz, CDCl$_3$): δ (ppm) 8.30 (d, J=1.8 Hz, 1H), 8.20-8.16 (m, 2H), 8.15-8.10 (m, 2H), 7.93-7.88 (m, 1H), 7.83-7.78 (m, 1H), 7.76 (dd, J=8.5, 2.4 Hz, 1H), 7.69 (d, J=2.1 Hz, 1H), 7.62 (d, J=8.5 Hz, 1H), 7.57 (dd, J=8.7, 2.0 Hz, 1H), 7.53-7.47 (m, 2H), 7.43-7.37 (m, 6H), 7.36-7.33 (m, 1H), 7.32-7.26 (m, 2H), 4.14 (s, 2H).

Synthesis Example 3: Synthesis of Compound 2-5

(1) Synthesis of Intermediate I

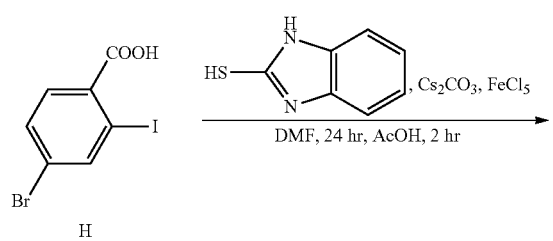

Compound H (10.0 g, 0.031 mol), 1H-benzo[d]imidazole-2-thiol (4.6 g, 0.031 mol), FeCl$_3$ (0.5 g, 0.003 mol) and Cs2CO$_3$ (20 g, 0.061 mol) dissolved in DMF (60 mL) under nitrogen atmosphere were placed into a reactor. After the solution was stirred at 160° C. for 24 hours, AcOH (10 mL) was added drop wise into the solution, and then the solution was stirred at the same temperature for 2 hours. The reactor was cooled down to a room temperature, and the solution was extracted with methylene chloride to remove the solvents. The obtained crude product was purified with a column chromatography to give a white solid Intermediate I (6.0 g, yield: 59%).

$^1$H NMR (500 MHz, CDCl$_3$): δ (ppm) 8.61-8.59 (d, J=8.9 Hz, 1H), 8.48-8.47 (d, J=8.6 Hz, 1H), 7.78-7.77 (d, J=7.4 Hz, 1H), 7.75-7.74 (d, J=1.8 Hz, 1H), 7.68-8.65 (dd, J=8.6, 1.8 Hz, 1H), 7.52-7.44 (m, 2H).

(2) Synthesis of Intermediate J

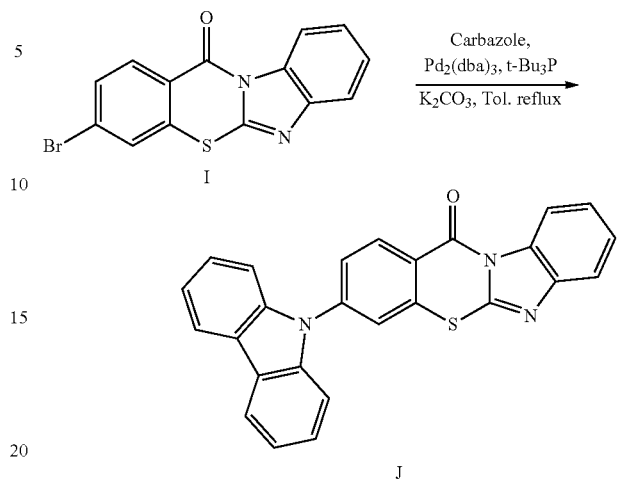

The intermediate I (0.6 g, 0.0018 mol), carbazole (0.36 g, 0.0022 mol) and K$_2$CO$_3$ dissolved in toluene (30 mL) were placed into a reactor, and then the solution was stirred for 30 minutes under nitrogen atmosphere. Tris(dibenzylideneacetone)dipalladium(0) (Pd$_2$(dba)$_3$, 7.2 mg, 2 mol %) and tri-tert-butylphosphine (4.4 mg. 4 mol %) were added into the reactor, and then the solution was stirred at 110° C. for 24 hours. After the temperature was cooled down to a room temperature, the reaction solvent was removed, and then the obtained crude product was purified with a column chromatography to give a white solid Intermediate J (0.26 g, yield: 35%).

$^1$H NMR (500 MHz, CDCl3): δ (ppm) 8.89-8.87 (d, J=8.6 Hz, 1H), 8.69-8.68 (d, J=7.0 Hz, 1H), 8.17-8.16 (d, J=8.0 Hz, 2H), 7.86-7.81 (m, 3H), 7.58-7.57 (d, J=8.3 Hz, 2H), 7.56-7.52 (td, J=7.7, 1.4 Hz, 1H), 7.52-7.47 (m, 3H), 7.39-7.36 (t, J=7.3 Hz, 2H).

(3) Synthesis of Compound 2-5

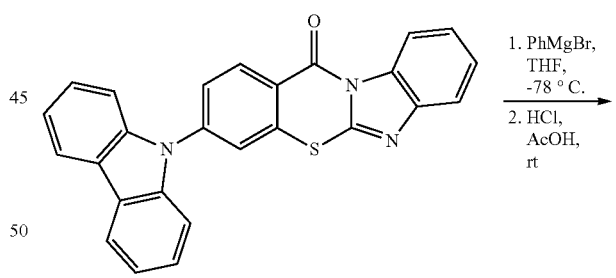

J

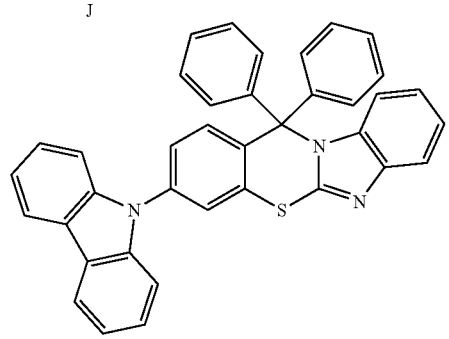

2-5

The intermediate J (0.39 g, 0.93 mmol) dissolved in THF (60 mL) under nitrogen atmosphere was placed into a reactor, and then the solution was cooled down to −78° C. 1.0 M phenylmagnesium bromide (PhMgBr, 3.75 mL) was added slowly drop wise to the reaction solution. After stirring at a room temperature for 6 hours, the solution was extracted with diethyl ether to remove the solvent. The reaction mixture was dissolved in CH₃COOH (10 mL) and then HCl (2 mL) was added slowly drop wise to the mixture. The solution was stirred at a room temperature for 1 hour, was neutralized with NaHCO₃ aqueous solution, and then extracted with CH₂Cl₂. After removing the solvent, the obtained crude product was purified with a column chromatography to give a white solid Compound 2-5 (0.2 g, yield: 40%).

$^1$H NMR (500 MHz, CDCl$_3$): δ (ppm) 8.15-8.13 (d, J=7.9 Hz, 2H), 7.74-7.72 (d, J=7.6 Hz, 1H), 7.70-7.69 (d, J=2.2 Hz, 1H), 7.49-7.42 (m, 7H), 7.40-7.37 (t, J=7.6 Hz, 4H), 7.33-7.30 (t, J=7.3 Hz, 2H), 7.21-7.18 (m, 2H), 7.00-6.99 (d, J=7.7 Hz, 4H), 6.85-6.82 (t, J=8.0 Hz, 1H), 5.53-5.51 (d, J=8.3 Hz, 1H).

Synthesis Example 4: Synthesis of Compound 2-17

(1) Synthesis of Intermediate K

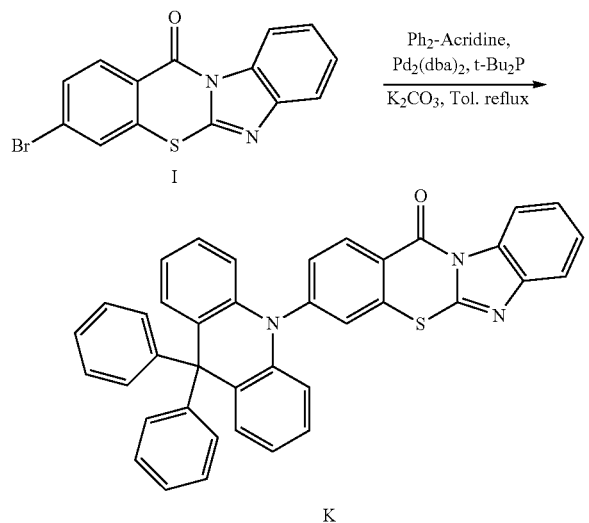

K

The intermediate I (0.6 g, 0.0018 mol) and 9,9-diphenylacridine (0.73 g, 0.0022 mol) were reacted in the same manner as the synthesis of the intermediate J to finally give a white solid Intermediate K (0.44 g, yield: 42%).

(2) Synthesis of Compound 2-17

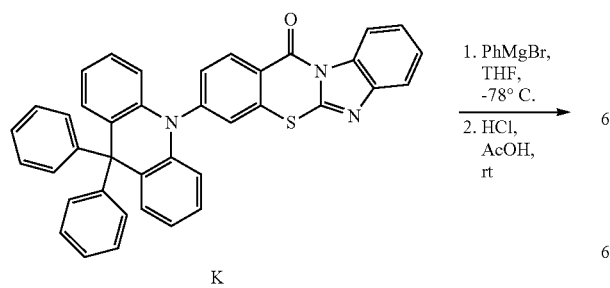

K

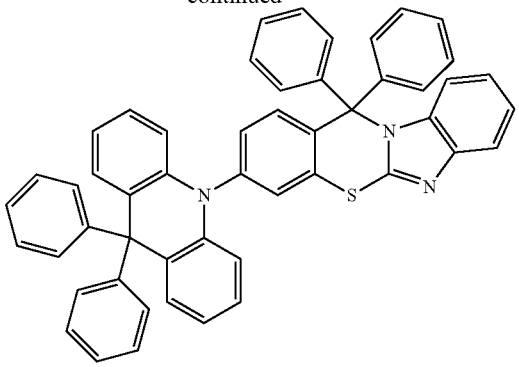

2-17

The intermediate K (0.44 g, 0.75 mol) and 1.0M PhMgBr (3.0 mL) were reacted in the same manner as the synthesis of compound 2-5 to finally give a white solid Compound 2-17 (0.26 g, yield: 48%).

Experimental Example 1: Measurement of Energy Level

HOMO energy level, LUMO energy level, energy level bandgap ($E_g$) between the HOMO and LUMO energy levels, excited singlet energy level ($S_1$), excited triple energy level ($T_1$) and photoluminescence peak (PL peak) for the Compounds synthesized in Synthesis Examples were evaluated. A simulation evaluation result is illustrated in Table 1 below, and experiment result in a coated thin film as a solution state is illustrated in Table 2 below.

TABLE 1

| Energy level Simulation Test (DFT calculation) | | | | | |
|---|---|---|---|---|---|
| Compound | HOMO (eV) | LUMO (eV) | Eg (eV) | $S_1$ (eV) | $T_1$ (eV) |
| 1-1 | −5.53 | −1.16 | 4.37 | 3.81 | 3.18 |
| 1-2 | −5.23 | −1.30 | 3.93 | 3.55 | 3.15 |
| 2-5 | −5.49 | −0.94 | 3.55 | 3.93 | 3.18 |
| 2-17 | −5.17 | −0.94 | 4.23 | 3.50 | 3.33 |

TABLE 2

| Energy Levels of Organic Compound | | | | | |
|---|---|---|---|---|---|
| Compound | PL(sol)$^a$ | $E_g^{opt\ b}$ | HOMO$^c$ (eV) | LUMO$^d$ (eV) | $T_1$ (eV) |
| 1-1 | 355 | 3.4 | −5.7 | −2.3 | 3.0 |
| 1-2 | 376 | 3.3 | −5.6 | −2.3 | 3.0 |
| 2-5 | 347 | 3.5 | −5.7 | −2.2 | 3.0 |
| 2-17 | 388 | 3.2 | −5.6 | −2.4 | 2.9 |

$^a$2-Me THF;
$^b$Toluene;
$^c$Sample: 1 mM in DMF solution;
$^d$LUMO(eV) = HOMO(eV) + $E_g^{opt}$ (eV)

As indicated in Tables 1 and 2, all the organic compounds synthesized in Synthesis Examples have proper HOMO energy levels, LUMO energy levels, energy bandgaps and excited singlet and triplet energies for an emissive layer. Particularly, the organic compounds have very high excited triplet energy levels and were proper for the host in EML and as materials for the ETL and HBL considering the energy bandgap between the $S_1$ and $T_1$. Also, all the compounds emitted light in the blue wavelength band.

Example 1 (Ex. 1): Fabrication of OLED

An OLED in which the Compound 1-1 is applied into a host of an EML was fabricated. An ITO attached glass substrate was washed with UV ozone and loaded into the vapor system, and then was transferred to a vacuum deposition chamber in order to deposit other layers on the substrate. An organic layer was deposited by evaporation by a heated boat under $10^{-7}$ torr at a deposition rate of 1 Å in the following order:

An anode (ITO, 50 nm); A HIL (HAT-CN, 7 nm); a HTL (TAPC, 50 nm); an EBL (DCDPA, 10 nm); an EML (Compound 1-1(host): blue delayed fluorescent material TczTrz (dopant)=70:30 by weight, 30 nm); a HBL (TSPO1, 5 nm); an ETL (TPBi, 25 nm); an EIL (LiF, 1.5 nm); and a cathode (Al, 100 nm).

And then, cappling layer (CPL) was deposited over the cathode and the device was encapsualted by glass. After deposition of emissve layer and the cathode, the OLED was transferred from the depostion chamber to a dry box for film formation, followed by encapsulation using UV-curable epoxy resin and moisture getter.

Examples 2-3 (Ex. 2-3): Fabrication of OLED

An OLED was fabricated using the same materials as Example 1, except that Compound 1-2 (Ex. 2) or Compound 2-5 (Ex. 3) was applied into the EML as the host instead of the Compound 1-1.

Comparative Example 1(Ref. 1): Fabrication of OLED

OLED was fabricated using the same materials as Example 1, except that mCBP (Ref. 1) was applied into the EML as the host instead of the Compound 1-1.

Experimental Example 2: Measurement of Luminous Properties of OLED

Each of the OLED fabricated by Ex. 1-3 and Ref. 1 having 9 mm² of luminous area was connected to an external power source and then luminous properties for all the diodes were evaluated using a constant current source (KEITHLEY) and a photometer PR650 at a room temperature. In particular, driving voltage (V), current efficiency (cd/A), power efficiency (1 m/W), external quantum efficiency (EQE, %), maximum EQE ($EQE_{max}$) and CIE color coordinates at a current density of 10 mA/cm² were measured. The results thereof are shown in the following Table 3.

TABLE 3

Luminous Properties of OLED

| Sample | Host | V | cd/A | lm/W | EQE | $EQE_{max}$ | CIE(x, y) |
|---|---|---|---|---|---|---|---|
| Ref. 1 | mCBP | 4.0 | 25.8 | 20.4 | 14.7 | 22.8 | (0.162, 0.289) |
| Ex. 1 | 1-1 | 4.1 | 27.5 | 21.2 | 15.3 | 23.0 | (0.163, 0.298) |
| Ex. 2 | 1-2 | 4.2 | 27.0 | 19.5 | 15.0 | 23.8 | (0.164, 0.299) |
| Ex. 3 | 2-5 | 3.7 | 30.1 | 25.8 | 15.7 | 22.0 | (0.170, 0.333) |

As indicated in Table 3, compared to the OLED in Ref. 1 which uses mCBP as the host, the OLEDs in Ex. 1-3 showed equivalent or a little bit lower driving voltages, but enhanced their current efficiency, power efficiency and EQE up to 16.7%, 26.5% and 6.8%, respectively.

It will be apparent to those skilled in the art that various modifications and variations can be made in the present disclosure without departing from the scope of the disclosure. Thus, it is intended that the present disclosure cover the modifications and variations of the present disclosure provided they come within the scope of the appended claims.

What is claimed is:

1. An organic compound having the following structure of Chemical Formula 1:

[Chemical Formula 1]

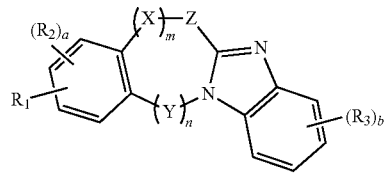

wherein $R_1$ is an unsubstituted or substituted fused hetero aromatic group having three to six aromatic or hetero aromatic rings and having one to three nitrogen atoms, an unsubstituted or substituted $C_6$-$C_{30}$ aromatic amino group or an unsubstituted or substituted $C_4$-$C_{30}$ hetero aromatic amino group; wherein each of $R_2$ and $R_3$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, wherein each of $R_2$ and $R_3$ is identical to or different from each other when each of a and b is independently an integer two or more; each of a and b is independently the number of a substituent, a is an integer of 0 (zero) to three and b is an integer of 0 (zero) to four; each of X and Y is independently $CR_4R_5$, wherein each of $R_4$ and $R_5$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, or $R_4$ and $R_5$ form a $C_6$-$C_{20}$ aromatic ring or a $C_3$-$C_{20}$ hetero aromatic ring; each of m and n is 0(zero) or 1, wherein m+n=1; Z is S or O.

2. The organic compound of claim 1, wherein the fused hetero aromatic group is unsubstituted, substituted with a group selected from a $C_1$-$C_{20}$ alkyl group, a $C_6$-$C_{20}$ aryl group, a $C_3$-$C_{20}$ hetero aryl group and combination thereof, or forms a spiro structure with a fluorene ring or a xanthene ring.

3. The organic compound of claim 1, wherein the fused hetero aromatic group is selected from the group consisting of a carbazolyl moiety, an acridinyl moiety, a dihydro acridinyl moiety, a phenazinyl moiety and a phenoxazinyl moiety.

4. The organic compound of claim 1, wherein the fused hetero aromatic group is unsubstituted or substituted with a group selected from a $C_1$-$C_{10}$ alkyl group, phenyl, carbazolyl and combination thereof, or forms a spiro structure with a xanthene ring, and each of $R_4$ and $R_5$ is unsubstituted or substituted with a group selected from a $C_1$-$C_{10}$ alkyl group, phenyl and combination thereof, or $R_4$ and $R_5$ forms a fluorene ring.

5. The organic compound of claim 1, wherein Z is S.
6. The organic compound of claim 1, wherein the organic compound comprises anyone having the following structure of Chemical Formula 2:
[Chemical Formula 2]
1-1
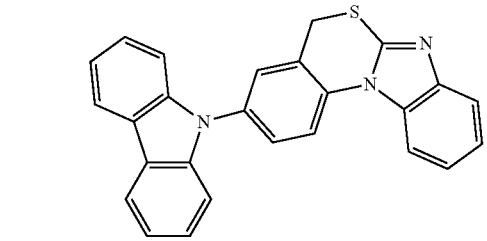
1-2
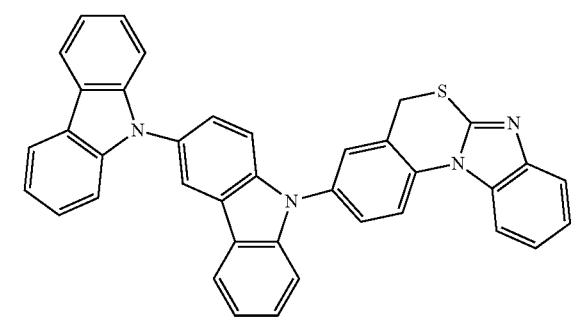
1-3
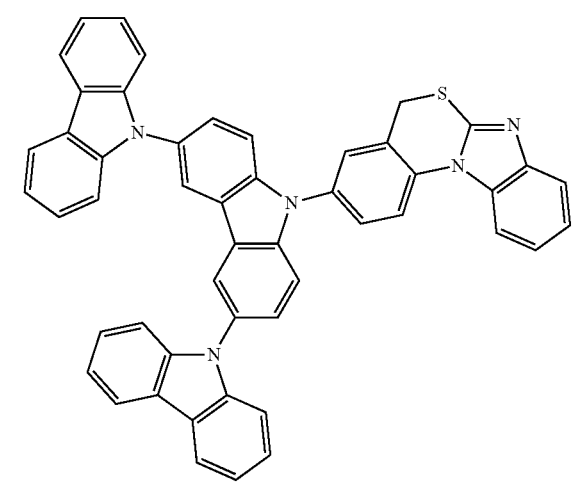
1-4
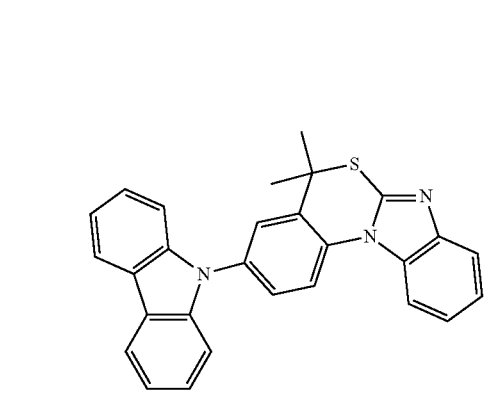
1-5
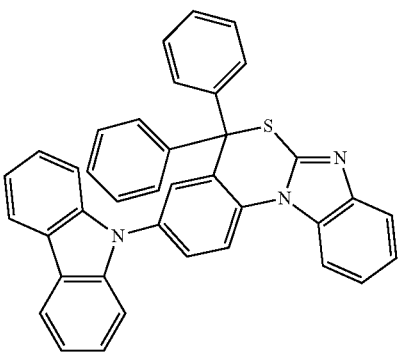
1-6
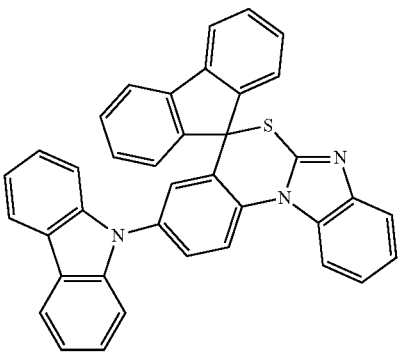
1-7
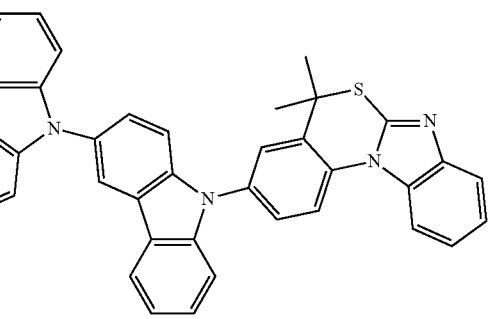
1-8
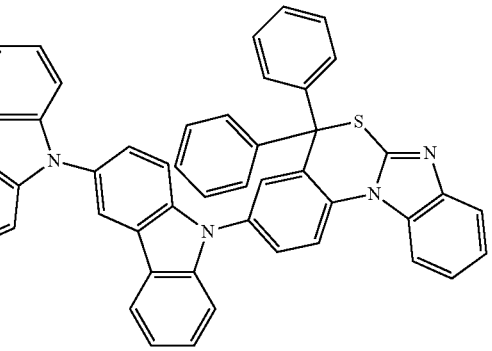

1-9
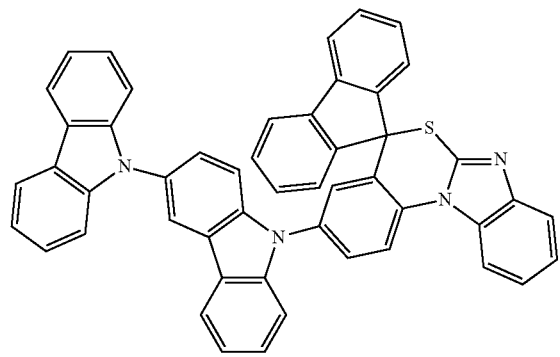
1-10
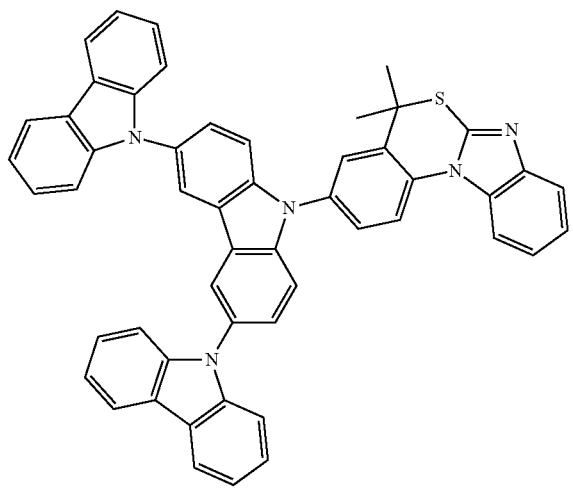
1-11
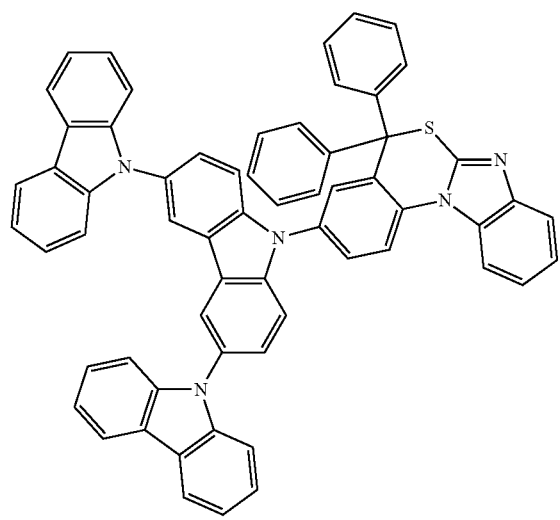
1-12
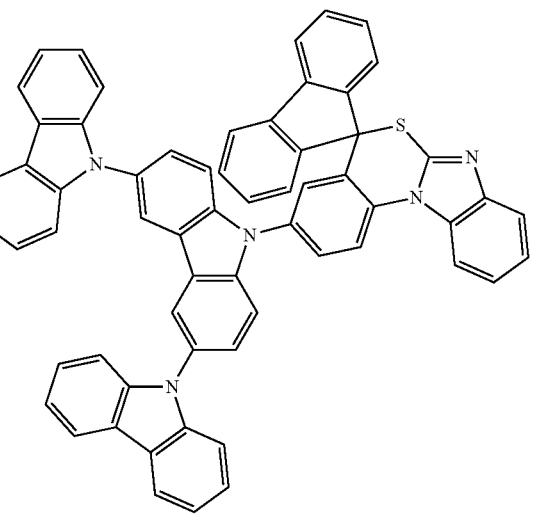
1-13
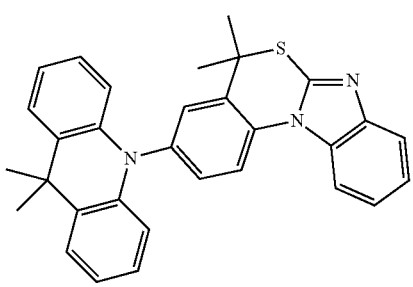
1-14
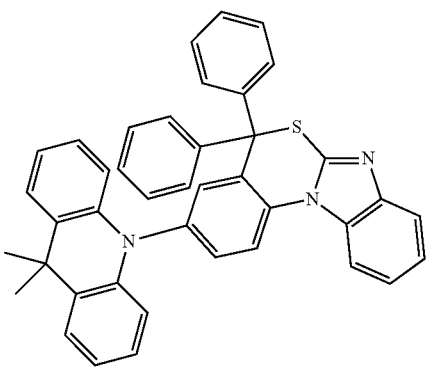
1-15
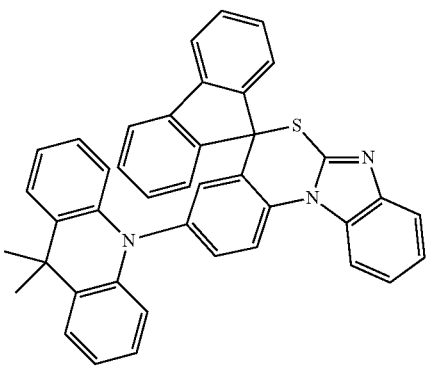

1-16
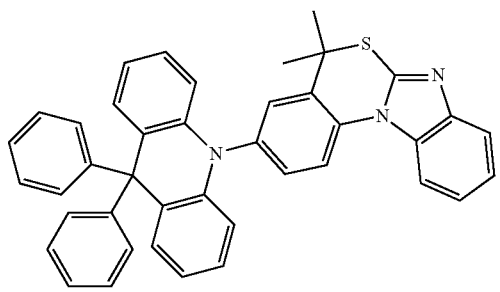
1-17
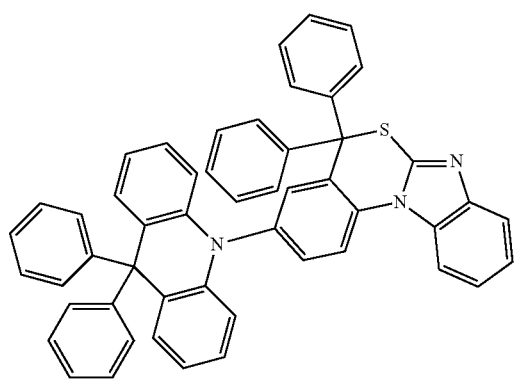
1-18
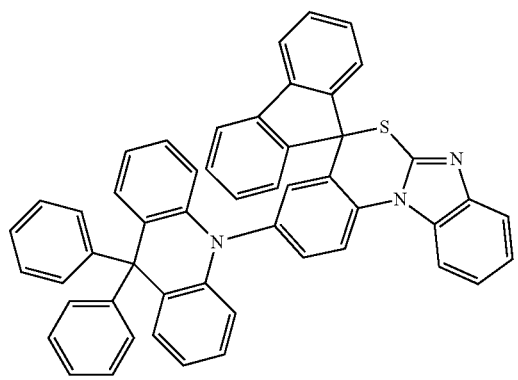
1-19
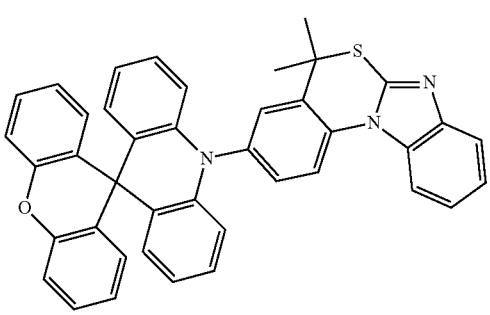
1-20
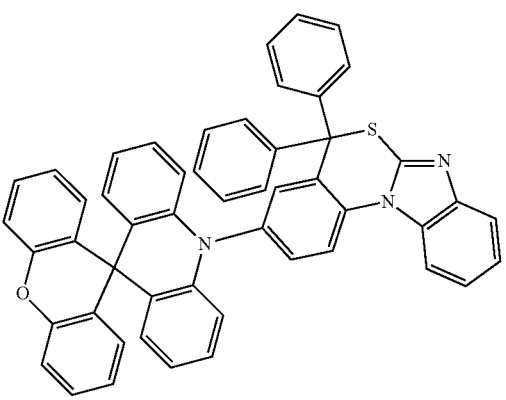
1-21
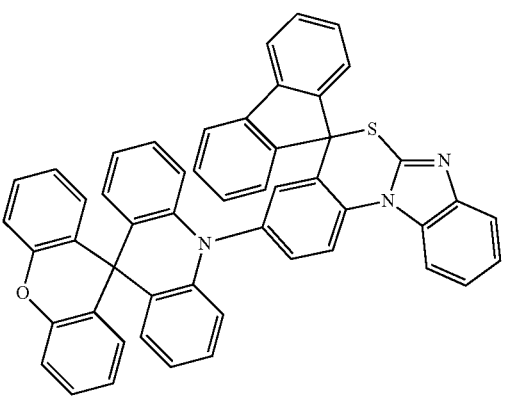
1-22
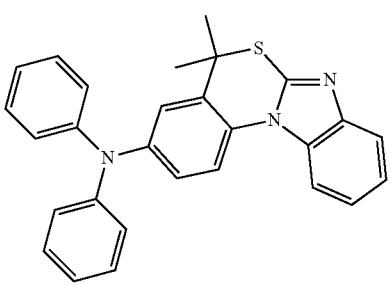
1-23
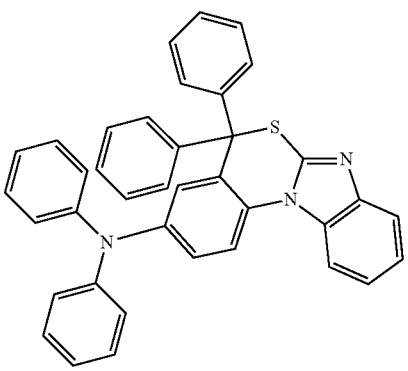

1-24
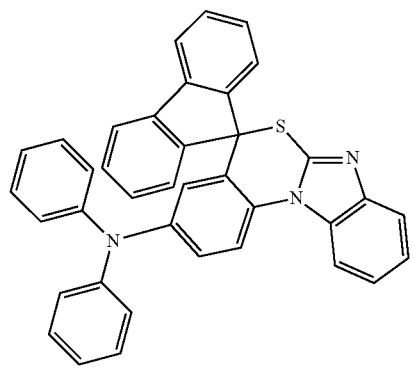
1-25
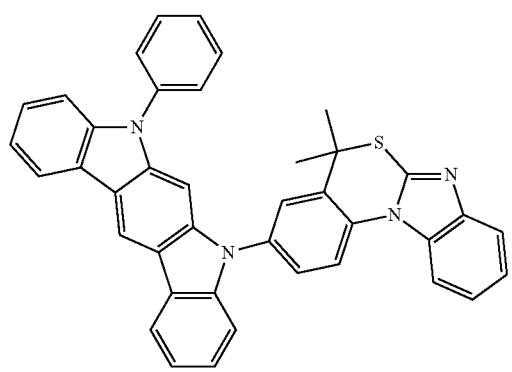
1-26
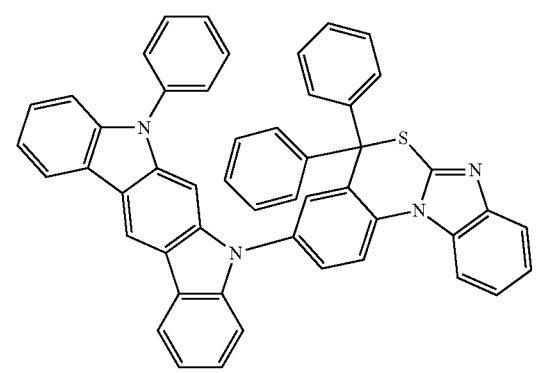
1-27
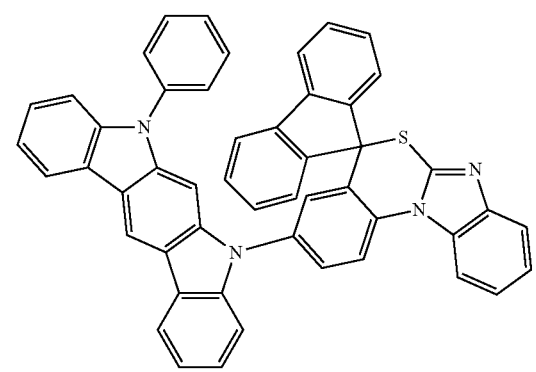
1-28
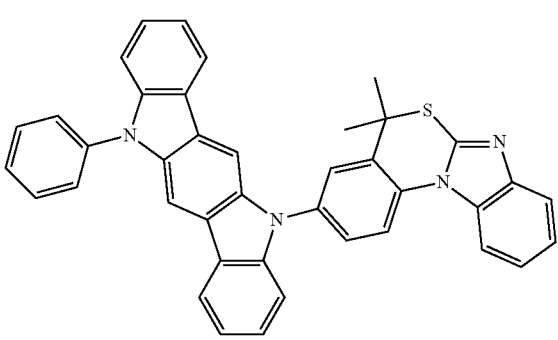
1-29
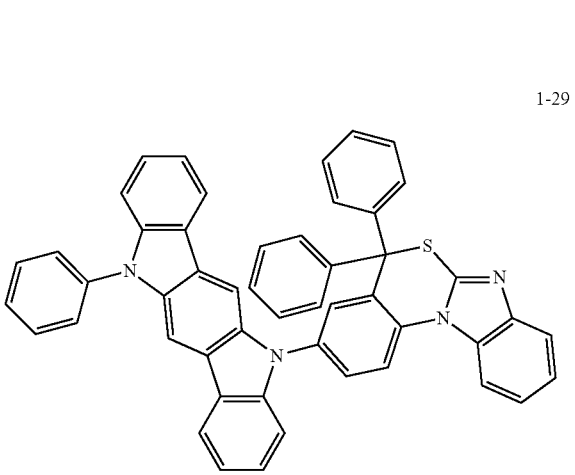
1-30
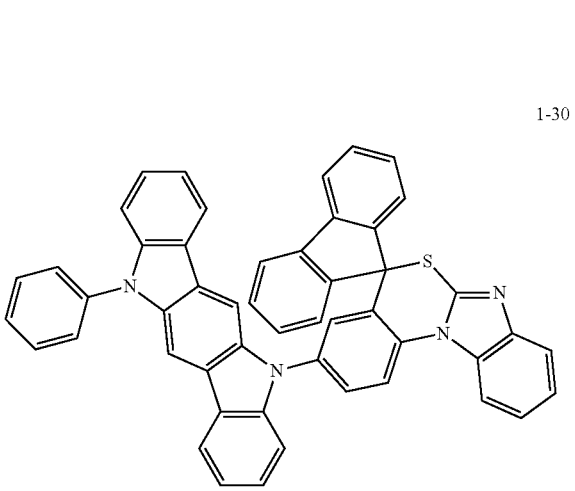
1-31
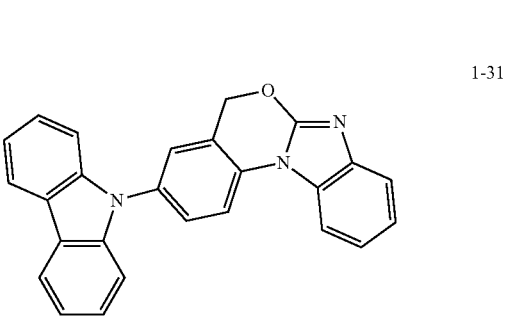

1-32
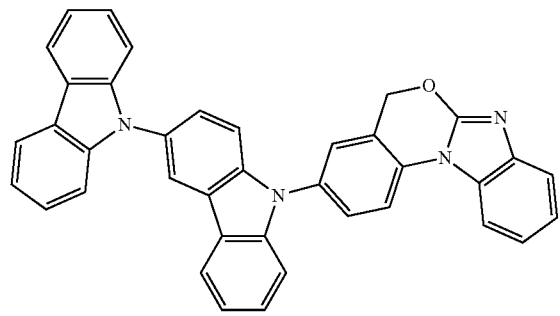
1-33
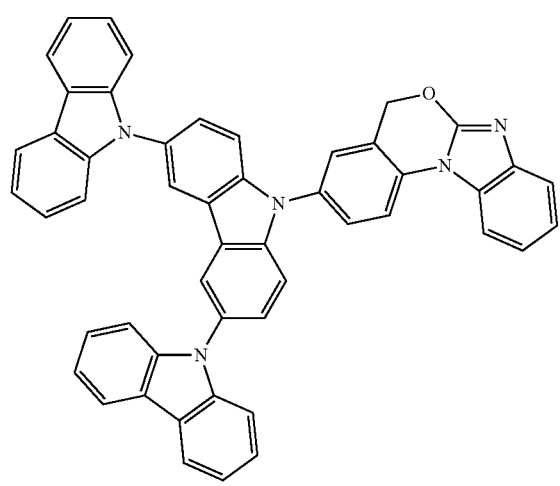
1-34
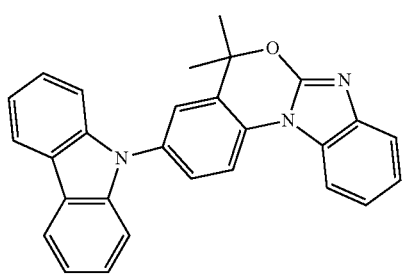
1-35
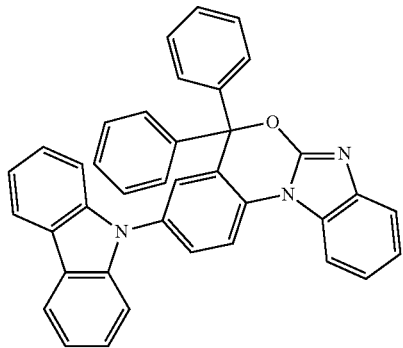
1-36
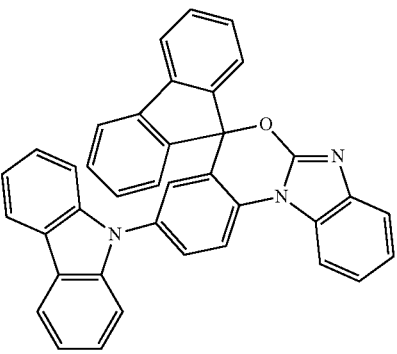
1-37
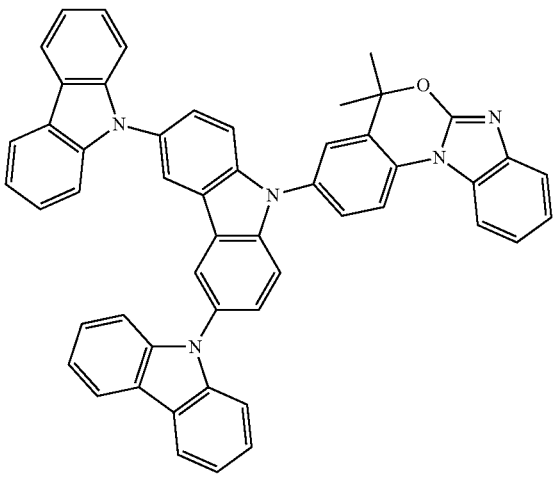
1-38
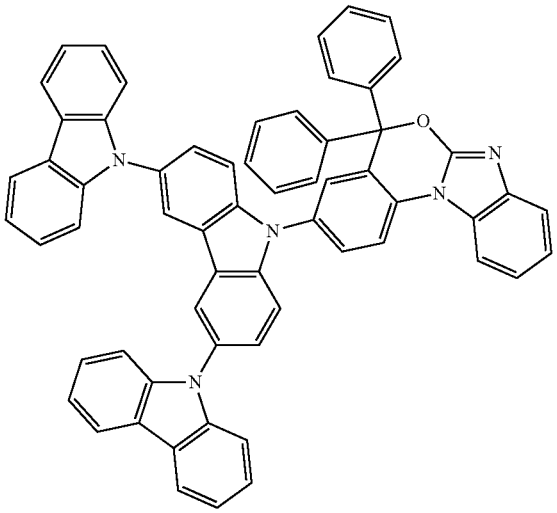

1-39
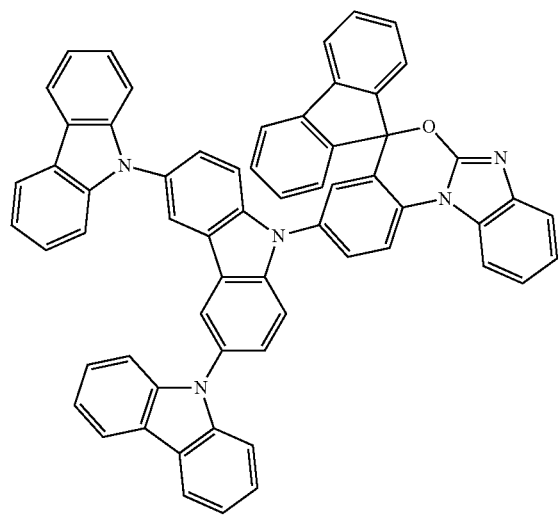
1-40
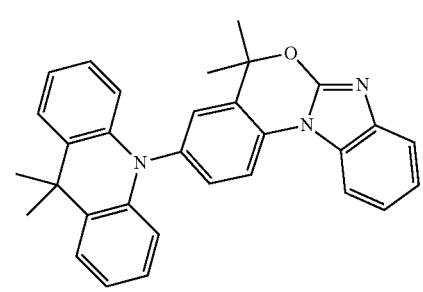
1-41
1-42
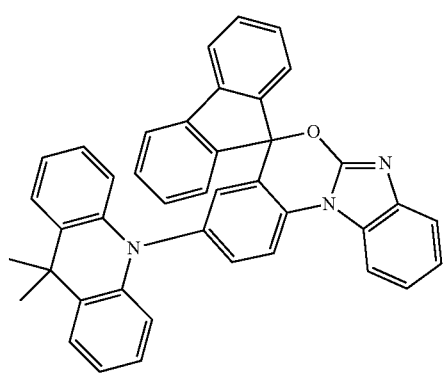
1-43
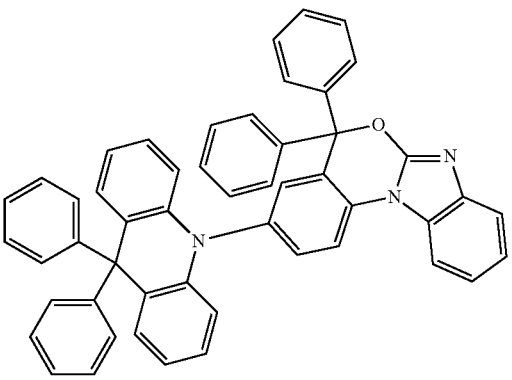
1-44
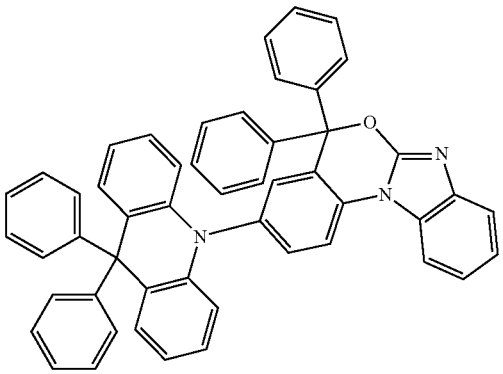
1-45
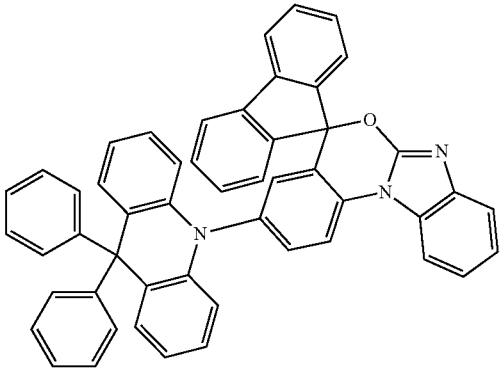
1-46
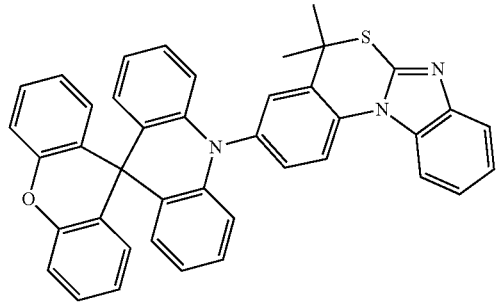

-continued
1-47
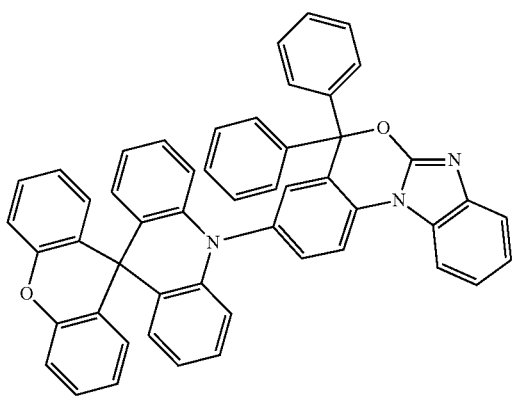
1-48
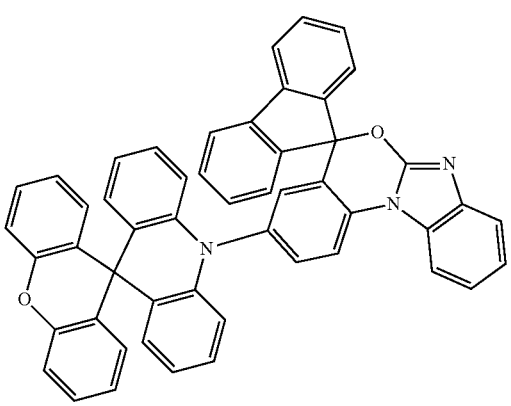
1-49
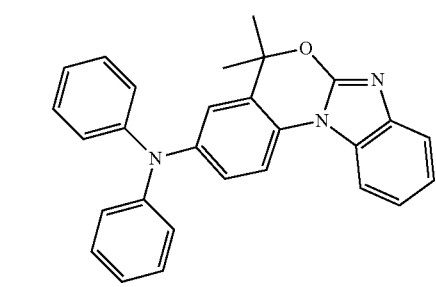
1-50
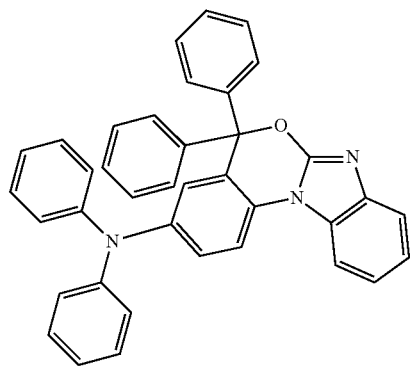
-continued
1-51
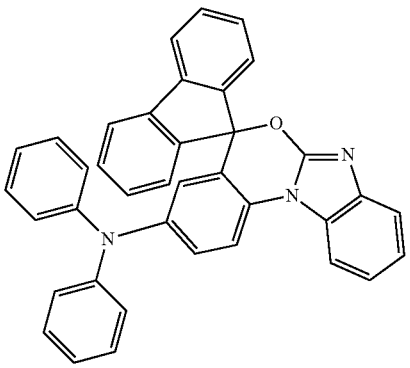
1-52
1-53
1-54
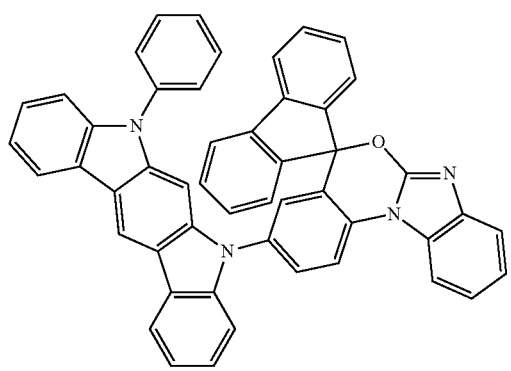

1-55
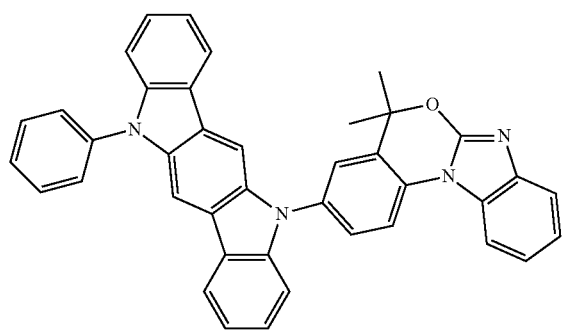
1-56
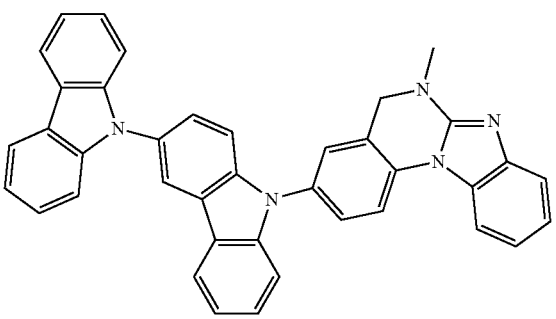
1-57
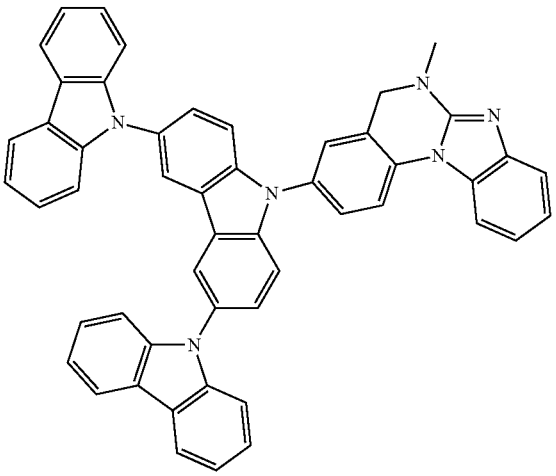
1-58
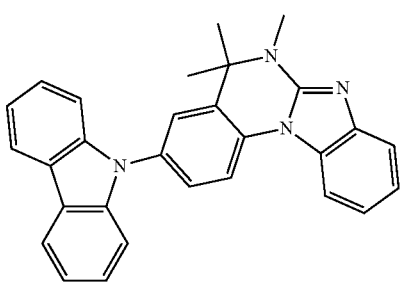
1-59
1-60
1-61
1-62
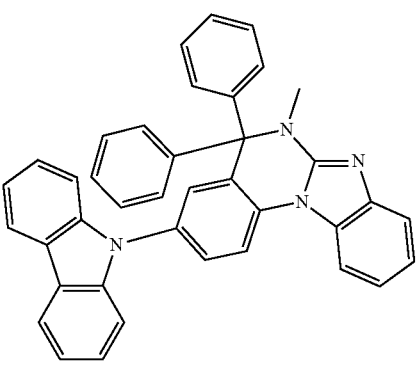

1-63
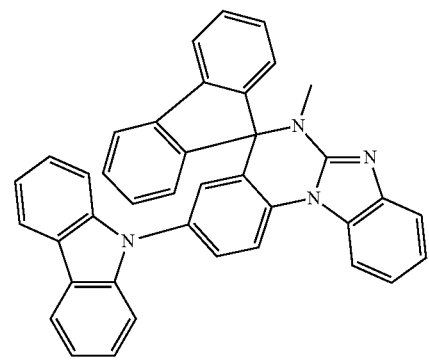
1-64
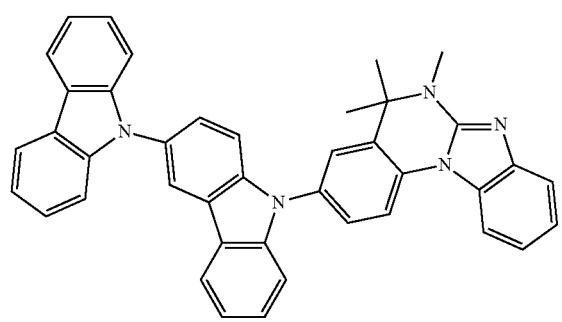
1-65
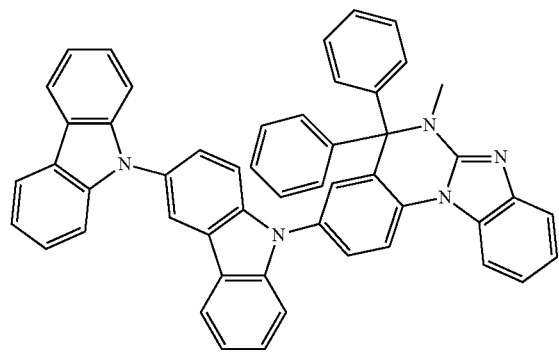
1-66
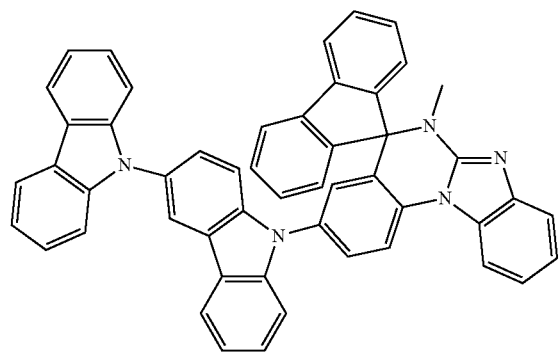
1-67
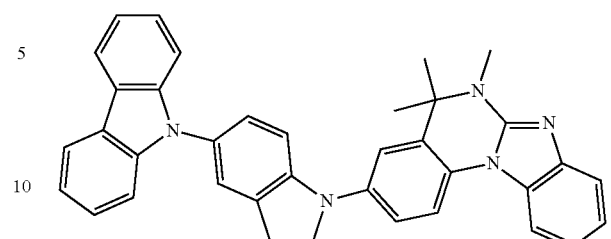
1-68
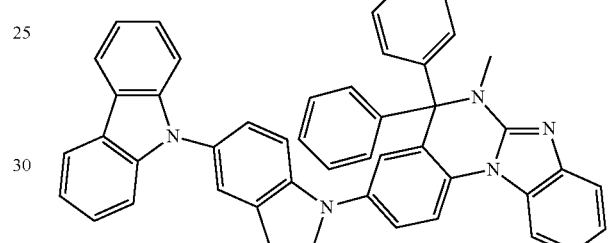
1-69
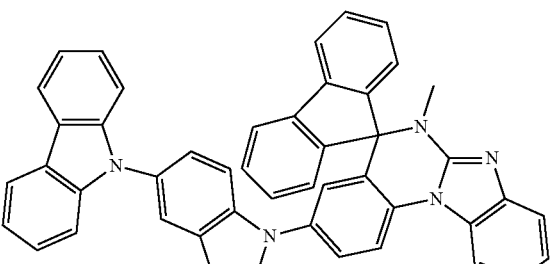

1-70
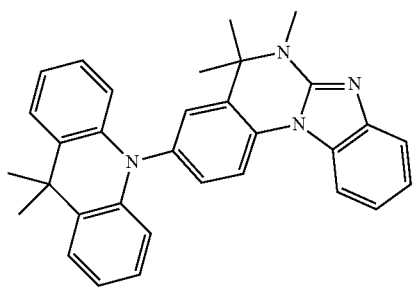
1-71
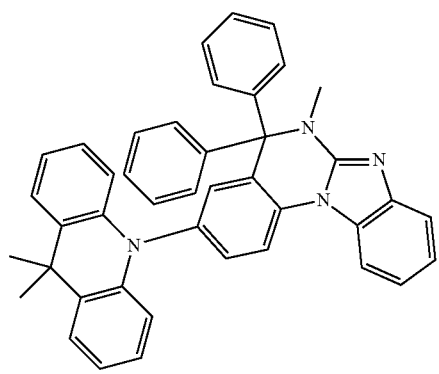
1-72
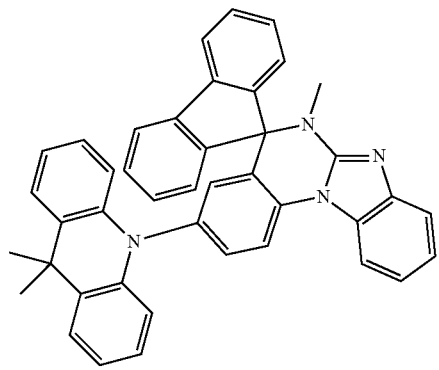
1-73
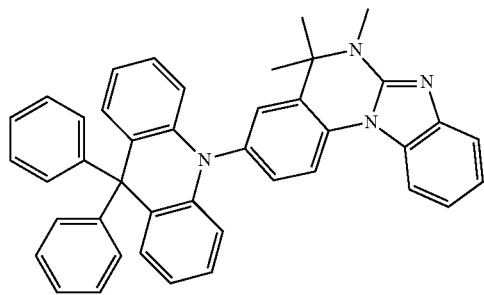
1-74
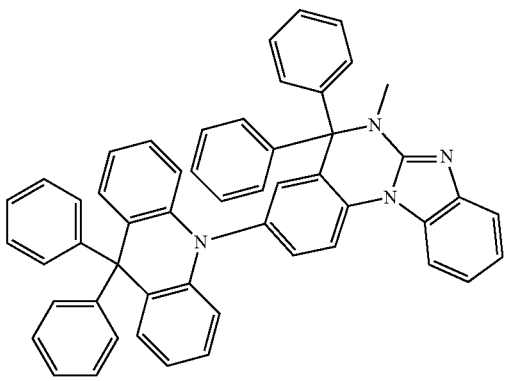
1-75
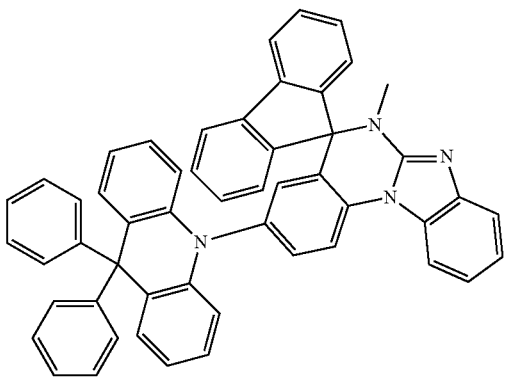
1-76
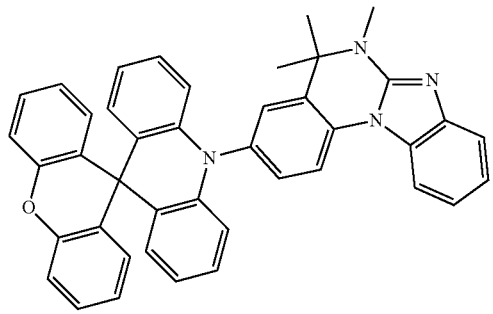
1-77
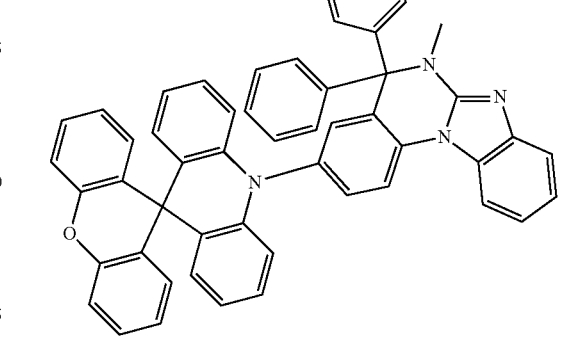

1-78
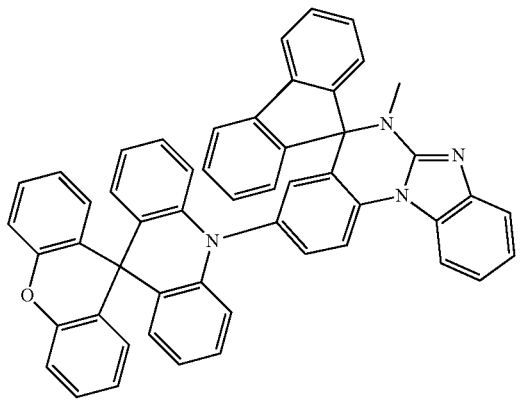
1-79
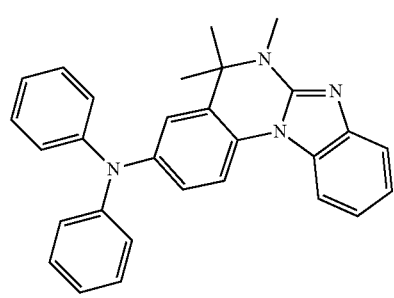
1-80
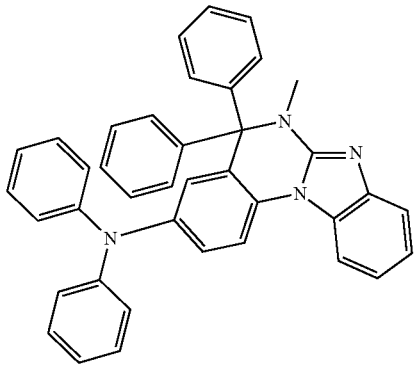
1-81
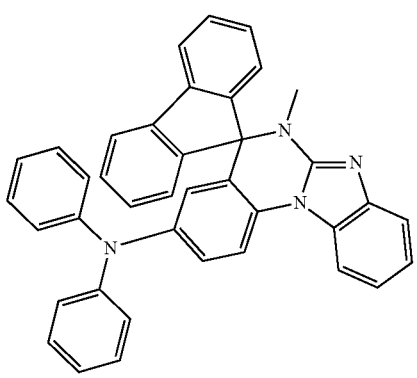
1-82
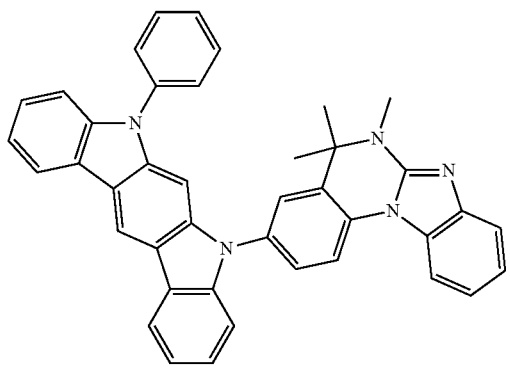
1-83
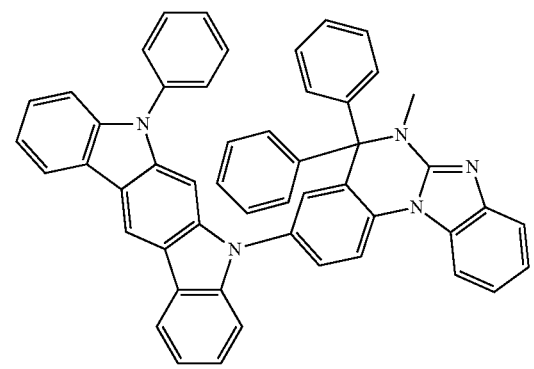
1-84
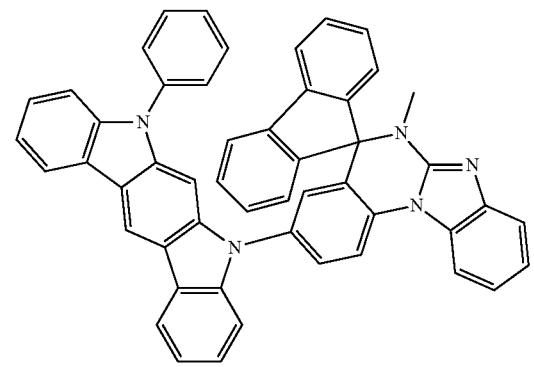
1-85
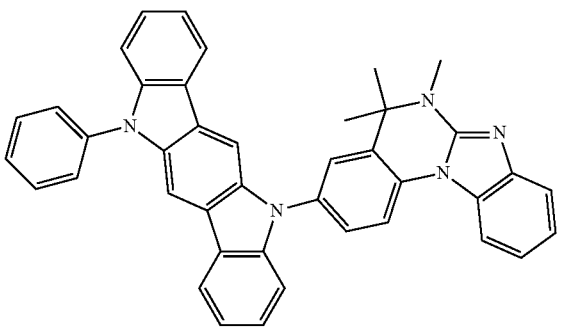

-continued
1-86
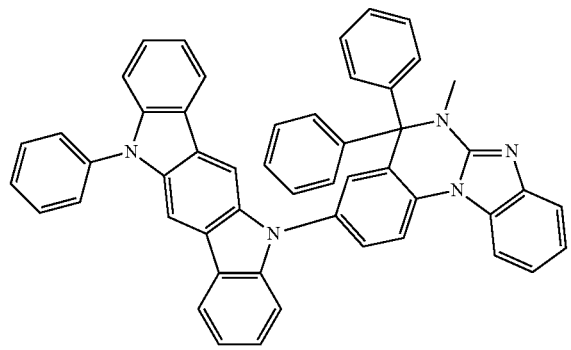
1-87
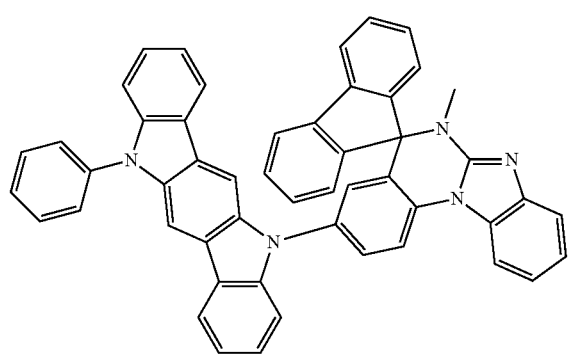
1-88
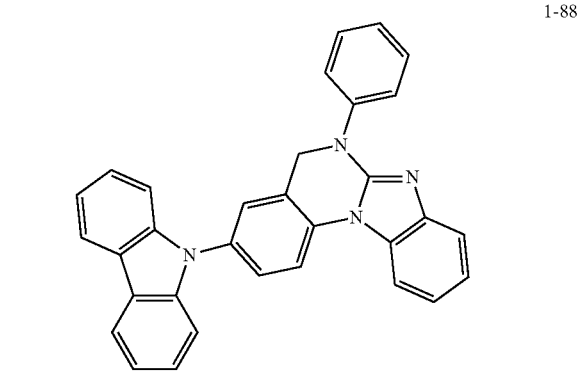
1-89
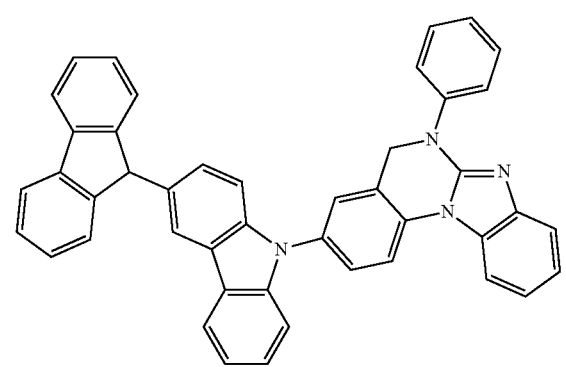
-continued
1-90
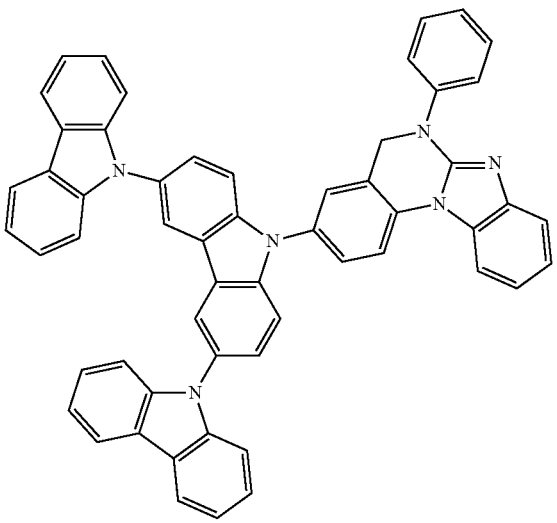
1-91
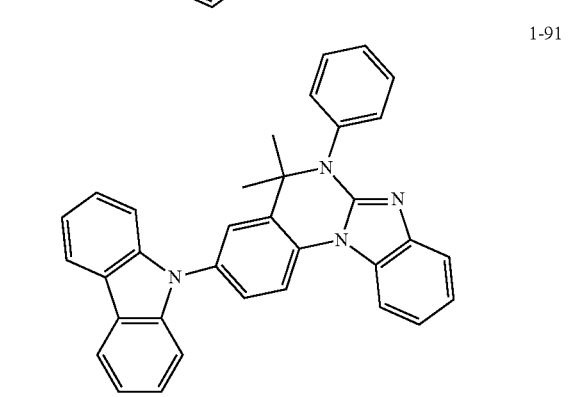
1-92
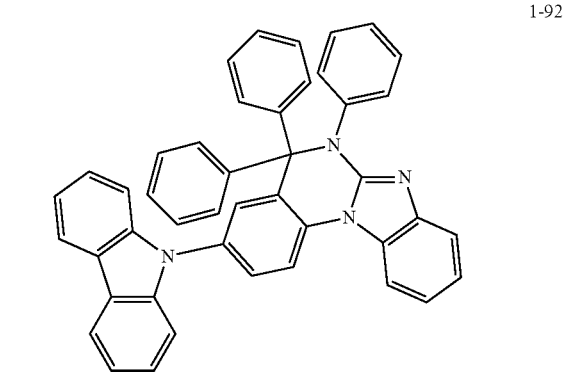
1-93
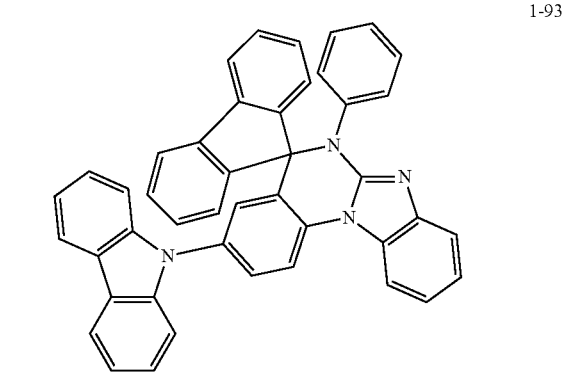

1-94
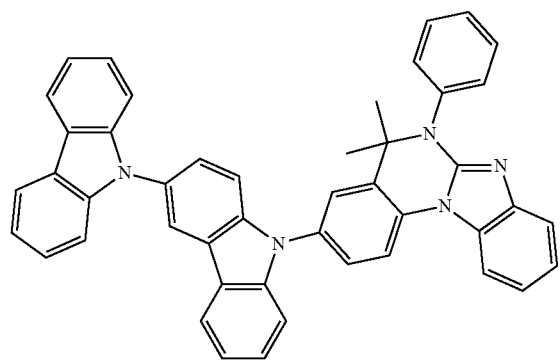
1-97
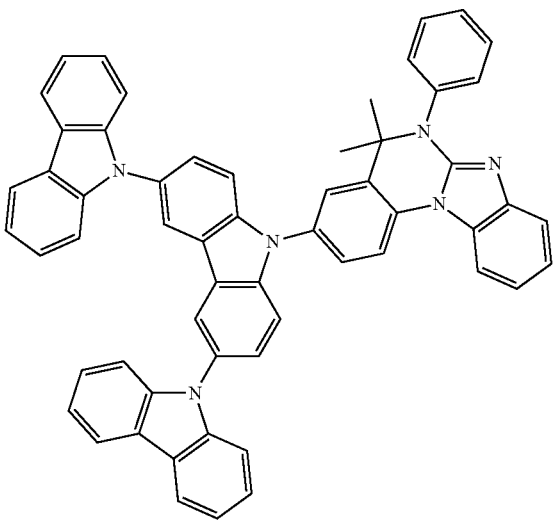
1-95
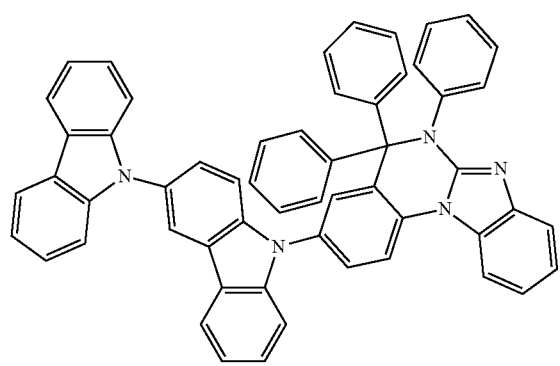
1-98
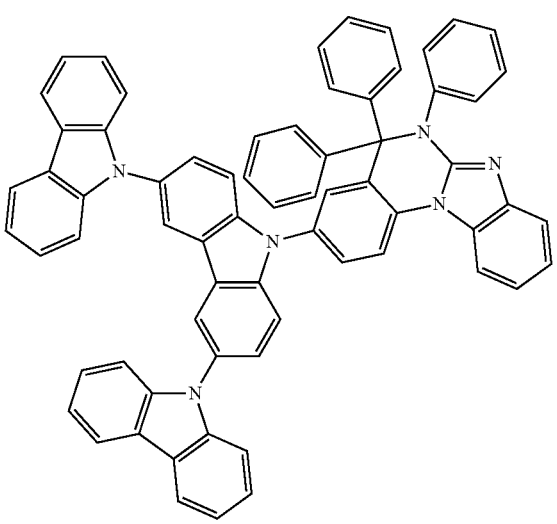
1-96
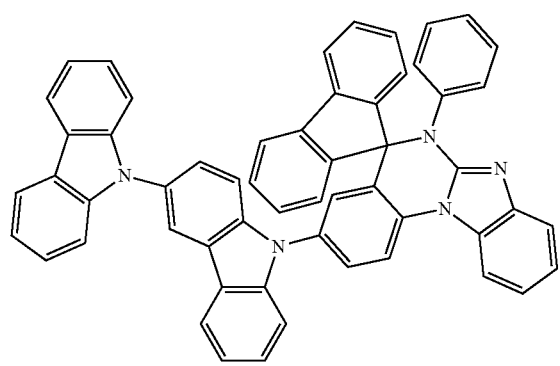
1-99
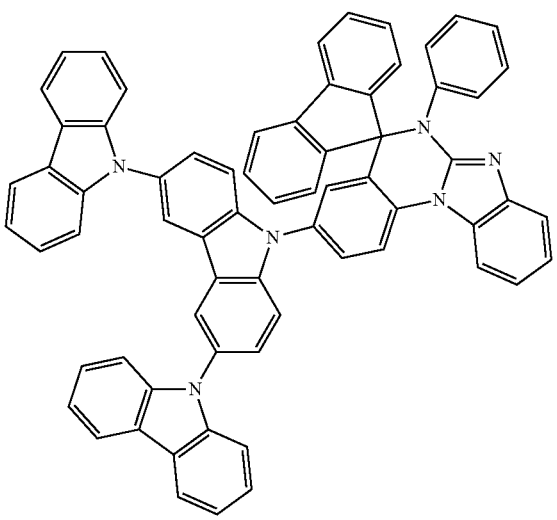

1-100
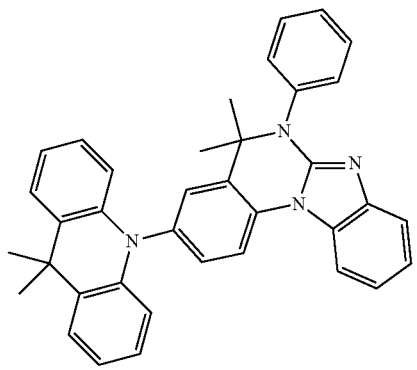
1-101
1-102
1-103
1-104
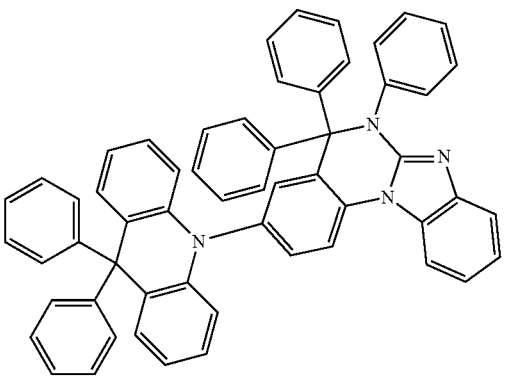
1-105
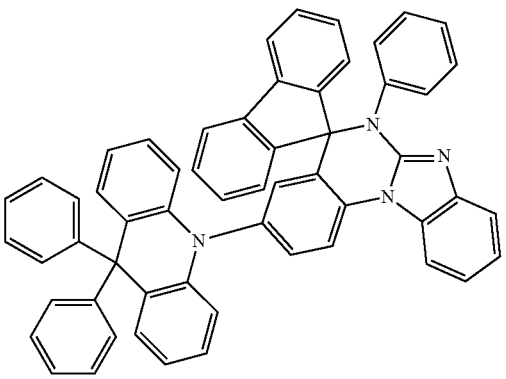
1-106
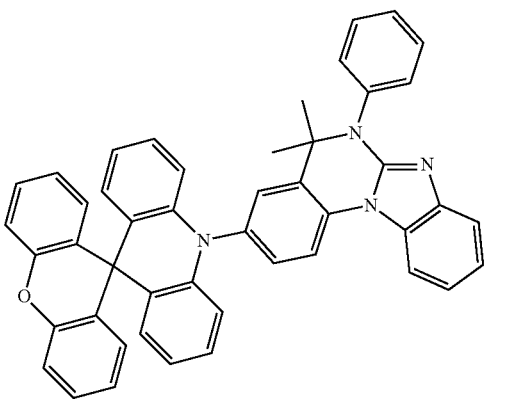
1-107
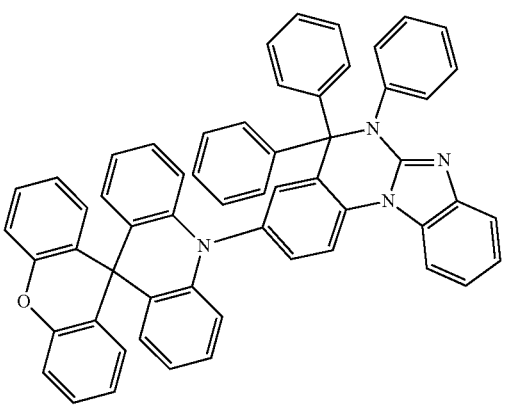

-continued
1-108
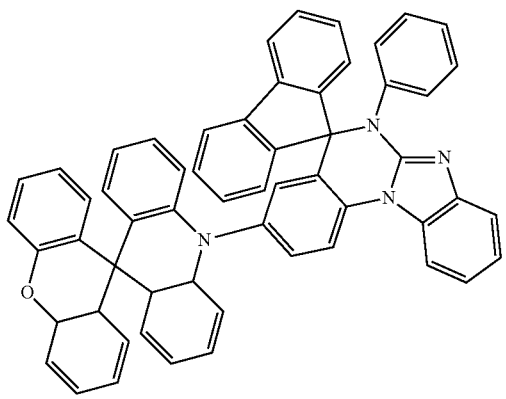
1-112
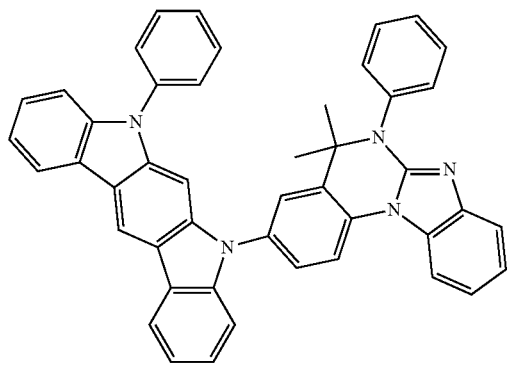
1-109
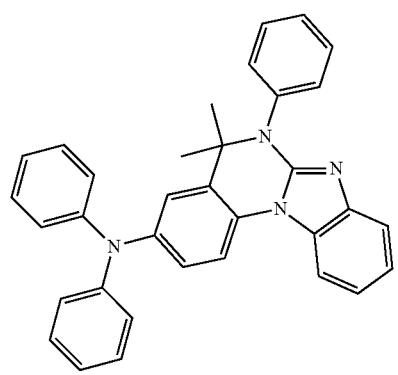
1-113
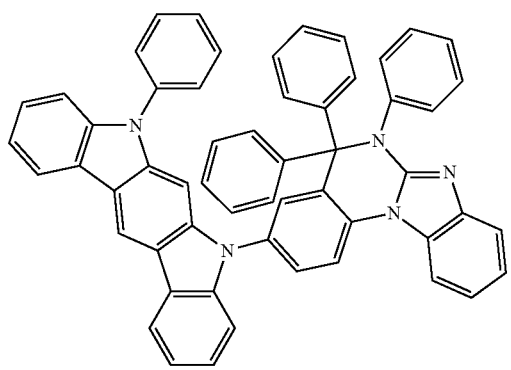
1-110
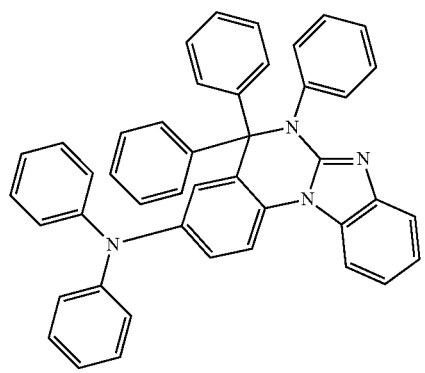
1-114
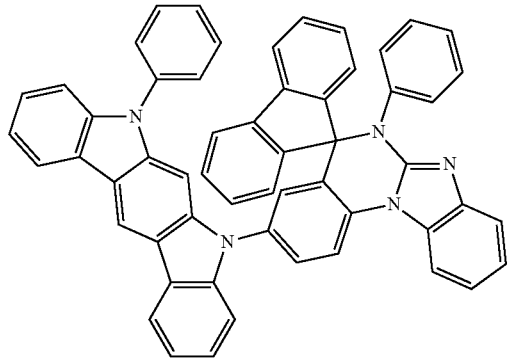
1-111
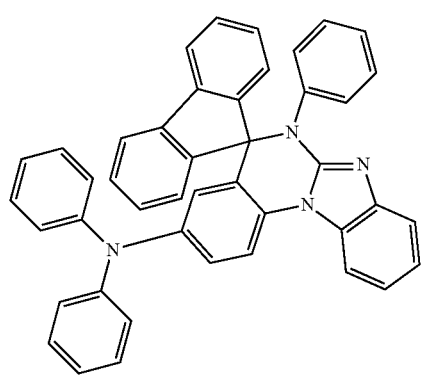
1-115
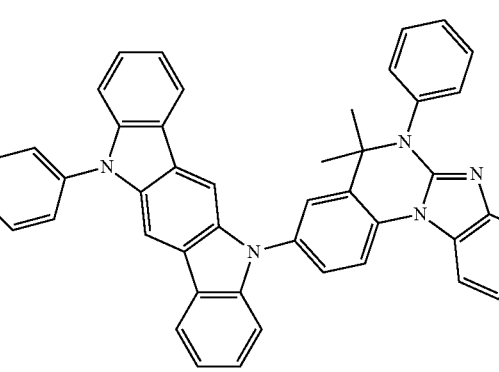

1-116
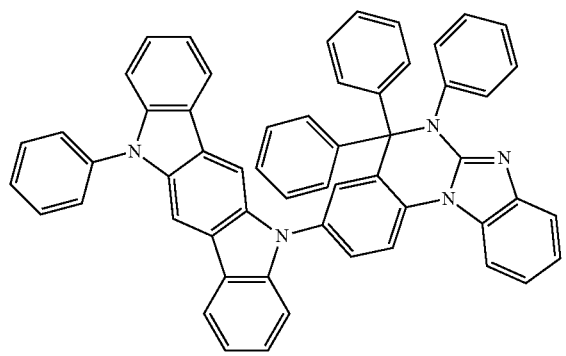
1-117
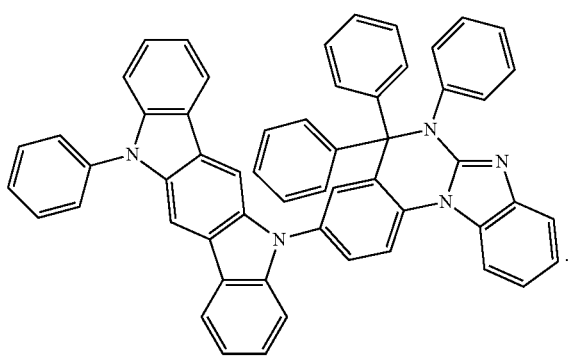
2-3
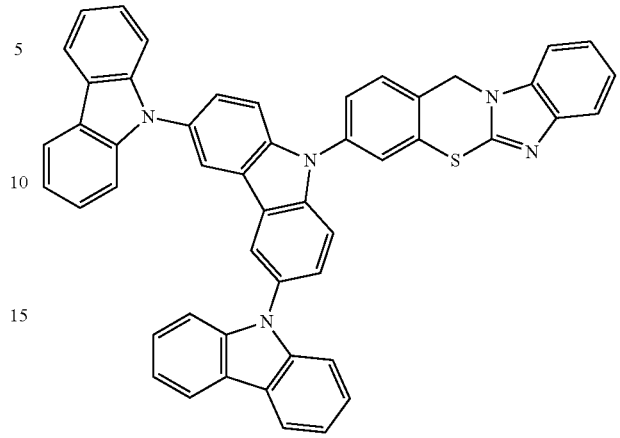
2-4
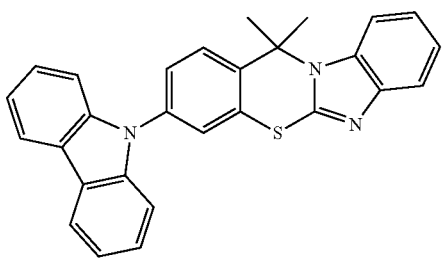
7. The organic compound of claim 1, wherein the organic compound comprises anyone having the following structure of Chemical Formula 3:
[Chemical Formula 3]
2-1
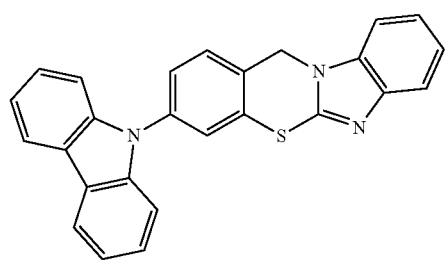
2-5
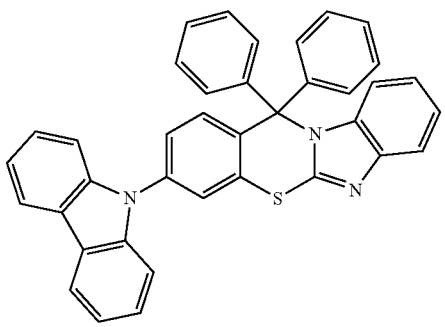
2-2
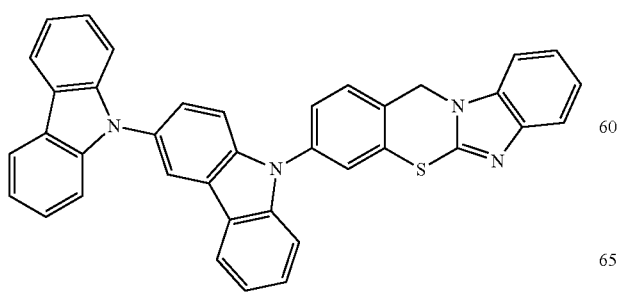
2-6
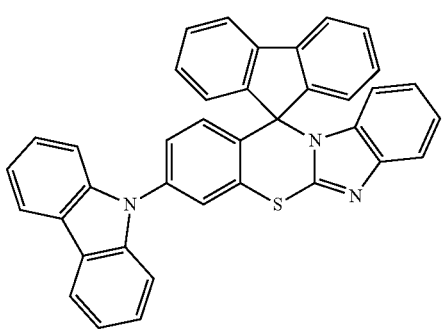

-continued
2-7
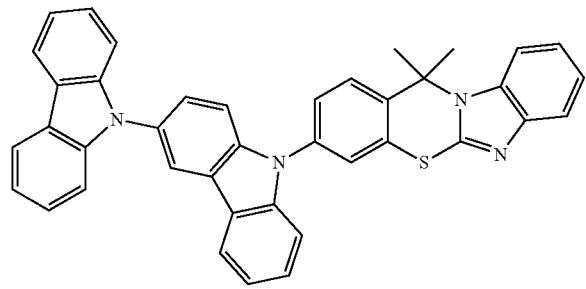
2-8
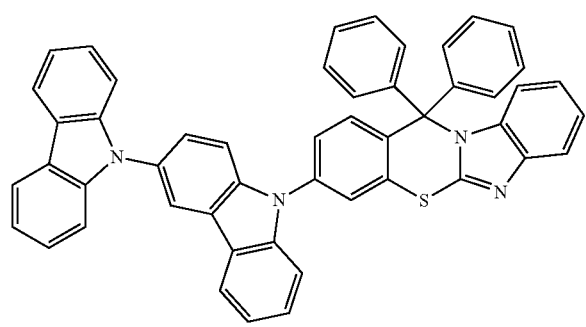
2-9
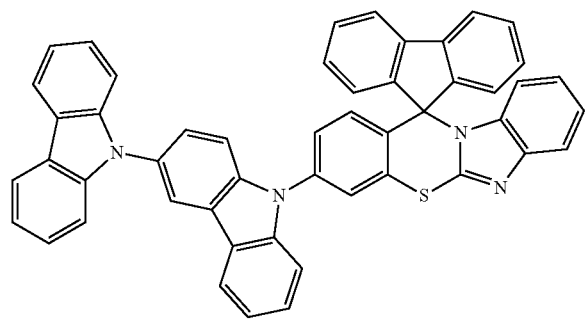
2-10
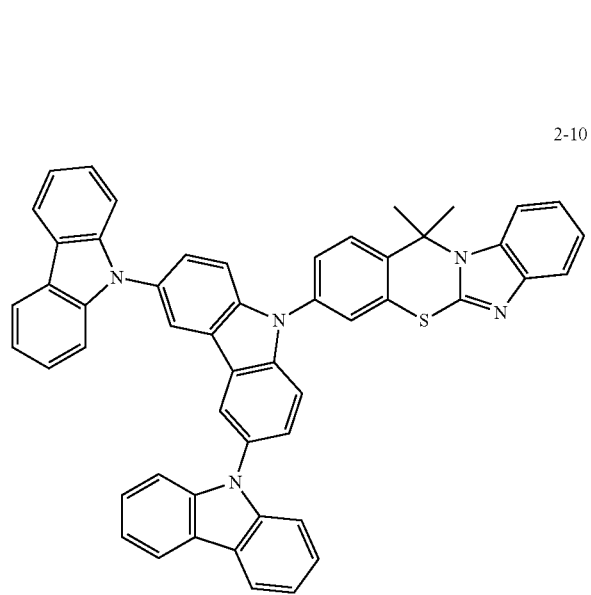
-continued
2-11
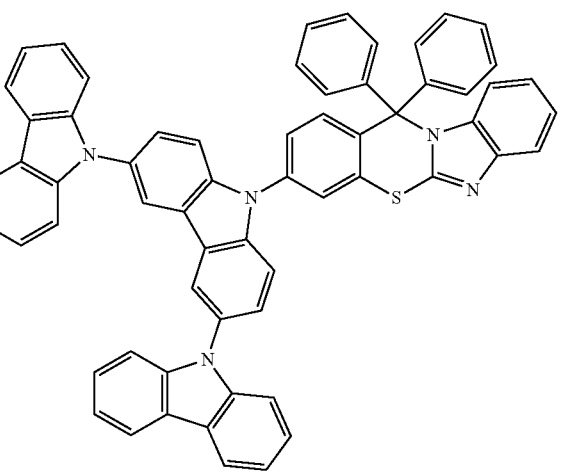
2-12
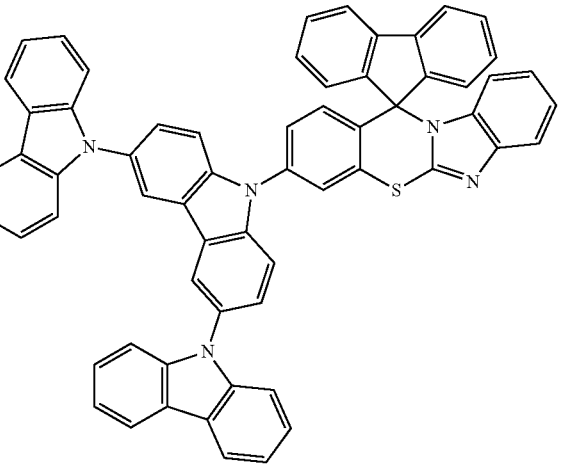
2-13
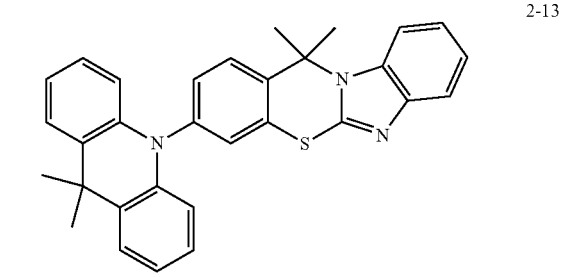
2-14

2-15
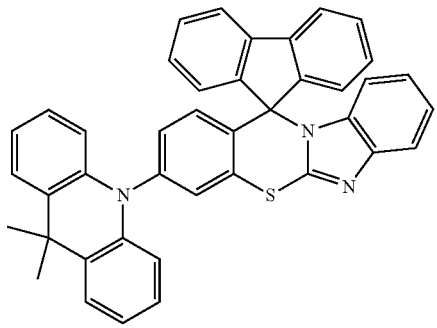
2-16
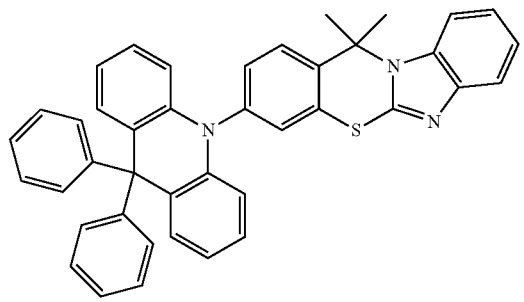
2-17
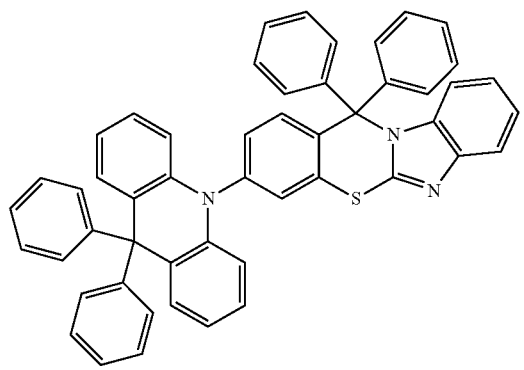
2-18
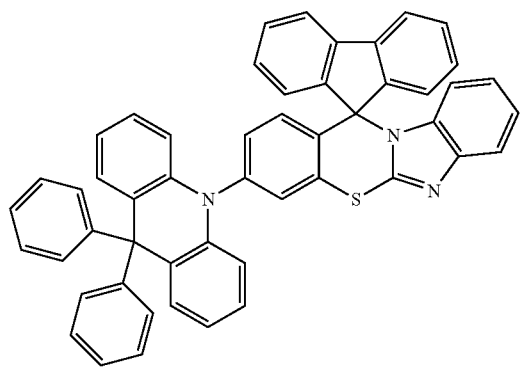
2-19
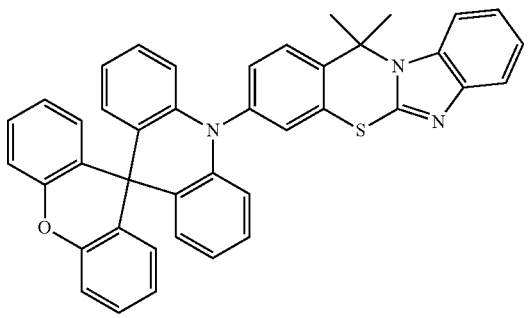
2-20
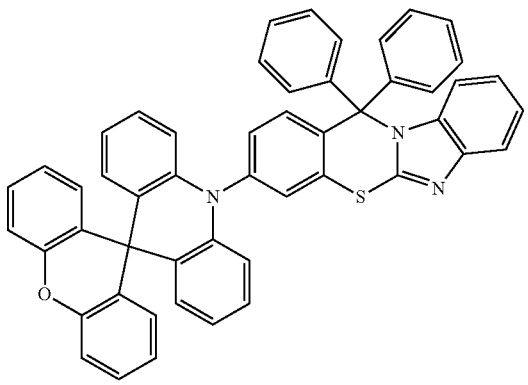
2-21
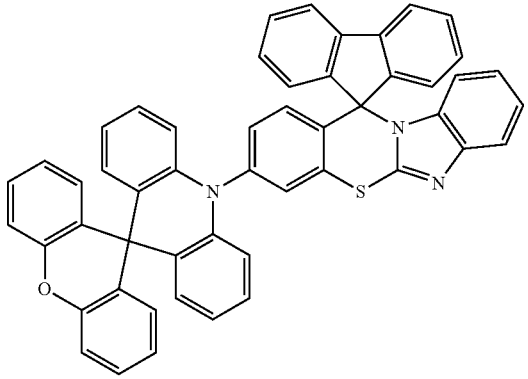
2-22
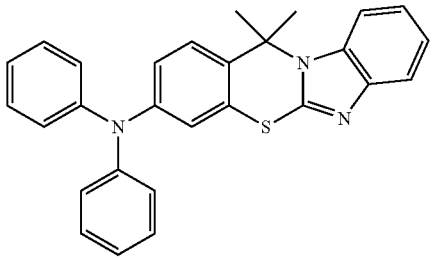

2-23
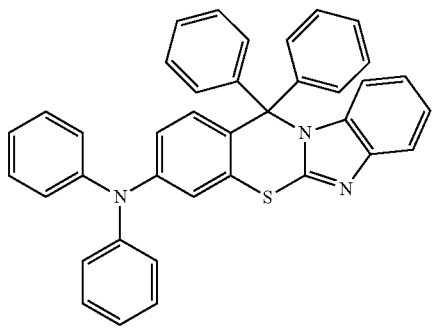
2-24
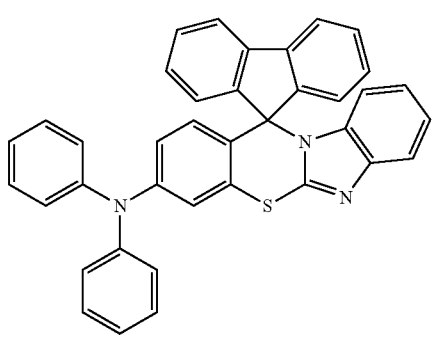
2-25
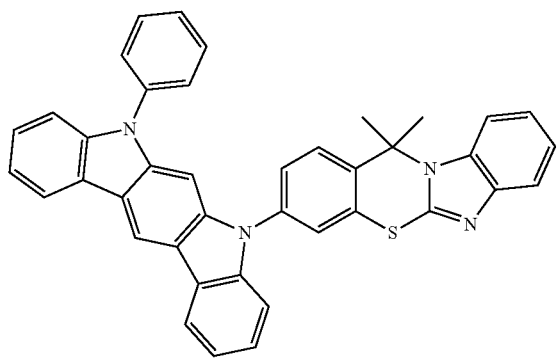
2-26
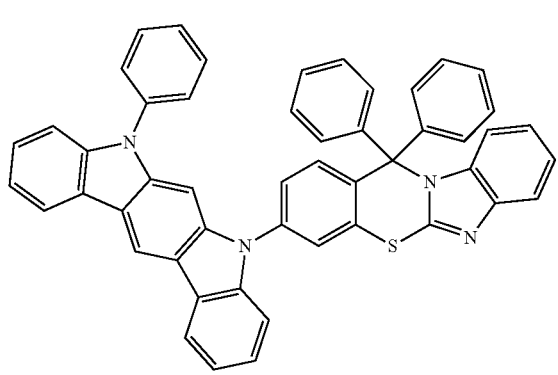
2-27
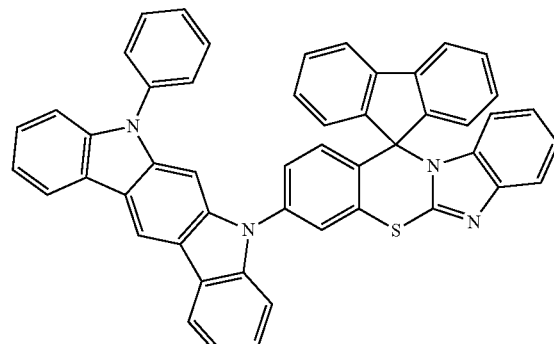
2-28
2-29
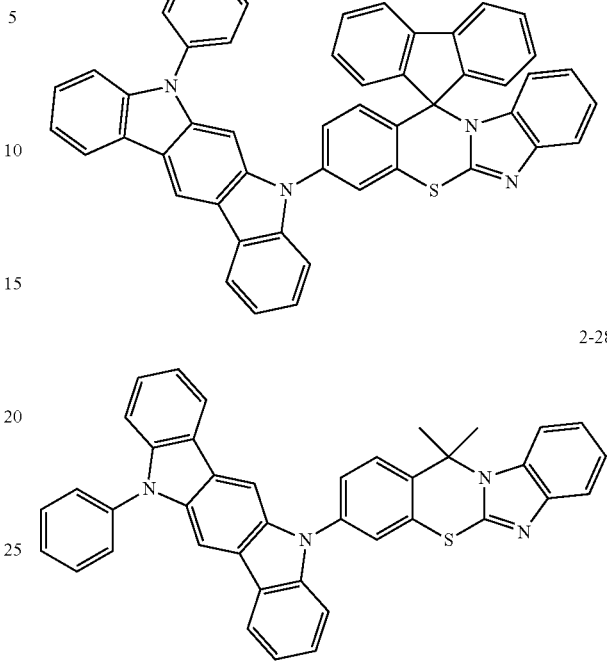
2-30
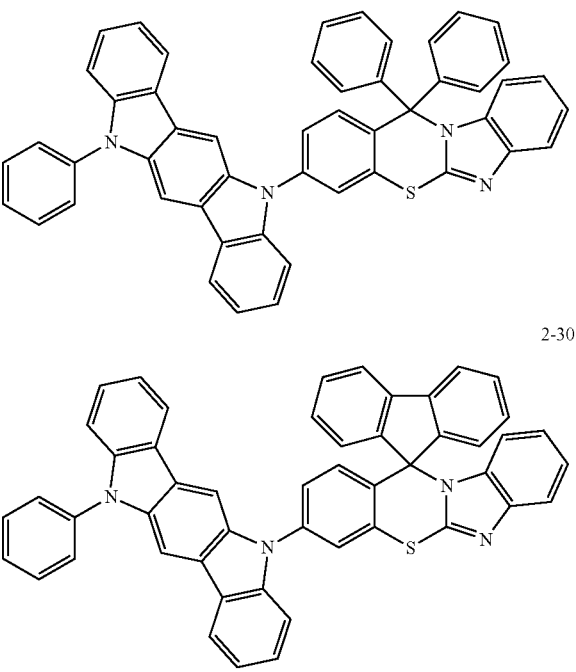
2-31
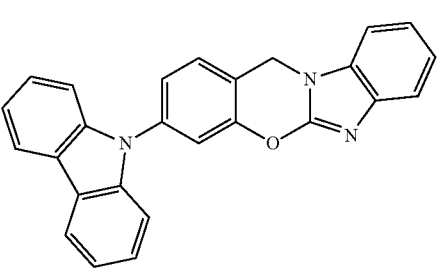

2-32
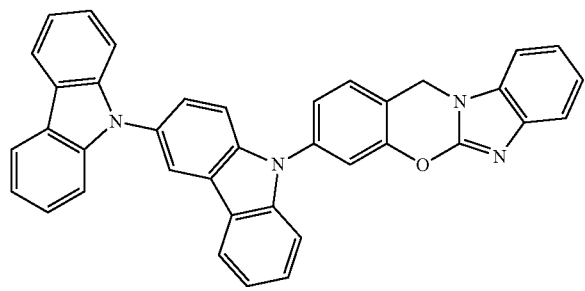
2-36
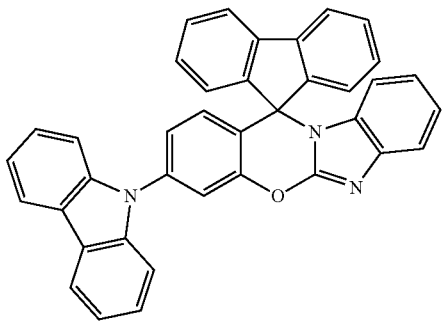
2-33
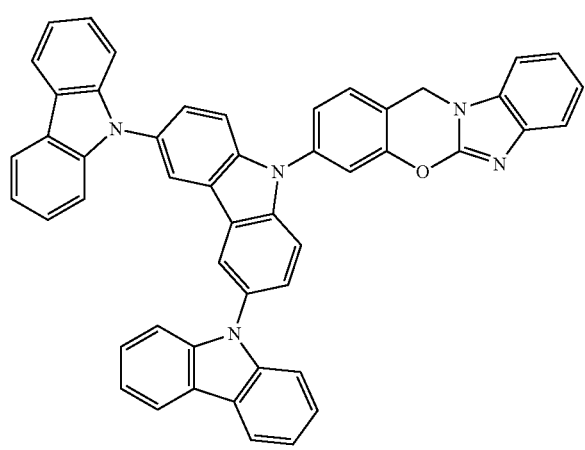
2-37
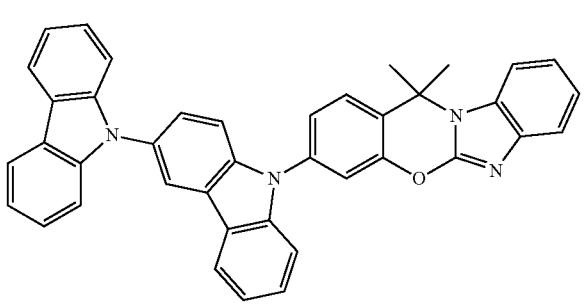
2-38
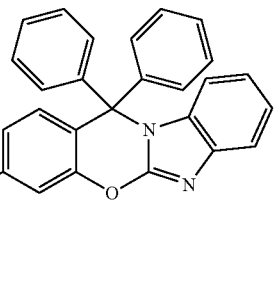
2-34
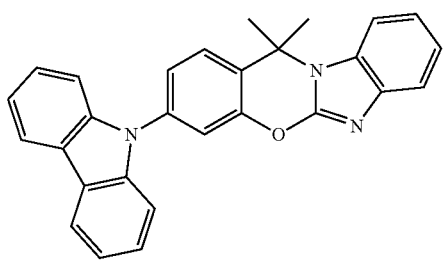
2-35
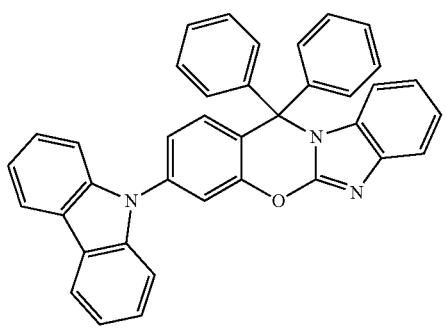
2-39
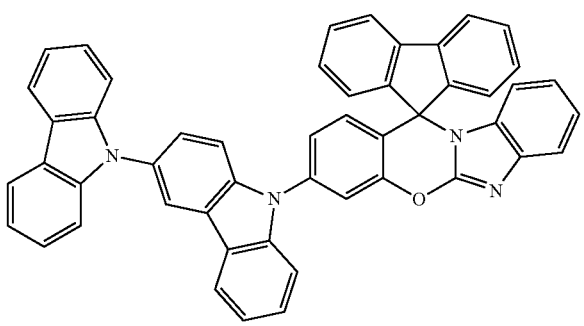

2-40
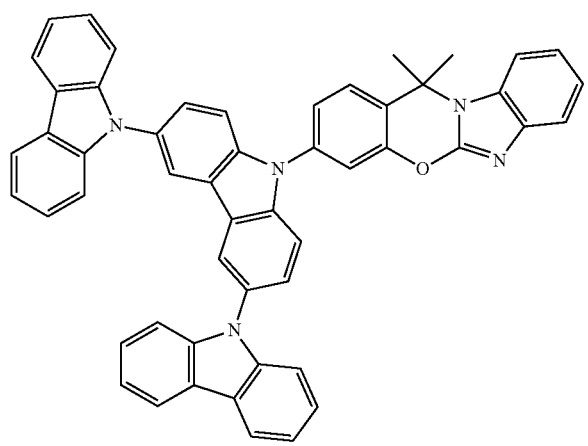
2-41
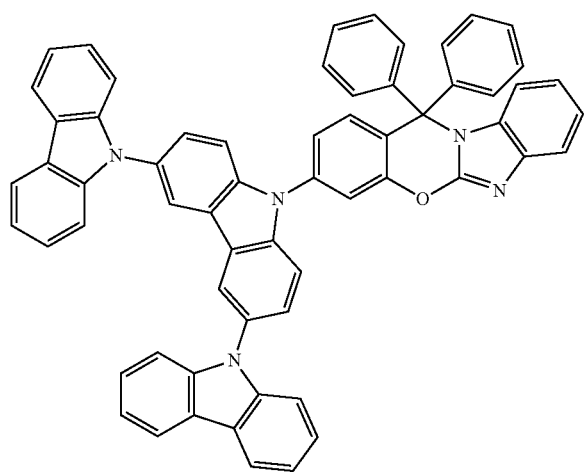
2-42
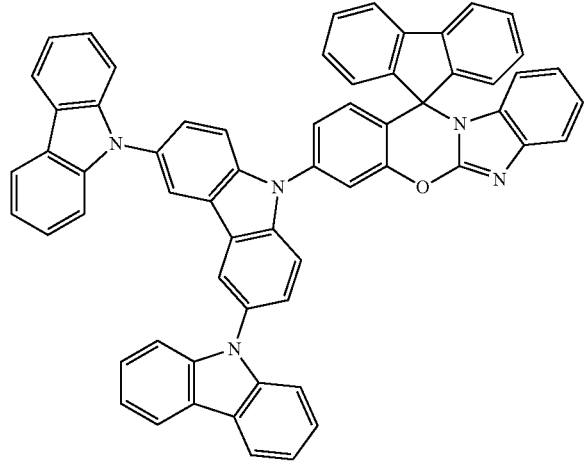
2-43
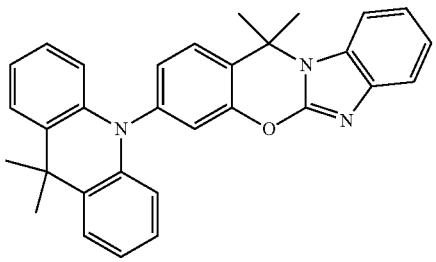
2-44
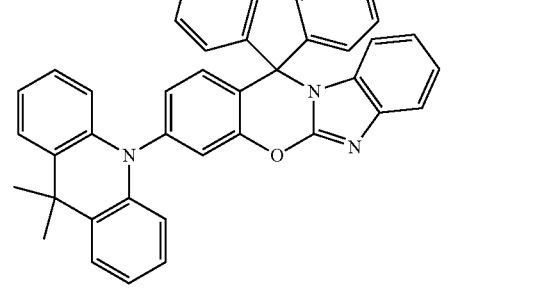
2-45
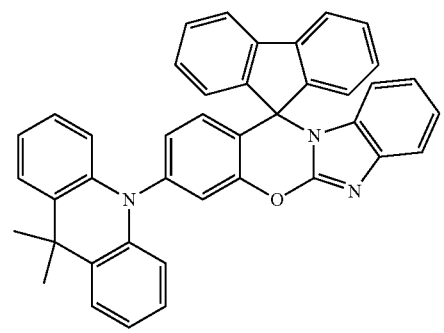
2-46
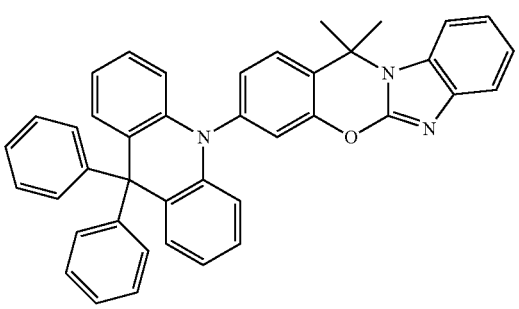
2-47
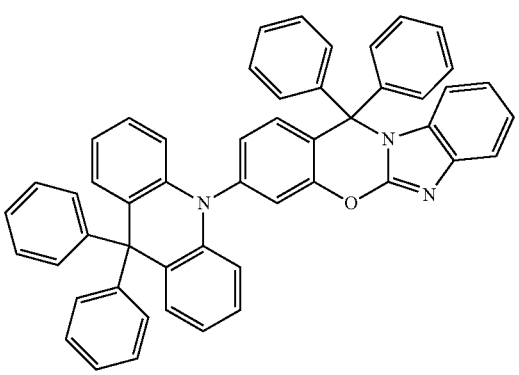

-continued
2-48
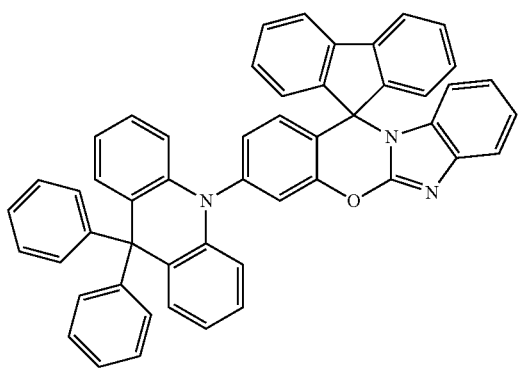
2-49
2-50
2-51
2-52
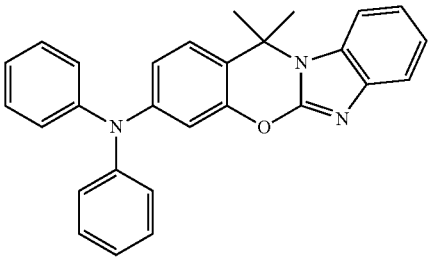
2-53
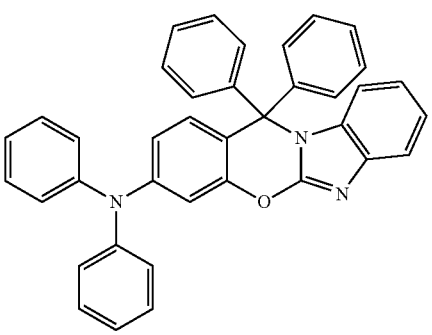
2-54
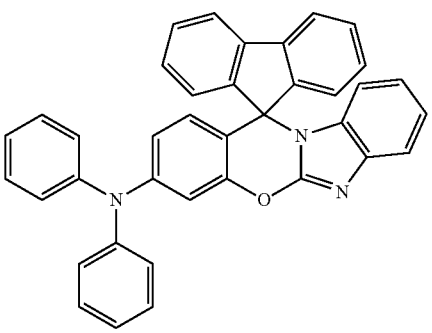
2-55
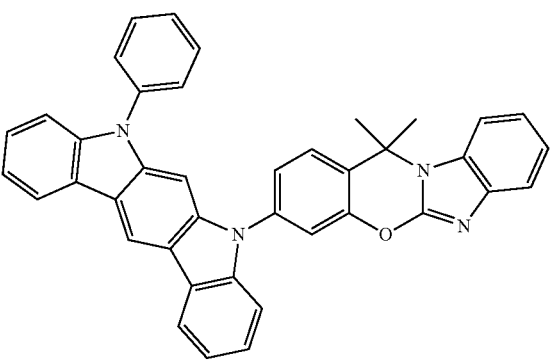

2-56

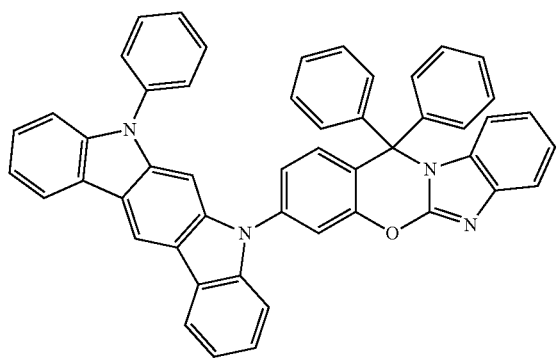

2-57

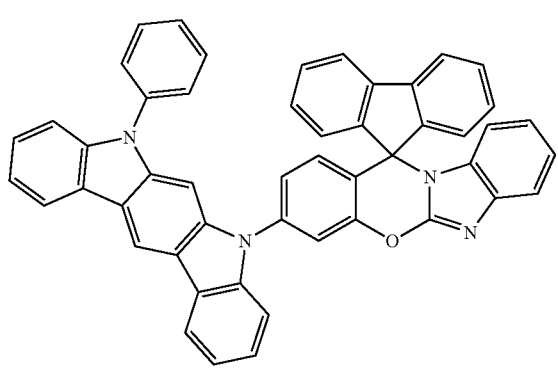

2-58

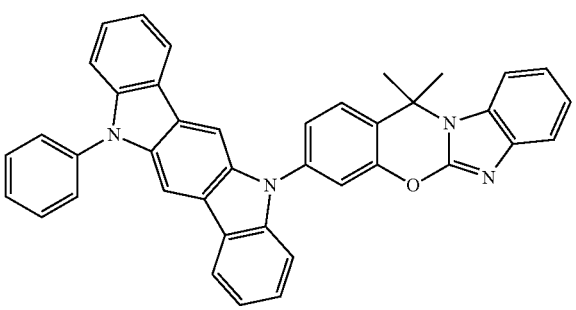

2-59

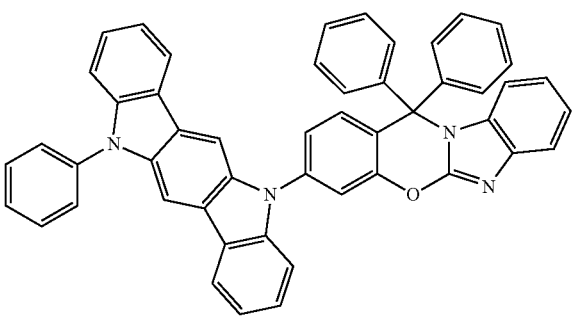

2-60

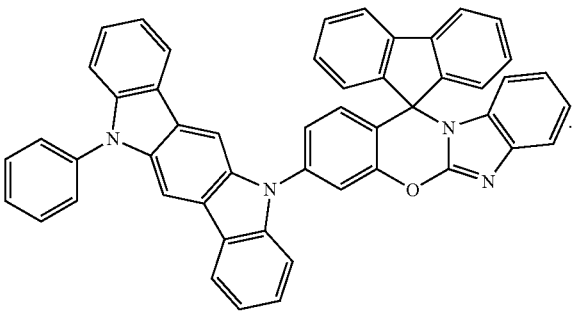

8. An organic light emitting diode comprising:
a first electrode;
a second electrode facing the first electrode; and
an emissive layer disposed between the first and second electrodes,
wherein the emissive layer comprise an organic compound having the following structure of Chemical Formula 1:

[Chemical Formula 1]

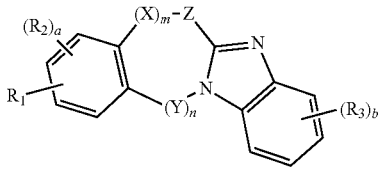

wherein $R_1$ is an unsubstituted or substituted fused hetero aromatic group having three to six aromatic or hetero aromatic rings and having one to three nitrogen atoms, an unsubstituted or substituted $C_6$-$C_{30}$ aromatic amino group or an unsubstituted or substituted $C_4$-$C_{30}$ hetero aromatic amino group;

wherein each of $R_2$ and $R_3$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, wherein each of $R_2$ and $R_3$ is identical to or different from each other when each of a and b is independently an integer two or more; each of a and b is independently the number of a substituent, a is an integer of 0 (zero) to three and b is an integer of 0 (zero) to four; each of X and Y is independently $CR_4R_5$, wherein each of $R_4$ and $R_5$ is independently selected from the group consisting of hydrogen, an unsubstituted or substituted $C_1$-$C_{30}$ alkyl group, an unsubstituted or substituted $C_6$-$C_{30}$ aromatic group and an unsubstituted or substituted $C_3$-$C_{30}$ hetero aromatic group, or $R_4$ and $R_5$ form a $C_6$-$C_{20}$ aromatic ring or a $C_3$-$C_{20}$ hetero aromatic ring; each of m and n is 0(zero) or 1, wherein m+n=1; Z is S or O.

9. The organic light emitting diode of claim 8, wherein the fused hetero aromatic group is unsubstituted, substituted with a group selected from a $C_1$-$C_{20}$ alkyl group, a $C_6$-$C_{20}$ aryl group, a $C_3$-$C_{20}$ hetero aryl group and combination thereof, or forms a spiro structure with a fluorene ring or a xanthene ring.

10. The organic light emitting diode of claim 8, wherein the fused hetero aromatic group is selected from the group consisting of a carbazolyl moiety, an acridinyl moiety, a dihydro acridinyl moiety, a phenazinyl moiety and a phenoxazinyl moiety.

11. The organic light emitting diode of claim 8, wherein the fused hetero aromatic group is unsubstituted or substituted with a group selected from a $C_1$-$C_{10}$ alkyl group, phenyl and carbazolyl and combination thereof, or forms a spiro structure with a xanthene ring, and each of $R_4$ and $R_5$ is unsubstituted or substituted with a group selected from a $C_1$-$C_{10}$ alkyl group, phenyl and combination thereof, or $R_4$ and $R_5$ forms a fluorene ring.

12. The organic light emitting diode of claim 8, wherein the emissive layer comprises at least one electron transport layer disposed between the first and second electrodes, and wherein the at least one electron transport layer comprises the organic compound.

13. The organic light emitting diode of claim 8, wherein the emissive layer comprises at least one hole blocking layer disposed between the first and second electrodes, and wherein the at least one hole blocking layer comprises the organic compound.

14. The organic light emitting diode of claim 8, wherein the emissive layer comprises a first emitting material layer disposed between the first and second electrodes, and wherein the first emitting material layer comprises the organic compound.

15. The organic light emitting diode of claim 14, wherein the first emitting material layer comprises a first compound and a second compound, wherein an excited triplet energy level of the first compound is higher than an excited triplet energy level of the second compound, and wherein the first compound comprises the organic compound.

16. The organic light emitting diode of claim 15, wherein the first emitting material layer further comprises a third compound.

17. The organic light emitting diode of claim 16, wherein an excited singlet energy level of the third compound is lower than an excited singlet energy level of the second compound.

18. The organic light emitting diode of claim 15, further comprising a second emitting material layer disposed between the first electrode and the first emitting material layer or between the first emitting material layer and the second electrode,
wherein the second emitting material layer comprises a fourth compound and a fifth compound.

19. The organic light emitting diode of claim 18, wherein the fourth compound comprises the organic compound.

20. The organic light emitting diode of claim 18, further comprising a third emitting material layer disposed oppositely to the second emitting material layer with respect to the first emitting material layer,
wherein the third emitting material layer comprises a sixth compound and a seventh compound.

21. The organic light emitting diode of claim 20, wherein at least one of the fourth compound and the sixth compound comprises the organic compound.

22. The organic light emitting diode of claim 8, wherein the emissive layer comprises a first emitting unit disposed between the first and second electrode, a second emitting unit disposed between the first emitting unit and the second electrode and a charge generation layer disposed between the first and second emitting units, and
wherein at least one of the first emitting unit and the second emitting unit comprises the organic compound.

23. An organic light emitting device comprising:
a substrate; and
an organic light emitting diode of claim 8 disposed over the substrate.

24. The organic compound of claim 1, wherein each of $R_4$ and $R_5$ is independently selected from the group consisting of a $C_1$-$C_{10}$ alkyl group and a $C_6$-$C_{30}$ aryl group, or $R_4$ and $R_5$ forms a fluorene ring.

25. The organic light emitting diode of claim 8, wherein each of $R_4$ and $R_5$ is independently selected from the group consisting of a $C_1$-$C_{10}$ alkyl group and a $C_6$-$C_{30}$ aryl group, or $R_4$ and $R_5$ forms a fluorene ring.

* * * * *